(12) United States Patent
Chen et al.

(10) Patent No.: US 12,203,894 B2
(45) Date of Patent: Jan. 21, 2025

(54) METHODS AND CIRCUITRY FOR BUILT-IN SELF-TESTING OF CIRCUITRY AND/OR TRANSDUCERS IN ULTRASOUND DEVICES

(71) Applicant: BFLY OPERATIONS, INC., Burlington, MA (US)

(72) Inventors: Chao Chen, Madison, CT (US); Youn-Jae Kook, Winchester, MA (US); Jihee Lee, Seoul (KR); Kailiang Chen, Branford, CT (US); Leung Kin Chiu, Branford, CT (US); Joseph Lutsky, Los Altos, CA (US); Nevada J. Sanchez, Guilford, CT (US); Sebastian Schaetz, Leipzig (DE); Hamid Soleimani, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 0 days.

(21) Appl. No.: 18/507,509

(22) Filed: Nov. 13, 2023

(65) Prior Publication Data
US 2024/0159714 A1 May 16, 2024

Related U.S. Application Data

(63) Continuation of application No. 17/232,100, filed on Apr. 15, 2021, now Pat. No. 11,815,492.
(Continued)

(51) Int. Cl.
*G01N 29/24* (2006.01)
*A61B 8/00* (2006.01)
(Continued)

(52) U.S. Cl.
CPC .......... *G01N 29/2406* (2013.01); *A61B 8/58* (2013.01); *G01N 29/30* (2013.01); *G01S 7/5205* (2013.01);
(Continued)

(58) Field of Classification Search
CPC ............... G01N 29/2406; G01N 29/30; G01N 2291/02475; G01N 29/44; A61B 8/58;
(Continued)

(56) References Cited

U.S. PATENT DOCUMENTS 8,852,103 B2  10/2014  Rothberg et al.
9,067,779 B1   6/2015  Rothberg et al.
(Continued)

*Primary Examiner* — Peter J Macchiarolo
*Assistant Examiner* — John M Royston
(74) *Attorney, Agent, or Firm* — Carter, DeLuca & Farrell LLP

(57) ABSTRACT

Aspects of the technology described herein relate to built-in self-testing (BIST) of circuitry (e.g., a pulser or receive circuitry) and/or transducers in an ultrasound device. A BIST circuit may include a transconductance amplifier coupled between a pulser and receive circuitry, a capacitor network coupled between a pulser and receive circuitry, and/or a current source couplable to the input terminal of receive circuitry to which a transducer is also couplable. The collapse voltages of transducers may be characterized using BIST circuitry, and a bias voltage may be applied to the membranes of the transducers based at least in part on their collapse voltages. The capacitances of transducers may also be measured using BIST circuitry and a notification may be generated based on the sets of measurements.

12 Claims, 41 Drawing Sheets

Related U.S. Application Data

(60) Provisional application No. 63/087,558, filed on Oct. 5, 2020, provisional application No. 63/046,624, filed on Jun. 30, 2020, provisional application No. 63/011,214, filed on Apr. 16, 2020.

(51) Int. Cl.
| | | |
|---|---|---|
| *B06B 1/02* | (2006.01) | |
| *G01N 29/30* | (2006.01) | |
| *G01S 7/52* | (2006.01) | |
| *G01S 15/89* | (2006.01) | |
| *H03F 1/32* | (2006.01) | |
| *H03F 3/45* | (2006.01) | |
| *H03K 5/24* | (2006.01) | |
| *H03M 3/00* | (2006.01) | |

(52) U.S. Cl.
CPC ....... *H03F 1/3211* (2013.01); *H03F 3/45475* (2013.01); *H03K 5/24* (2013.01); *H03M 3/458* (2013.01); *B06B 1/0292* (2013.01); *G01N 2291/02475* (2013.01); *G01S 15/8915* (2013.01); *H03F 2200/129* (2013.01); *H03F 2203/45116* (2013.01)

(58) Field of Classification Search
CPC .. G01S 7/5205; G01S 15/8915; H03F 1/3211; H03F 3/45475; H03F 2200/129; H03F 2203/45116; H03F 2203/45528; H03F 2203/45536; H03K 5/24; H03M 3/458; H03M 3/43; H03M 3/454; B06B 1/0292; B06B 1/0215
See application file for complete search history.

(56) References Cited

U.S. PATENT DOCUMENTS

| | | | |
|---|---|---|---|
| 9,229,097 B2 | 1/2016 | Rothberg et al. | |
| 9,242,275 B2 | 1/2016 | Rothberg et al. | |
| 9,473,136 B1 | 10/2016 | Chen et al. | |
| 9,492,144 B1 | 11/2016 | Chen et al. | |
| 9,499,392 B2 | 11/2016 | Rothberg et al. | |
| 9,505,030 B2 | 11/2016 | Rothberg et al. | |
| 9,521,991 B2 | 12/2016 | Rothberg et al. | |
| 9,533,873 B2 | 1/2017 | Rothberg et al. | |
| 9,592,030 B2 | 3/2017 | Rothberg et al. | |
| 9,592,032 B2 | 3/2017 | Rothberg et al. | |
| 9,705,518 B2 | 7/2017 | Chen et al. | |
| 9,778,348 B1 | 10/2017 | Chen et al. | |
| 9,987,661 B2 | 6/2018 | Alie | |
| 10,082,488 B2 | 9/2018 | Chen et al. | |
| 10,082,565 B2 | 9/2018 | Chen et al. | |
| 10,175,347 B2 | 1/2019 | Chen et al. | |
| 10,187,020 B2 | 1/2019 | Chen et al. | |
| 10,196,261 B2 | 2/2019 | Rothberg et al. | |
| 10,231,713 B2 | 3/2019 | Chen | |
| 10,371,804 B2 | 8/2019 | Ralston | |
| 10,512,936 B2 | 12/2019 | Alie | |
| 10,695,034 B2 | 6/2020 | Ralston et al. | |
| 10,755,692 B2 | 8/2020 | Ralston et al. | |
| 10,840,864 B2 | 11/2020 | Singh et al. | |
| 10,850,306 B2 | 12/2020 | Rothberg | |
| 10,856,840 B2 | 12/2020 | Rothberg et al. | |
| 10,857,567 B2 | 12/2020 | Singh et al. | |
| 10,859,687 B2 | 12/2020 | Bao et al. | |
| 10,972,842 B2 | 4/2021 | Lutsky et al. | |
| 11,005,435 B2 | 5/2021 | Singh et al. | |
| 11,815,492 B2 | 11/2023 | Chen | |
| 2003/0144603 A1 | 7/2003 | Zoth | |
| 2005/0121734 A1* | 6/2005 | Degertekin | B06B 1/0292 438/48 |
| 2009/0241634 A1* | 10/2009 | Acar | G01P 15/125 73/1.79 |
| 2010/0268081 A1 | 10/2010 | Asafusa | |
| 2011/0055447 A1 | 3/2011 | Costa | |
| 2014/0243614 A1 | 8/2014 | Rothberg et al. | |
| 2014/0354468 A1 | 12/2014 | Yanagi | |
| 2016/0016198 A1 | 1/2016 | Emadi | |
| 2016/0076933 A1 | 3/2016 | Leone | |
| 2017/0157646 A1 | 6/2017 | Alie | |
| 2017/0281138 A1 | 10/2017 | Bao | |
| 2017/0307740 A1 | 10/2017 | Ralston | |
| 2017/0360397 A1 | 12/2017 | Rothberg et al. | |
| 2017/0360399 A1 | 12/2017 | Rothberg et al. | |
| 2018/0070917 A1 | 3/2018 | Rothberg et al. | |
| 2018/0360426 A1 | 12/2018 | Singh et al. | |
| 2018/0364342 A1 | 12/2018 | Chen et al. | |
| 2019/0000422 A1 | 1/2019 | West et al. | |
| 2019/0001159 A1 | 1/2019 | Chen et al. | |
| 2019/0069842 A1 | 3/2019 | Rothberg et al. | |
| 2019/0142387 A1 | 5/2019 | Chen et al. | |
| 2019/0282207 A1 | 9/2019 | Chen et al. | |
| 2019/0299251 A1 | 10/2019 | Chen | |
| 2019/0336099 A1 | 11/2019 | Fife | |
| 2019/0336104 A1 | 11/2019 | Fife | |
| 2019/0343484 A1 | 11/2019 | Rothberg et al. | |
| 2019/0353700 A1 | 11/2019 | Ciubotaru | |
| 2020/0102214 A1 | 4/2020 | Liu et al. | |
| 2020/0150252 A1 | 5/2020 | Chen | |
| 2020/0315586 A1 | 10/2020 | Sanchez | |
| 2020/0315592 A1 | 10/2020 | Soleimani et al. | |
| 2020/0322454 A1 | 10/2020 | Ersson | |
| 2020/0383660 A1 | 12/2020 | Rothberg et al. | |
| 2020/0390419 A1 | 12/2020 | Neben et al. | |
| 2020/0405266 A1 | 12/2020 | Yang et al. | |
| 2020/0405267 A1 | 12/2020 | Yang et al. | |
| 2020/0405271 A1 | 12/2020 | Chiu et al. | |
| 2021/0028792 A1 | 1/2021 | Hwang et al. | |
| 2021/0056041 A1 | 2/2021 | Sanchez | |
| 2021/0088638 A1 | 3/2021 | Chen et al. | |
| 2021/0093291 A1 | 4/2021 | Sanchez | |
| 2021/0167791 A1 | 6/2021 | Hwang et al. | |
| 2021/0183832 A1 | 6/2021 | Chen et al. | |
| 2021/0328564 A1 | 10/2021 | Chen et al. | |

\* cited by examiner

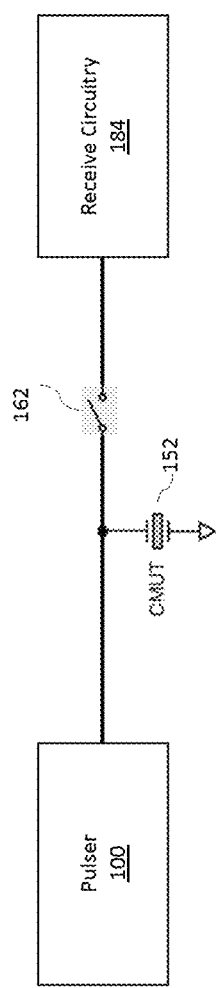

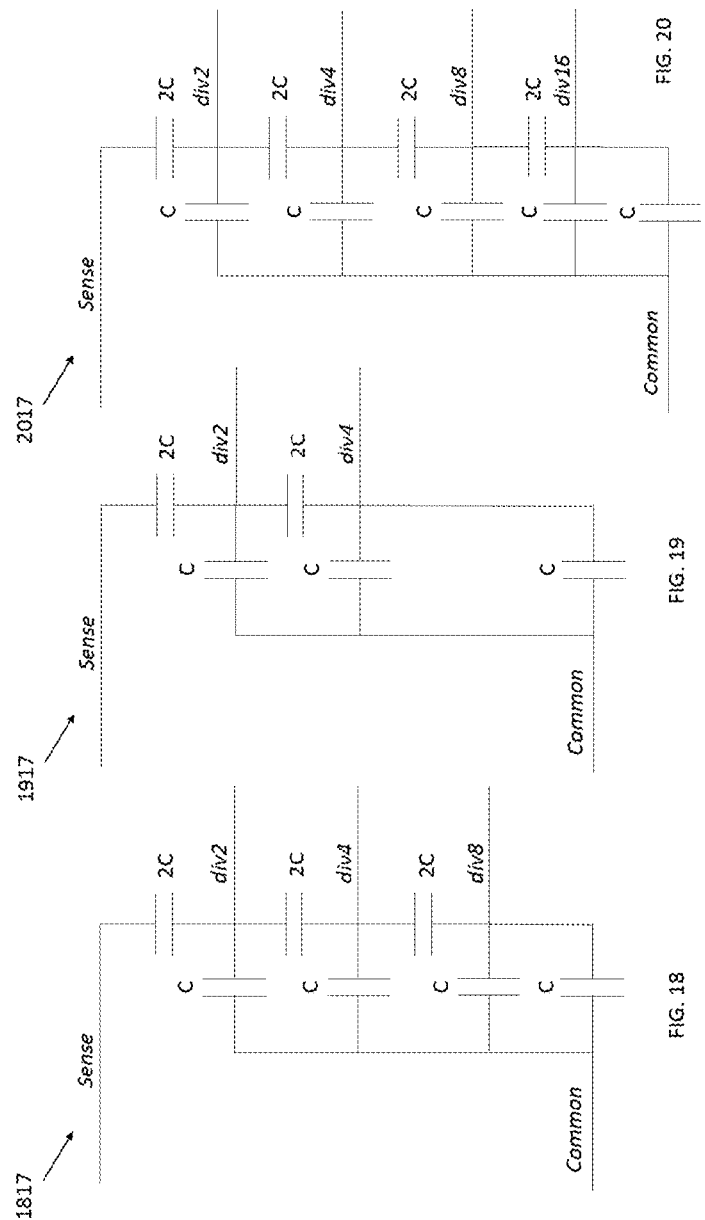

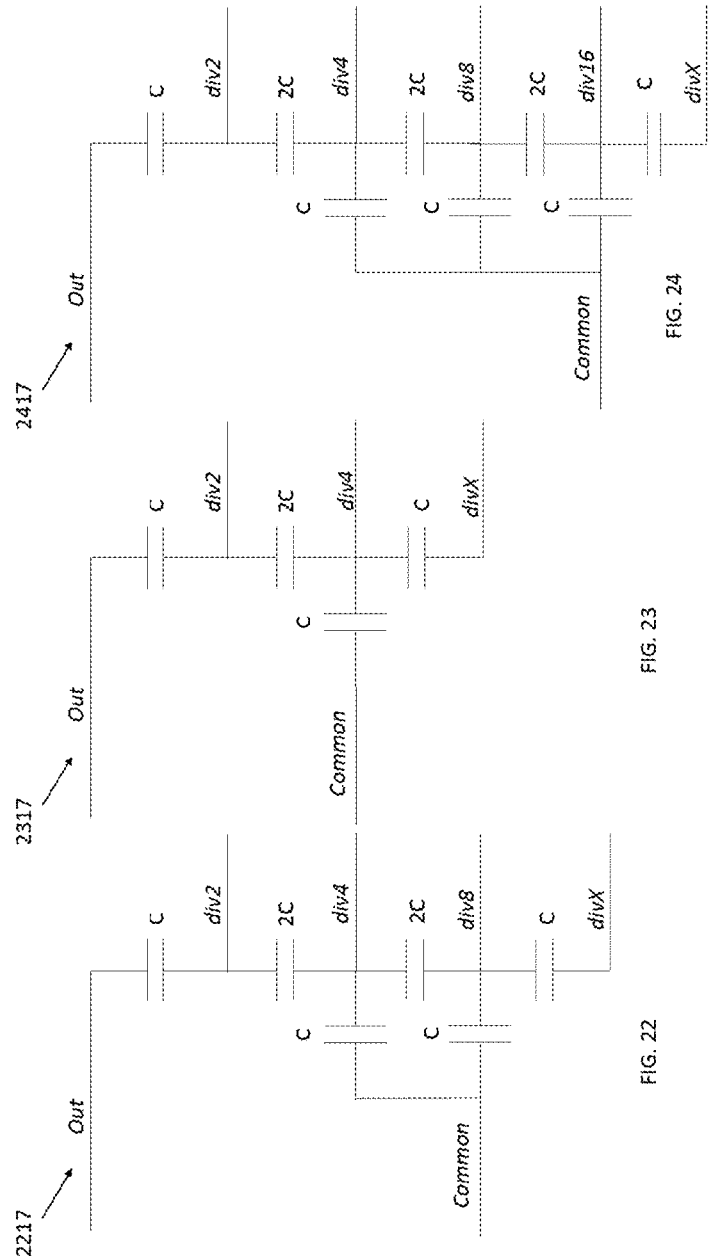

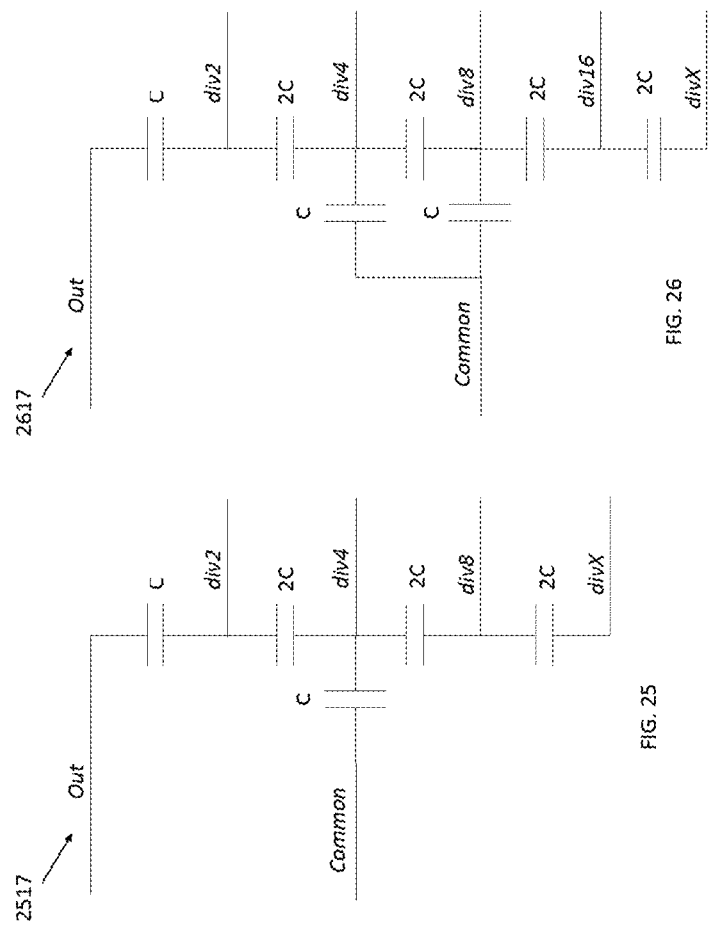

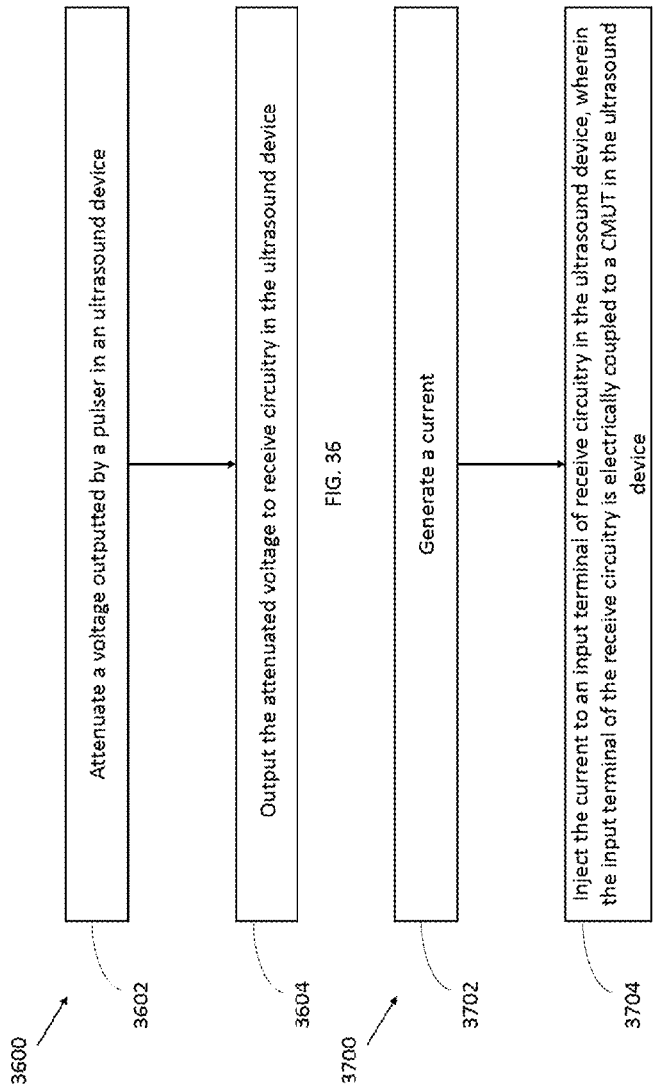

METHODS AND CIRCUITRY FOR BUILT-IN SELF-TESTING OF CIRCUITRY AND/OR TRANSDUCERS IN ULTRASOUND DEVICES

CROSS-REFERENCE TO RELATED APPLICATIONS

This application is a continuation of U.S. patent application Ser. No. 17/232,100, filed on Apr. 15, 2021, which claims the benefit of, and priority to, U.S. Provisional Patent Application Ser. No. 63/087,558 filed on Oct. 5, 2020, U.S. Provisional Patent Application Ser. No. 63/046,624, filed on Jun. 30, 2020, and U.S. Provisional Patent Application Ser. No. 63/011,214 filed on Apr. 16, 2020. The entire contents of the foregoing applications are incorporated by reference herein.

FIELD

Generally, the aspects of the technology described herein relate to ultrasound devices. Some aspects relate to methods and circuitry for built-in self-testing of circuitry and/or transducers in ultrasound devices.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect of the application, an ultrasound device comprises a pulser, receive circuitry, a capacitive micromachined ultrasonic transducer (CMUT) couplable to the receive circuitry, and a transconductance amplifier coupled between the pulser and the receive circuitry.

In some embodiments, the transconductance amplifier includes a linearized transconductance amplifier. In some embodiments, the transconductance amplifier includes a source-degenerated linearized transconductance amplifier. In some embodiments, the ultrasound device further includes a resistor ladder, and the transconductance amplifier and the pulser are configured to receive, as input signals, voltages from the resistor ladder. In some embodiments, the transconductance amplifier is coupled between the pulser and a circuit in the receive circuitry configurable as a transimpedance amplifier. In some embodiments, the transconductance amplifier is coupled between the pulser and a circuit in the receive circuitry configurable as a comparator. In some embodiments, the transconductance amplifier is coupled between the pulser and a circuit in the receive circuitry configurable as a delta-sigma analog-to-digital converter. In some embodiments, the pulser is configured to use a first power supply, the transconductance amplifier is configured to use a second power supply, the receive circuitry is configured to use a third power supply, and the first power supply has a higher voltage than the second power supply and the second power supply has a higher voltage than the third power supply. In some embodiments, the transconductance amplifier can be turned off while the pulser and the receive circuitry remain on. In some embodiments, the pulser, the receive circuitry, the CMUT, and the transconductance amplifier are disposed within a single package. In some embodiments, the transconductance amplifier is disposed on a same semiconductor chip as the pulser, the receive circuitry, and/or the CMUT. In some embodiments, the transconductance amplifier includes a built-in self-test (BIST) circuit.

According to another aspect of the application, an ultrasound device includes receive circuitry having an input terminal, a capacitive micromachined ultrasonic transducer (CMUT) couplable to the input terminal of the receive circuitry, and a current source couplable to the input terminal of the receive circuitry.

In some embodiments, the current source includes a first current source configured to supply current to the input terminal of the receive circuitry, and the ultrasound device further includes a second current source couplable to the input terminal of the receive circuitry and configured to sink current from the input terminal of the receive circuitry. In some embodiments, the receive circuitry is capable of being configured as a comparator. In some embodiments, the pulser, the receive circuitry, the CMUT, and the current source are disposed within a single package. In some embodiments, the current source is disposed on a same semiconductor chip as the pulser, the receive circuitry, and/or the CMUT. In some embodiments, the current source includes a built-in self-test (BIST) circuit.

According to another aspect of the application, an ultrasound device includes a pulser, receive circuitry, and a capacitor network coupled between the pulser and the receive circuitry.

In some embodiments, the capacitor network is coupled between the pulser and a circuit in the receive circuitry capable of being configured as a unity-gain amplifier. In some embodiments, the capacitor network is configured to attenuate an output signal from the pulser. In some embodiments, the capacitor network is configured to receive, as an input signal, an output signal from the pulser, and to output an attenuated version of the output signal from the pulser to the pulser and the receive circuitry. In some embodiments, the pulser, the receive circuitry, and the capacitor network are disposed within a single package. In some embodiments, the capacitor network is disposed on a same semiconductor chip as the pulser and/or the receive circuitry. In some embodiments, the capacitor network includes a built-in self-test (BIST) circuit.

According to another aspect of the application, an ultrasound device includes a pulser, a transconductance amplifier, and receive circuitry, and a method for testing the pulser in the ultrasound device includes converting a voltage output by the pulser to a current using the transconductance amplifier and outputting the current from the transconductance amplifier to the receive circuitry.

In some embodiments, the transconductance amplifier includes a linearized transconductance amplifier. In some embodiments, the transconductance amplifier includes a source-degenerated linearized transconductance amplifier. In some embodiments, the transconductance amplifier and the pulser receive, as input signals, voltages from a resistor ladder. In some embodiments, outputting the current from the transconductance amplifier to the receive circuitry includes outputting the current to a transimpedance amplifier in the receive circuitry. In some embodiments, outputting the current from the transconductance amplifier to the receive circuitry includes outputting the current to a delta-sigma analog-to-digital converter in the receive circuitry. In some embodiments, the pulser uses a first power supply, the transconductance amplifier uses a second power supply, the receive circuitry uses a third power supply, and the first power supply has a higher voltage than the second power supply and the second power supply has a higher voltage than the third power supply. In some embodiments, the method further includes turning off the transconductance amplifier while the pulser and the receive circuitry remain on. In some embodiments, the pulser, the receive circuitry, a capacitive micromachined ultrasonic transducer (CMUT), and the transconductance amplifier are disposed within a single package. In some embodiments, the transconductance amplifier is disposed on a same semiconductor chip as the pulser, the receive circuitry, and/or a capacitive micromachined ultrasonic transducer (CMUT). In some embodiments, the transconductance amplifier includes a built-in self-test (BIST) circuit.

According to another aspect of the application, a method for characterizing a capacitive micromachined ultrasonic transducer (CMUT) in an ultrasound device includes generating a current using a transconductance amplifier of the ultrasound device and injecting the current to an input terminal of receive circuitry in the ultrasound device, where the input terminal of the receive circuitry is electrically coupled to the CMUT.

In some embodiments, generating the current includes generating a constant current. In some embodiments, the transconductance amplifier includes a linearized transconductance amplifier. In some embodiments, the transconductance amplifier includes a source-degenerated linearized transconductance amplifier. In some embodiments, injecting the current to the input terminal of the receive circuitry includes injecting the current to an input terminal of a comparator in the receive circuitry. In some embodiments, the current charges or discharges the CMUT to generate a ramp voltage, and the method further includes measuring a time it takes for the ramp voltage to cross a reference voltage. In some embodiments, the method further includes applying a first bias voltage to the CMUT and the current charges or discharges the CMUT to generate a first ramp voltage when the first bias voltage is applied to the CMUT, measuring a first time it takes for the first ramp voltage to cross a reference voltage applying a second bias voltage to the CMUT and the current charges or discharges the CMUT to generate a second ramp voltage when the second bias voltage is applied to the CMUT, and measuring a second time it takes for the second ramp voltage to cross the reference voltage. In some embodiments, the first bias voltage is applied before the second bias voltage, and the first bias voltage is smaller than the second bias voltage. In some embodiments, the method further includes transmitting measurements of the first time and the second time to a processing device in operative communication with the ultrasound device. In some embodiments, the receive circuitry, the CMUT, and the transconductance amplifier are disposed within a single package. In some embodiments, the transconductance amplifier is disposed on a same semiconductor chip as the receive circuitry, and/or the CMUT. In some embodiments, the transconductance amplifier includes a built-in self-test (BIST) circuit.

According to another aspect of the application, a method for testing circuitry of an ultrasound device includes converting a voltage outputted by a pulser in the ultrasound device to a first current using a transconductance amplifier, outputting the first current to receive circuitry in the ultrasound device, generating a second current using the transconductance amplifier, and injecting the second current to an input terminal of the receive circuitry in the ultrasound device, where the input terminal of the receive circuitry is electrically coupled to a capacitive micromachined ultrasonic transducer (CMUT) of the ultrasound device.

In some embodiments, the transconductance amplifier includes a linearized transconductance amplifier. In some embodiments, the transconductance amplifier includes a source-degenerated linearized transconductance amplifier. In some embodiments, the transconductance amplifier and the pulser receive, as input signals, voltages from a resistor ladder. In some embodiments, outputting the first current to the receive circuitry includes outputting the first current to a transimpedance amplifier in the receive circuitry. In some embodiments, outputting the first current to the receive circuitry includes outputting the first current to a delta-sigma analog-to-digital converter in the receive circuitry. In some embodiments, generating the second current includes generating a constant current. In some embodiments, injecting the second current to the input terminal of the receive circuitry includes injecting the second current to an input terminal of a comparator in the receive circuitry. In some embodiments, the second current is integrated onto the CMUT to generate a ramp voltage, and the method further includes measuring a time it takes for the ramp voltage to cross a reference voltage. In some embodiments, the method further includes applying a first bias voltage to the CMUT and the second current is integrated onto the CMUT to generate a first ramp voltage when the first bias voltage is applied to the CMUT, measuring a first time it takes for the first ramp voltage to cross a reference voltage, applying a second bias voltage to the CMUT and the second current is integrated onto the CMUT to generate a second ramp voltage when the second bias voltage is applied to the CMUT, and measuring a second time it takes for the second ramp voltage to cross the reference voltage. In some embodiments, the first bias voltage is applied before the second bias voltage, and the first bias voltage is smaller than the second bias voltage. In some embodiments, the method further includes transmitting measurements of the first time and the second time to a processing device in operative communication with the ultrasound device. In some embodiments, the pulser uses a first power supply, the transconductance amplifier uses a second power supply, the receive circuitry uses a third power supply, and the first power supply has a higher voltage than the second power supply and the second power supply has a higher voltage than the third power supply. In some embodiments, the method further includes turning off the transconductance amplifier while the pulser and the receive circuitry remain on. In some embodiments, the pulser, the receive circuitry, the CMUT, and the transconductance amplifier are disposed within a single package. In some embodiments, the transconductance amplifier is disposed on a same semiconductor chip as the pulser, the receive circuitry, and/or the CMUT. In some embodiments, the transconductance amplifier includes a built-in self-test (BIST) circuit.

According to another aspect of the application, a method for characterizing a capacitive micromachined ultrasonic transducer (CMUT) in an ultrasound device includes operating a current source in the ultrasound device to inject a current to an input terminal of receive circuitry in the ultrasound device, where the input terminal is electrically coupled to the CMUT.

In some embodiments, injecting the current to the input terminal of the receive circuitry includes injecting the current to the input terminal of a comparator in the receive circuitry. In some embodiments, the current charges or discharges the CMUT to generate a ramp voltage, and the method further includes measuring a time it takes for the ramp voltage to cross a reference voltage. In some embodiments, injecting the current to the input terminal of the receive circuitry includes sourcing a first current to the input terminal of the receive circuitry, where the first current charges the CMUT to generate a first ramp voltage, and the method further includes measuring a first time it takes for the first ramp voltage to cross a reference voltage, sinking a second current from the input terminal of the receive circuitry, where the second current discharges the CMUT to generate a second ramp voltage, and measuring a second time it takes for the second ramp voltage to cross the reference voltage. In some embodiments, the method further includes applying a first bias voltage to the CMUT and the current is integrated onto the CMUT to generate a first ramp voltage when the first bias voltage is applied to the CMUT, measuring a first time it takes for the first ramp voltage to cross a reference voltage, applying a second bias voltage to the CMUT and the current is integrated onto the CMUT to generate a second ramp voltage when the second bias voltage is applied to the CMUT, and measuring a second time it takes for the second ramp voltage to cross the reference voltage. In some embodiments, the first bias voltage is applied before the second bias voltage, and the first bias voltage is smaller than the second bias voltage. In some embodiments, the method further includes transmitting measurements of the first time and the second time to a processing device in operative communication with the ultrasound device. In some embodiments, the receive circuitry, the CMUT, and the current source are disposed within a single package. In some embodiments, the current source is disposed on a same semiconductor chip as the receive circuitry and/or the CMUT. In some embodiments, the current source includes a built-in self-test (BIST) circuit.

According to another aspect of the application, a method for testing a pulser in an ultrasound device includes attenuating a voltage outputted by the pulser using a capacitor network in the ultrasound device and outputting the attenuated voltage from the capacitor network to receive circuitry in the ultrasound device.

In some embodiments, outputting the attenuated voltage to the receive circuitry includes outputting the attenuated voltage to a unity-gain amplifier in the receive circuitry. In some embodiments, the method further includes providing a feedback voltage to the pulser. In some embodiments, the feedback voltage is attenuated relative to the voltage outputted by the pulser. In some embodiments, the pulser, the receive circuitry, and the capacitor network are disposed within a single package. In some embodiments, the capacitor network is disposed on a same semiconductor chip as the pulser and/or the receive circuitry. In some embodiments, the capacitor network includes a built-in self-test (BIST) circuit.

According to another aspect of the application, a method for testing receive circuitry in an ultrasound device, includes converting a voltage outputted by the pulser to a current using a transconductance amplifier in the ultrasound device and outputting the current from the transconductance amplifier to the receive circuitry in the ultrasound device.

In some embodiments, the transconductance amplifier includes a linearized transconductance amplifier. In some embodiments, the transconductance amplifier includes a source-degenerated linearized transconductance amplifier. In some embodiments, the pulser, the receive circuitry, and the transconductance amplifier are disposed within a single package. In some embodiments, the transconductance amplifier is disposed on a same semiconductor chip as the pulser and/or the receive circuitry. In some embodiments, the transconductance amplifier includes a built-in self-test (BIST) circuit.

According to another aspect of the application, an apparatus includes a processing device in operative communication with an ultrasound device, the processing device configured to: receive, from the ultrasound device sets of measurements of capacitances or a parameter related to the capacitances of one or more CMUTs in the ultrasound device at each of multiple bias voltages applied to the membranes of the CMUTs; determine collapse voltages of the one or more CMUTs based on the capacitances of the CMUTs at each of the multiple bias voltages; and cause the ultrasound device to apply a bias voltage to the membranes of the CMUTs based at least in part on the collapse voltages of the one or more CMUTs.

In some embodiments, each of the measurements of the parameter related to the capacitances of the one or more CMUTs in the ultrasound device includes a measurement of a time for a ramp voltage to cross a reference voltage, and where a current is integrated onto one of the CMUTs to generate the ramp voltage when a particular bias voltage of the multiple bias voltages is applied to the CMUT. In some embodiments, the processing device is further configured to compute the capacitances of the one or more CMUTs in the ultrasound device based on the measurements of the parameter related to the capacitances of the one or more CMUTs in the ultrasound device. In some embodiments, the processing device is configured, when determining the collapse voltages of the one or more CMUTs based on the capacitances of the one or more CMUTs at each of the multiple bias voltages, to determine a particular bias voltage at which a discontinuity occurs in a curve of capacitance versus bias voltage for each of the one or more CMUTs. In some embodiments, the processing device is further configured to average the collapse voltages of the one or more CMUTs to produce an average of the collapse voltages. In some embodiments, the processing device is configured, when causing the ultrasound device to apply the bias voltage to the membranes of the one or more CMUTs based at least in part on the collapse voltages of the one or more CMUTs, to cause the ultrasound device to apply a bias voltage to the membranes of the one or more CMUTs that is greater than the average of the collapse voltages by an offset voltage. In some embodiments, the membranes of the one or more CMUTs include one shared membrane. In some embodiments, the offset voltage is approximately equal to or between 25-30V. In some embodiments, the processing device is further configured to use different offset voltages when the ultrasound device is imaging different anatomical regions.

According to another aspect of the application, a method includes: receiving, by a processing device in operative communication with an ultrasound device and from the ultrasound device, sets of measurements of capacitances or a parameter related to the capacitances of one or more CMUTs in the ultrasound device at each of multiple bias voltages applied to the membranes of the one or more CMUTs; determining collapse voltages of the one or more CMUTs based on the capacitances of the one or more CMUTs at each of the multiple bias voltages; and causing the ultrasound device to apply a bias voltage to the membranes of the one or more CMUTs based at least in part on the collapse voltages of the one or more CMUTs.

In some embodiments, each of the measurements of the parameter related to the capacitances of the one or more CMUTs in the ultrasound device includes a measurement of a time for a ramp voltage to cross a reference voltage, and where a current is integrated onto one of the one or more CMUTs to generate the ramp voltage when a particular bias voltage of the multiple bias voltages is applied to the CMUT. In some embodiments, the method further includes computing the capacitances of the one or more CMUTs in the ultrasound device based on the measurements of the parameter related to the capacitances of the one or more CMUTs in the ultrasound device. In some embodiments, determining the collapse voltages of the one or more CMUTs based on the capacitances of the one or more CMUTs at each of the multiple bias voltages, includes determining a particular bias voltage at which a discontinuity occurs in a curve of capacitance versus bias voltage for each of the one or more CMUTs. In some embodiments, the method further includes averaging the collapse voltages of the one or more CMUTs to produce an average of the collapse voltages. In some embodiments, causing the ultrasound device to apply the bias voltage to the membranes of the one or more CMUTs based at least in part on the collapse voltages of the one or more CMUTs includes causing the ultrasound device to apply a bias voltage to the membranes of the one or more CMUTs that is greater than the average of the collapse voltages by an offset voltage. In some embodiments, the membranes of the one or more CMUTs include one shared membrane. In some embodiments, the offset voltage is approximately equal to or between 25-30V. In some embodiments, the method further includes using different offset voltages when the ultrasound device is imaging different anatomical regions.

According to another aspect of the application, an apparatus includes a processing device in operative communication with an ultrasound device, the processing device configured to: receive, from the ultrasound device sets of measurements of a capacitance or a parameter related to the capacitance of one or more CMUTs in the ultrasound device at each of multiple bias voltages applied to the membranes of the one or more CMUTs; and generate a notification based on the sets of measurements.

In some embodiments, each of the measurements of the parameter related to the capacitances of the one or more CMUTs in the ultrasound device includes a measurement of a time for a ramp voltage to cross a reference voltage, and where a current is integrated onto one of the CMUTs to generate the ramp voltage when a particular bias voltage of the multiple bias voltages is applied to the CMUT. In some embodiments, the processing device is further configured to compute the capacitances of the one or more CMUTs in the ultrasound device based on the measurements of the parameter related to the capacitances of the one or more CMUTs in the ultrasound device. In some embodiments, the processing device is further configured to count a number of the CMUTs having a membrane stuck to a substrate. In some embodiments, the processing device is configured, when counting the number of the CMUTs having a membrane stuck to a substrate, to count a number of the CMUTs lacking a discontinuity in a curve of capacitance versus bias voltage for each of the one or more CMUTs. In some embodiments, the processing device is configured to generate the notification based on the sets of measurements when the number of the CMUTs, a percentage of the CMUTs measured, and/or a percentage of the CMUTs in an array of the ultrasound device have a membrane stuck to the substrate. In some embodiments, the notification includes a notification that the ultrasound device should be replaced. In some embodiments, the processing device is configured, when generating the notification, to generate the notification on a display screen of the processing device. In some embodiments, the processing device is configured, when generating the notification, to transmit the notification to a supplier of the ultrasound device.

According to another aspect of the application, a method includes receiving, by a processing device in operative communication with an ultrasound device and from the ultrasound device, sets of measurements of a capacitance or a parameter related to the capacitance of one or more CMUTs in the ultrasound device at each of multiple bias voltages applied to the membranes of the one or more CMUTs; and generating a notification based on the sets of measurements.

In some embodiments, each of the measurements of the parameter related to the capacitances of the one or more CMUTs in the ultrasound device includes a measurement of a time for a ramp voltage to cross a reference voltage, and where a current is integrated onto one of the CMUTs to generate the ramp voltage when a particular bias voltage of the multiple bias voltages is applied to the CMUT. In some embodiments, the method further includes computing the capacitances of the one or more CMUTs in the ultrasound device based on the measurements of the parameter related to the capacitances of the one or more CMUTs in the ultrasound device. In some embodiments, the method further includes counting a number of the CMUTs having a membrane stuck to a substrate. In some embodiments, counting the number of the CMUTs having a membrane stuck to a substrate including counting a number of the CMUTs lacking a discontinuity in a curve of capacitance versus bias voltage for each of the one or more CMUTs. In some embodiments, generating the notification is performed based on the sets of measurements when the number of the CMUTs, a percentage of the CMUTs measured, and/or a percentage of the CMUTs in an array of the ultrasound device have a membrane stuck to the substrate. In some embodiments, the notification includes a notification that the ultrasound device should be replaced. In some embodiments, generating the notification includes generating the notification on a display screen of the processing device. In some embodiments, generating the notification includes transmitting the notification to a supplier of the ultrasound device.

According to another aspect of the application, an ultrasound device includes receive circuitry having an input terminal, a capacitor coupled to the input terminal of the receive circuitry, and a current source couplable to the input terminal of the receive circuitry.

In some embodiments, the current source comprises a first current source configured to supply current to the capacitor and thereby generate a first ramp voltage at the input terminal of the receive circuitry, and the ultrasound device further comprises a second current source couplable to the input terminal of the receive circuitry and configured to sink current from the capacitor and thereby generate a second ramp voltage at the input terminal of the receive circuitry. In some embodiments, the receive circuitry is capable of being configured as a unity-gain amplifier. In some embodiments, the receive circuitry, the capacitor, and the current source are disposed within a single package. In some embodiments, the current source and the capacitor are disposed on a same semiconductor chip as the receive circuitry. In some embodiments, the current source and the capacitor comprise a built-in self-test (BIST) circuit.

According to another aspect of the application, a method for testing receive circuitry in an ultrasound device includes operating a current source in the ultrasound device to inject a current to an input terminal of the receive circuitry in the ultrasound device, wherein the input terminal is electrically coupled to a capacitor.

In some embodiments, injecting the current to the input terminal of the receive circuitry comprises charging or discharging the capacitor to generate a ramp voltage at an input terminal of the receive circuitry. In some embodiments, the receive circuitry is configured to operate as a unity-gain amplifier. In some embodiments, the receive circuitry, the capacitor, and the current source are disposed within a single package. In some embodiments, the current source and the capacitor are disposed on a same semiconductor chip as the receive circuitry. In some embodiments, the current source and the capacitor comprise a built-in self-test (BIST) circuit.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 1 is an example schematic diagram illustrating circuitry in an ultrasound system, in accordance with certain embodiments described herein;

FIG. 2 illustrates transistor symbols used for the three different types of transistors, in accordance with certain embodiments described herein;

FIG. 18 is a circuit diagram of an example capacitor network, in accordance with certain embodiments described herein;

FIG. 19 is a circuit diagram of another example capacitor network, in accordance with certain embodiments described herein;

FIG. 20 is a circuit diagram of another example capacitor network, in accordance with certain embodiments described herein;

FIG. 22 is a circuit diagram of an example capacitor network, in accordance with certain embodiments described herein;

FIG. 23 is a circuit diagram of an example capacitor network, in accordance with certain embodiments described herein;

FIG. 24 is a circuit diagram of another example capacitor network, in accordance with certain embodiments described herein;

FIG. 25 is a circuit diagram of an example capacitor network, in accordance with certain embodiments described herein;

FIG. 26 is a circuit diagram of another example capacitor network, in accordance with certain embodiments described herein;

FIG. 36 illustrates a flow diagram for a process for testing a pulser in an ultrasound device, in accordance with certain embodiments described herein;

FIG. 37 illustrates a flow diagram for a process for characterizing a capacitive micromachined ultrasonic transducer (CMUT), in accordance with certain embodiments described herein;

DETAILED DESCRIPTION

Figure 3:
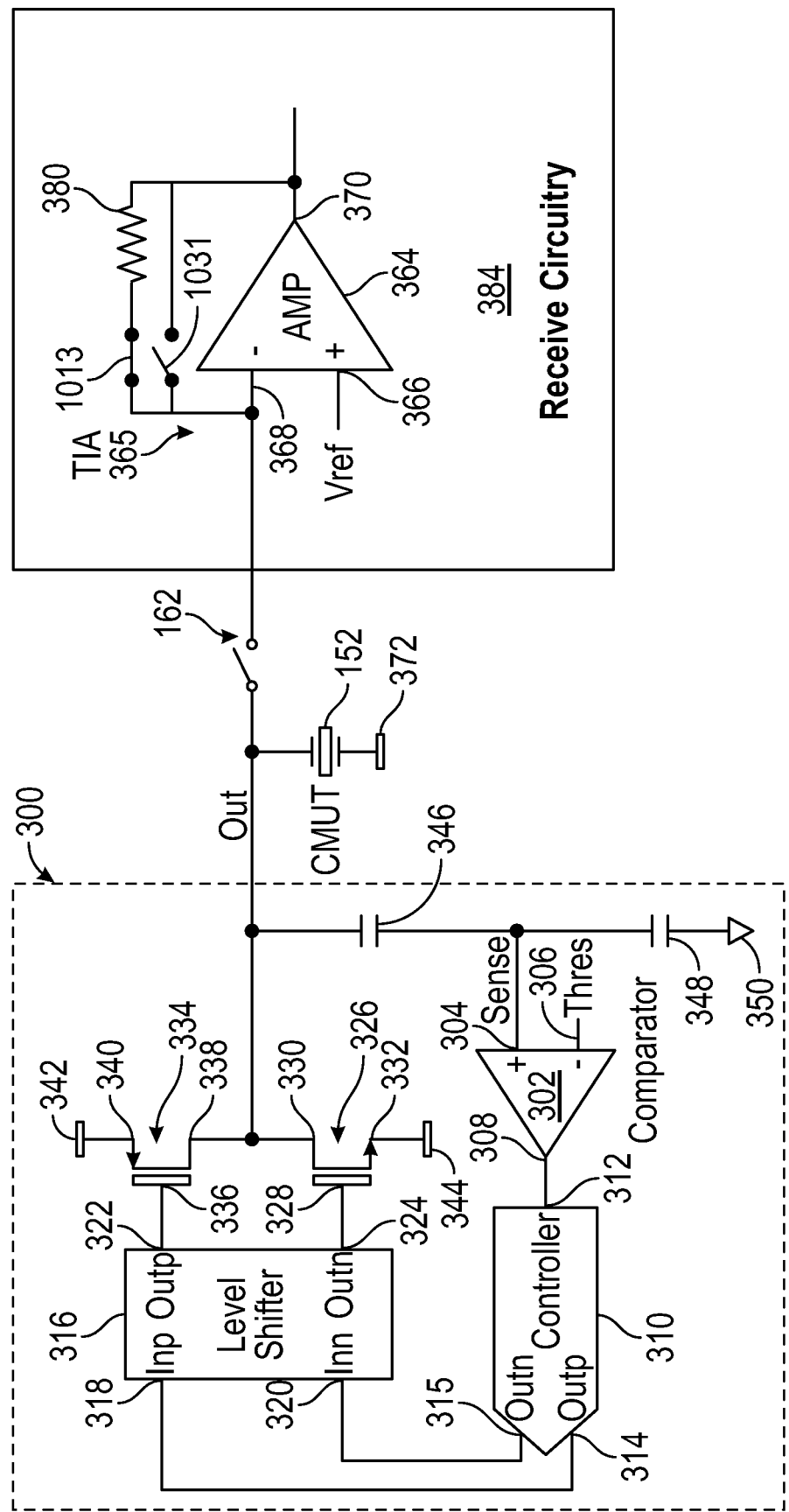
FIG. 3 is an example schematic diagram illustrating circuitry in an ultrasound system, in accordance with certain embodiments described herein.

Certain ultrasound devices include ultrasonic transducers, such as capacitive micromachined ultrasonic transducers (CMUTs), that are configured to convert a voltage pulse signal to an ultrasonic wave. To generate an ultrasonic wave of sufficient pressure to penetrate a human body, a pulser circuit may generate a high-voltage pulse signal and input that high-voltage pulse signal to a CMUT.

Certain ultrasound devices also include receive circuitry which may include amplifiers, filters, analog-to-digital converters, and digital processing circuits that are configured to receive, process, and output electronic signals produced by ultrasonic transducers in response to received ultrasonic waves. When there are multiple channels of receive circuitry, it may be helpful for the receive circuitry to operate at low voltages. For example, this may enable receive circuitry to achieve a small physical size in an integrated circuit, and may help to prevent the receive circuitry from generating too much heat. Ultrasound devices may therefore have high-voltage (HV) domains including, for example, pulsers, and a low-voltage (LV) domains including, for example, receive circuitry.

It may be helpful to test pulsers in integrated circuits. For example, testing may include:
1. Analyzing whether a pulser is working (e.g., whether it is pulsing)
2. When there are multiple pulsers in an ultrasound device, analyzing whether certain pulsers are working and certain pulsers are not working;
3. Analyzing what a pulser output waveform looks like, which may be especially helpful for multi-level pulsing and for imaging optimization;
4. When there are multiple pulsers in the ultrasound device, analyzing how uniform pulsed waveforms are among different pulsers;
5. Analyzing what the actual slew rate of a pulser is with different CMUT loads.

Certain methods of testing pulsers, such as measuring acoustic transmission power from the pulsers using lens reflection, may suffer from lens nonuniformity, and may not be capable of measuring the real pulser output waveform.

The inventors have recognized that one efficient approach for testing a pulser may be to route the output of the pulser to the ultrasound device's receive circuitry, which may already be configured to process electronic signals and output the electronic signals to an external device, where the signals can be analyzed. However, a challenge is that signals output by the pulser may be high-voltage while the receive circuitry may only be capable of handling low-voltage signals. The inventors have recognized that built-in self-test (BIST) integrated circuitry may be integrated onto the same substrate (e.g., a semiconductor substrate) that also includes integrated ultrasound circuitry, such as one or more pulsers, where the BIST circuitry may be configured to receive high-voltage signals from a pulser and attenuate the signal such that the signal may be processed and output by the receive circuitry. One approach, which may be considered a current-mode approach, includes converting the high-voltage pulser output signal to an attenuated current signal using a transconductance amplifier coupled between the pulser and the receive circuitry, and then using a transimpedance amplifier in the receive circuitry to convert the attenuated current signal to a low-voltage signal. Another approach, which may be considered a voltage-mode approach, includes converting the high-voltage pulser output signal to an attenuated voltage signal using one or more capacitor dividers in a capacitor network between the pulser and the receive circuitry.

It should be noted that in some embodiments, a pulser may already include attenuation circuitry (e.g., a capacitor divider) for attenuating the high-voltage pulser output signal to a mid-voltage pulser output. Feedback circuitry in the pulser that operates at a mid-voltage level (i.e., a level between the high-voltage level of the pulser output and the low-voltage levels of the receive circuitry) may then use the attenuated pulser output signal. Thus, the pulser may include both an HV domain and a mid-voltage (MV) domain. In such embodiments, in the current-mode approach, the BIST circuitry may convert the MV version of the pulser output signal to a current signal, and then the transimpedance amplifier may convert the current signal to a LV signal. In voltage mode, the BIST circuitry may convert the MV version of the pulser output signal to a LV signal.

The inventors have also recognized that such circuitry for BIST may also be used for characterizing a CMUT (e.g., characterizing its capacitance, collapse voltage, and/or stiction) and/or testing receive circuitry. For example, a transconductance amplifier in BIST circuitry may be used to generate a constant current and inject that current to an input terminal of a comparator in receive circuitry in the ultrasound device, where the input terminal of the comparator is electrically coupled to the CMUT. The constant current output from the transconductance amplifier may be integrated onto the CMUT to generate a ramp voltage. The comparator may compare the ramp voltage to the reference voltage, and the time it takes from the beginning of the ramp to when the ramp crosses the reference voltage may be used to compute the capacitance of the CMUT. If the capacitance of a CMUT is measured as a function of multiple bias voltage applied to the CMUT, the collapse voltage of the CMUT may be determined, or it may be determined whether the membrane of the CMUT is stuck to the substrate of the CMUT.

Measuring the collapse voltage may be helpful because the collapse voltage of a CMUT may change with time. Applying a bias voltage to the CMUT that is a particular offset voltage greater than the collapse voltage of the CMUTs may help to ensure that, as the collapse voltage of the CMUT changes, the value of the bias voltage applied to the CMUT minus the collapse voltage of the CMUT remains the same. This may help to keep the acoustic efficiency of the CMUT consistently optimized over time. When an ultrasound device includes an array of CMUTs that share one membrane, the collapse voltages of all the CMUTs in the array, or a subset thereof, may be measured and averaged, and a bias voltage may be applied to the CMUTs that is a particular offset voltage greater than the average of the collapse voltages of the CMUTs.

With regards to stiction, a CMUT membrane can get stuck on the substrate due to electrostatic force from charges trapped in the cavity, or from van der Waals forces between the membrane and the bottom of the cavity. Such stiction is detrimental to the operation of the CMUT. By restricting the motion of the membrane, stiction may cause a lower transmission pressure output as well as decreased reception sensitivity, such that resulting ultrasound images may be lower in quality (e.g., in terms of signal-to-noise ratio (SNR)). Also, in an array of CMUTs, stiction may cause non-uniformity in the array, since some CMUTs might be stuck while others may not. The pattern of stuck CMUTs may also not repeat. Asymmetry in the stiction profile may cause undesirable resonant modes. Non-uniformity and non-repeatability in the stiction profile may particularly negatively affect some imaging modes such as Doppler mode by introducing imaging artifacts. It may be helpful to measure how many CMUTs in an array are stuck and generate a notification when the number of stuck CMUTs exceeds a threshold. For example, the notification may notify a user that the ultrasound device should be replaced.

For testing receive circuitry, a pulser may generate a multi-level pulse voltage waveform (e.g., to mimic a sinewave test waveform) and the transconductance amplifier in the BIST circuitry may convert this voltage waveform to a current waveform and output this current waveform to the receive circuitry. This may be an accurate and controllable method for injecting a test waveform to the receive circuitry. Additionally, when multiple blocks of circuitry include transconductance amplifiers, this method may allow for uniformity in generation of waveforms and testing based on the waveforms across the different blocks. In some embodiments, for testing receive circuitry, current sources coupled through switches to a capacitor at the input of receive circuitry may be operated to charge or discharge the capacitor and thereby generate an increasing and/or decreasing ramp voltages at the input of the receive circuitry. This ramp voltage may be injected to the receive circuitry and used for testing the receive circuitry.

As referred to herein in the detailed description and claims, two elements being "coupled" should be understood to mean either directly coupled or that there may be intervening circuitry between the two elements.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

FIG. 1 is an example schematic diagram illustrating circuitry in an ultrasound system, in accordance with certain embodiments described herein. FIG. 1 includes a pulser 100, a capacitive micromachined ultrasonic transducer (CMUT) 152, a receive switch 162, and receive circuitry 184. The pulser 100 is coupled to the CMUT 152. The CMUT 152 is in series with the receive switch 162, which is coupled to the receive circuitry 184. The CMUT 152 is couplable to the receive circuitry 184 by closing the switch 162.

In operation, the pulser 100 may be configured to generate high-voltage pulses that are inputted to the CMUT 152 (during the "transmit phase"). The high-voltage pulses may cause the CMUT 152 to output ultrasonic waves. During the transmit phase, to prevent the high-voltage pulses from the pulser 100 from being inputted to the receive circuitry 184, which operates at low voltages, the receive switch 162 may be configured to be open. The CMUT 152 may be configured to receive reflected ultrasonic waves and convert these ultrasonic waves to electric currents (during the "receive phase"). The receive circuitry 184 may be configured to convert these electric currents to voltages that can be further processed by other circuitry in the receive circuitry 184. During the receive phase, to allow electric currents converted from received ultrasonic waves to be inputted to the receive circuitry 184, the receive switch 162 may be configured to be closed. The receive circuitry 184 may include further amplifiers, filters, analog-to-digital converters, and digital processing circuits that may be configured to receive, process, and output the electronic signals produced by the CMUT 152 in response to received ultrasonic waves.

FIGS. 3, 4, 8, 10, 14, 15, 16, 17, and 21 illustrate non-limiting examples of the circuitry of FIG. 1 in more detail. The below figures include three types of transistors: high-voltage (HV), mid-voltage (MV), and low-voltage (LV). FIG. 2 illustrates transistor symbols used for the three different types of transistors, in accordance with certain embodiments described herein. In some embodiments, the maximum operating voltage for HV transistors may be up to 80 V. For example, the maximum operating voltage may be 32 V or 55 V. In some embodiments, the maximum operating voltage for MV transistors may be up to 8 V. For example, the maximum operating voltage may be 8 V or 5 V. In some embodiments, the maximum operating voltage for LV transistors may be up to 3.3 V. For example, the maximum operating voltage may be 1.5 V or 1.1 V. The below figures also include three types of power supplies: HV, MV, and LV, where the voltage of the HV power supplies (or the absolute value of their voltage) is higher than the voltage of the MV power supplies (or the absolute value of their voltage), and the voltage of the MV power supplies (or the absolute value of their voltage) is higher than the voltage of the LV power supplies (or the absolute value of their voltage).

FIG. 3 is an example schematic diagram illustrating circuitry in an ultrasound system, in accordance with certain embodiments described herein. FIG. 3 includes a pulser 300 (which may be an example of the pulser 100), the capacitive micromachined ultrasonic transducer (CMUT) 152, the receive switch 162, and receive circuitry 384 (which may be an example of the receive circuitry 184). The pulser 300 includes a comparator 302, a controller 310, a level shifter 316, a HV n-type metal-oxide-semiconductor field effect transistor (nMOS) 326, a HV p-type metal-oxide-semiconductor field effect transistor (pMOS) 334, and a capacitor divider formed by two capacitors 346 and 348. The receive circuitry 384 includes an amplifier 364 and other circuitry not explicitly illustrated. As will be described further below, in some embodiments the amplifier 364 in the receive circuitry 384 is configurable as a transimpedance amplifier. In some embodiments, the amplifier 364 in the receive circuitry 384 is configurable as a comparator. In some embodiments, the amplifier 364 in the receive circuitry 384 is configurable as a unity-gain amplifier.

The comparator 302 has a positive input terminal 304, a negative input terminal 306, and an output terminal 308. The controller 310 has an input terminal 312, a positive output terminal 314, and a negative output terminal 315. The level shifter 316 has a positive input (inp) terminal 318, a negative input terminal (inn) 320, a positive output terminal (outp) 322, and a negative output terminal (outn) 324. The HV nMOS 326 has a gate terminal 328, a drain terminal 330, and a source terminal 332. The HV pMOS 334 has a gate terminal 336, a drain terminal 338, and a source terminal 340. The amplifier 364 has a positive input terminal 366, a negative input terminal 368, and an output terminal 370.

The positive input terminal 304 of the comparator 302 is coupled to a node Sense. The negative input terminal 306 of the comparator 302 is coupled to a node Thres. The output terminal 308 of the comparator 302 is coupled to the input terminal 312 of the controller 310. The positive output terminal 314 of the controller 310 is coupled to the positive input terminal 318 of the level shifter 316. The negative output terminal 315 of the controller 310 is coupled to the negative input terminal 320 of the level shifter 316. The negative output terminal 324 of the level shifter 316 is coupled to the gate terminal 328 of the HV nMOS 326. The positive output terminal 322 of the level shifter 316 is coupled to the gate terminal 336 of the HV pMOS 334. The drain terminal 330 of the HV nMOS 326 is coupled to the node Out. The source terminal 332 of the HV nMOS 326 is coupled to a HV negative power supply 344. The drain terminal 338 of the HV pMOS 334 is coupled to the node Out. The source terminal 340 of the HV pMOS 334 is coupled to a HV positive power supply 342. The capacitor 346 extends between the node Out and the node Sense. The capacitor 348 extends between the node Sense and ground 350.

The CMUT 152 is coupled between the node Out and a bias voltage 372. In particular, a bottom electrode of the CMUT 152 at its substrate may be coupled to the node Out and a membrane of the CMUT 152 may be coupled to the bias voltage 372, which may be referred to as $V_{BIAS}$. If Out is at a virtual ground, then the voltage applied to the CMUT 152 (i.e., between the membrane and the bottom electrode of the CMUT 152) may be $V_{BIAS}$. The receive switch 162 is coupled between the node Out and the negative input terminal 368 of the amplifier 364. The CMUT 152 is couplable to the input terminal of the receive circuitry 384 (in FIG. 3, to the negative input terminal 368 of the amplifier 364) by closing the receive switch 162.

A bias voltage Vref is coupled to the positive input terminal 366 of the amplifier 364. Vref may be generated by bias circuitry, such as a resistor divider in parallel with a bypass capacitor. A resistor 380 in series with a switch 1013 is coupled between the negative input terminal 368 of the amplifier 364 and the output terminal 370 of the amplifier 364. A switch 1031 is also coupled between the negative input terminal 368 of the amplifier 364 and the output terminal 370 of the amplifier 364. In FIG. 3, the switch 1013 is closed and the switch 1031 is open. This configuration, in which the resistor 380 is coupled in feedback configuration between the negative input terminal 368 of the amplifier 364 and the output terminal 370 of the amplifier 364 is referred to as the TIA 365.

In operation, the pulser 300 may be configured to generate high-voltage pulses at the node Out. The node Out is coupled to the CMUT 152, such that the high-voltage pulses at Out may cause the CMUT 152 to output ultrasonic waves. The pulser 300 may operate in a feedback configuration to output these high-voltage pulses. In particular, the capacitor divider consisting of the capacitors 346 and 348 may be configured to attenuate the output voltage of the pulser 300 at the node Out to a lower voltage at the node Sense. The capacitor divider may be configured to attenuate the high-voltage pulses in the HV domain to lower-voltage pulses in the MV domain appropriate for processing by the comparator 302 and the controller 310, which may operate at voltages in the MV domain.

The comparator 302 may be configured to compare the voltage at Sense to the voltage at the node Thres. As will be described further below, the voltage at the node Thres may be a threshold voltage. The comparator 302 may be configured to output a high voltage if Sense is greater than Thres and output a low voltage if Sense is less than Thres. The controller 310 may be configured to control the voltages inputted to the level shifter 316 based on the output voltage received from the comparator 302. For example, if the output voltage received from the comparator 302 is high (i.e., the voltage at Sense is greater than the voltage at Thres), then the controller 310 may be configured to output signals at the positive output terminal 314 and/or at the negative output terminal 315 configured to turn on the HV nMOS 326 and/or to turn off the HV pMOS 334. In this case, an electric current flowing from the node Out to the HV negative power supply 344 may discharge or negatively charge the node Out until the voltage at Sense is equal to (or within a threshold of) the voltage at Thres. As another example, if the output voltage received from the comparator 302 is low, then the controller 310 may be configured to output signals at the positive output terminal 314 and/or at the negative output terminal 315 configured to turn off the HV nMOS 326 and/or to turn on the HV pMOS 334. In this case, an electric current flowing from the HV positive power supply 342 may charge the node Out until the voltage at Sense is equal to (or within a threshold of) the voltage at Thres. As can be seen in FIG. 3, the output signals at the positive output terminal 314 and at the negative output terminal 315 of the controller 310 are not directly coupled to the HV nMOS 326 and the HV pMOS 334. This may be because the controller 310 may operate at voltages in the MV domain and the HV nMOS 326 and the HV pMOS may operate at voltages in the HV domain. Thus, the level shifter 316 may be configured to receive these output signals in the MV domain at its positive input terminal 318 and negative input terminal 320, and convert these signals to higher voltage signals in the HV domain at the positive output terminal 322 and the negative output terminal 324 appropriate for controlling the gate terminal 328 of the HV nMOS 326 and the gate terminal 336 of the HV pMOS 334. If the voltage at Sense equals the voltage at Thres, the comparator 302 may be turned off (e.g., by control logic not illustrated) until the voltage at Thres changes. For rail-to-rail two-level bipolar or unipolar pulsing, the feedback network formed by the comparator 302, the controller 310, the level shifter 316, and the capacitors 346 and 348 may not be used.

In addition to transmitting ultrasonic waves in response to receiving high-voltage pulses from the pulser 300 (during the "transmit phase"), the CMUT 152 may be configured to receive reflected ultrasonic waves and convert these ultrasonic waves to electric currents (during the "receive phase"). The TIA 365 may be configured to convert these electric currents to voltages that can be further processed by other circuitry in the receive circuitry 384. During the transmit phase, to prevent the high-voltage pulses from the pulser 300 from being inputted to the TIA 365, the receive switch 162 may be configured to be open. During the receive phase, to allow electric currents converted from received ultrasonic waves to be inputted to the TIA 365 (and specifically, to the negative input terminal 368 of the amplifier 364), the receive switch 162 may be configured to be closed.

With the resistor 380 coupled in feedback around its amplifier 364, the TIA 365 may be configured to convert the current received at the negative input terminal 368 of the amplifier 364 to a voltage at the output terminal 370 of the amplifier 364 with a gain equivalent (at least approximately) to the resistance of the resistor 380. The voltage at the output terminal 370 may be output to other circuitry in the receive circuitry 384, which may include, for example, circuitry for converting analog voltages to digital codes and for outputting the digital codes to an external device.

Figure 4:
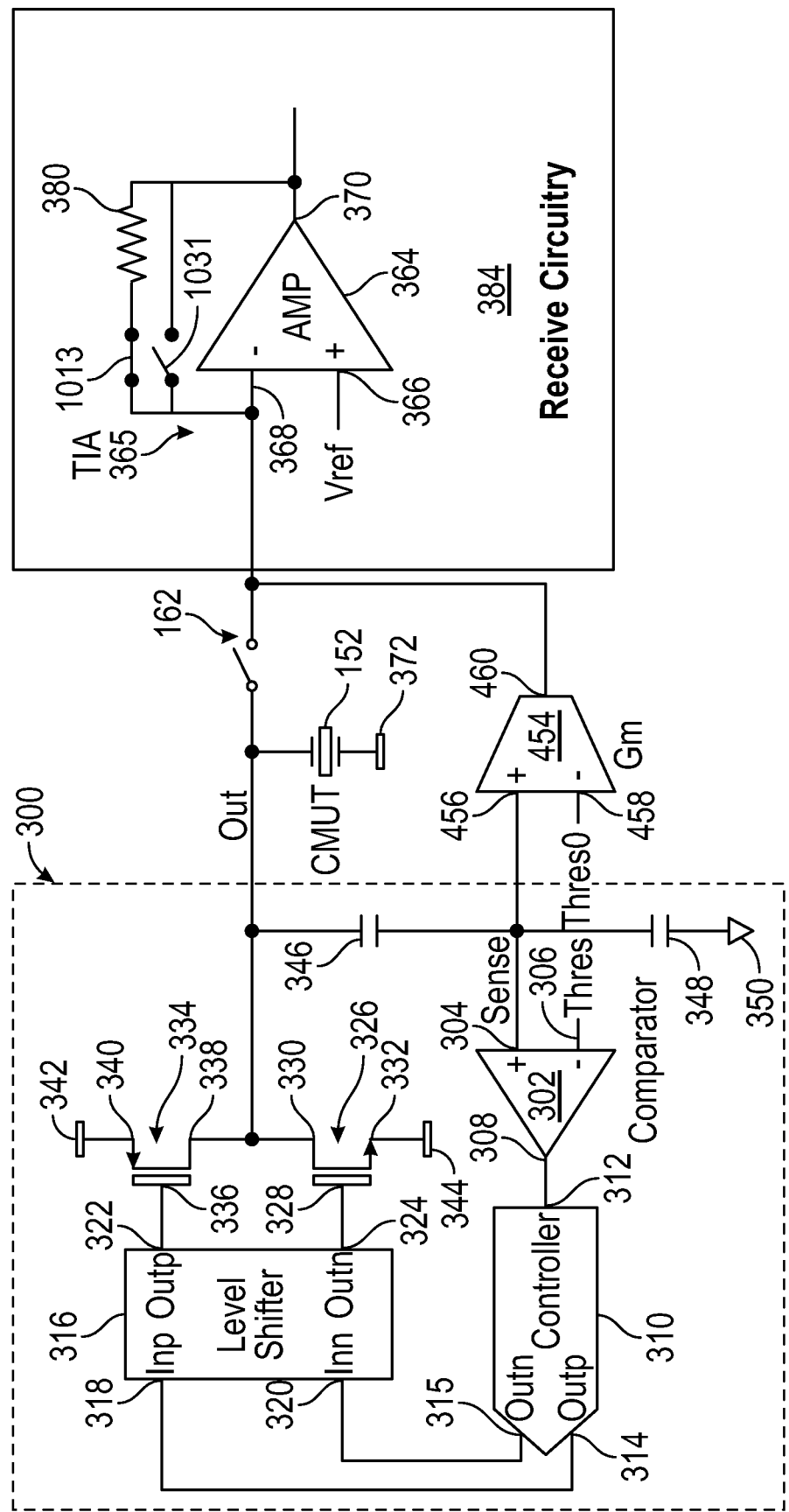
FIG. 4 is an example schematic diagram illustrating further circuitry in an ultrasound system, in accordance with certain embodiments described herein.

FIG. 4 is an example schematic diagram illustrating further circuitry in an ultrasound system, in accordance with certain embodiments described herein. FIG. 4 is the same as FIG. 3, but with the addition of a transconductance amplifier (Gm) 454 coupled between the pulser 300 and the receive circuitry 384. As described above, it may be helpful to analyze the output of the pulser 300 for testing purposes. While the receive circuitry 384 may be capable of converting analog voltages to digital codes and outputting the digital codes to an external device where they can be analyzed, it may not be feasible to directly connect the output of the pulser 300 to the receive circuitry 384 (e.g., to the TIA 365). The output of the pulser 300 may include pulses that are higher in voltage (e.g., in the HV domain) than the operating voltage of the receive circuitry 384 (e.g., in the LV domain). The inventors have recognized that, instead, the transconductance amplifier 454 may be included between the pulser 300 and the receive circuitry 384 (in particular, the TIA 365) for built-in self-testing (BIST). The transconductance amplifier 454 may be configured to convert the output of the pulser 300 (or an attenuated version of the output of the pulser 300) to an attenuated current signal that can be converted to a voltage signal by the TIA 365. For example, the transconductance amplifier may be configured to convert the HV output of the pulser 300, or an attenuated version of the pulser 300 output in the MV domain, to the LV domain. This LV analog signal may then be output to other circuitry in the receive circuitry 384, which may be configured to convert the analog voltage signal to a digital codes and output it to an external device, where it can be analyzed for testing purposes. In other words, the transconductance amplifier may be configured to process the output of the pulser 300 such that the receive circuitry 384 may be reused for testing. FIG. 4 may thus illustrate a configuration for testing of the pulser 300. As will be described further below, the transconductance amplifier 454 may be a linearized transconductance amplifier.

The transconductance amplifier 454 has a positive input terminal 456, a negative input terminal 458, and an output terminal 460. The positive input terminal 456 of the transconductance amplifier 454 is coupled to the node Sense. The negative input terminal 458 is coupled the node Thres0. The output terminal 460 of the transconductance amplifier 454 is coupled to the negative input terminal 368 of the amplifier 364. The amplifier 364, as in FIG. 3, is in the feedback (current-to-voltage conversion) configuration of the TIA 365. The transconductance amplifier 454 may be configured to receive the voltage pulses from the pulser 300 (after attenuation by the capacitor divider formed by the capacitors 346 and 348) and convert the difference between these voltage pulses and the voltage Thres0 at the negative input terminal 458 to a current at the output terminal 460. This current may then be input to the TIA 365 (in particular, to the negative input terminal 368 of the amplifier 364) for conversion to an analog voltage that may be digitally converted and outputted to an external device by the receive circuitry 384, and analyzed for testing purposes.

As described above, the transconductance amplifier 454 may be configured to convert the difference between the voltage pulses at Sense and the voltage Thres0 to a current. As will be described further below, the voltage Thres0 may be the middle voltage of the voltage pulses at Sense, such that subtracting Thres0 from the voltage at Sense may remove the DC component of the voltage pulses. If the DC component of the voltage pulses were not removed, the output current of the transconductance amplifier 454 may saturate the TIA 365.

Figure 5:
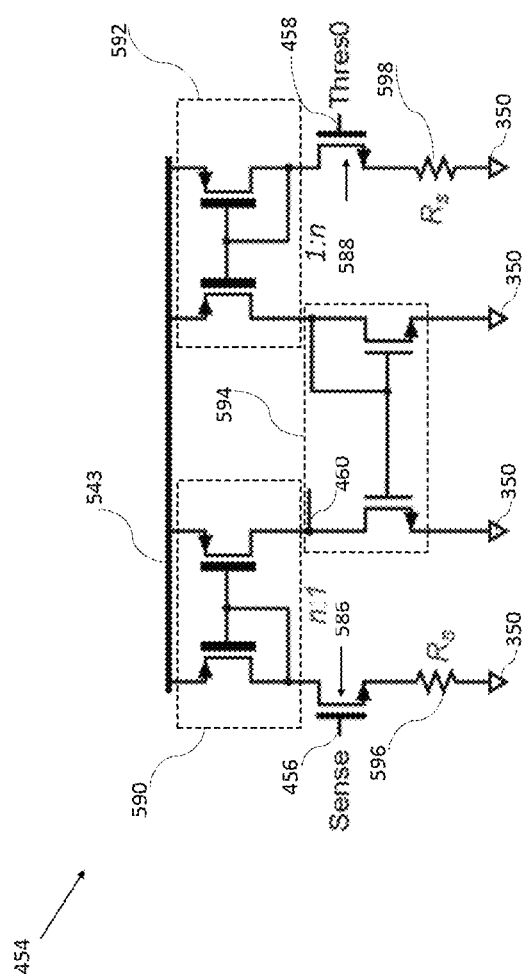
FIG. 5 is an example circuit diagram for a transconductance amplifier, in accordance with certain embodiments described herein.

FIG. 5 is an example circuit diagram for the transconductance amplifier 454, in accordance with certain embodiments described herein. The transconductance amplifier 454 includes a positive input MV transistor 586, a negative input MV transistor 588, a current mirror 590, a current mirror 592, a current mirror 594, a resistor 596, and a resistor 598. The gate of the positive input MV transistor 586, which is also the positive input terminal 456 of the transconductance amplifier 454, is coupled to Sense, the drain is coupled to the current mirror 590, and the source is coupled to the resistor 596. The gate of the negative input MV transistor 588, which is also the negative input terminal 458 of the transconductance amplifier 44, is coupled to Thres0, the drain is coupled to the current mirror 592, and the source is coupled the resistor 598. The current mirror 590 is coupled between the positive input MV transistor 586, the current mirror 594, and a MV positive power supply 543. The current mirror 592 is coupled between the negative input MV transistor 588, the current mirror 594, and the MV positive power supply 543. The current mirror 594 is coupled between the current mirror 590, the current mirror 592, and ground 350. The output terminal 460 of the transconductance amplifier 454 is taken from the node between the current mirror 590 and the current mirror 594 which, in turn, mirrors the current from current mirror 592. The current mirror 590 and the current mirror 592 include MV transistors. The current mirror 594 includes LV transistors. The resistance of the resistors 596 and 598 is referred to as $R_s$. While FIG. 5 illustrates one example circuit for the transconductance amplifier 454, it should be appreciated that other circuits may be used.

The transconductance amplifier 454 of FIG. 5 may be considered a source-degenerated linearized transconductance cell. "Linearized" may mean that the transconductance of the transconductance amplifier 454 is not dominated by the transconductance (gm) of the positive input MV transistor 586 and the negative input MV transistor 588, which may be the normal case for transconductance amplifiers. Rather, the transconductance of the transconductance amplifier 454 may be dominated by the resistance R s of the degenerated resistors 596 and 598. This may be helpful because gm may not be constant versus different operating voltages/currents, which may introduce non-linearity. In contrast, when the transconductance is dominated by the resistance $R_s$, the transconductance may be relatively consistent with different voltage/current ranges, thus resulting in better linearity. Such a linearized transconductance amplifier may not be used in other applications because, to obtain a high voltage gain, gm should dominate the transconductance. Here, however, the linearity in conversion between current and voltage may be more important than high gain.

The conversion ratio between the pulser output voltage at the node Out and the transconductance amplifier 454 output at the output terminal 360 may be $$A_{capdiv} = \frac{R_{TIA}}{n \cdot R_s},$$

where $A_{capdiv}$ is the division ratio of the capacitor divider formed by the capacitors 346 and 348, and the current mirror ratio of the current mirrors 590 and 592 is n:1. In particular, for every n parallel transistors (not illustrated explicitly) in the current mirrors 590 and 592 that have their drains connected to their gates, there may be 1 transistor that does not have its drain connected to its gate. To achieve a desired value for the denominator in the expression $$\frac{R_{TIA}}{n \cdot R_s},$$

the current mirror ratio n:1 may be selected (in other words, the number of parallel transistors may be selected) such that the resistance $R_s$ may be a sufficiently low value to achieve an acceptably low required physical area for the resistors 596 and 598. In some embodiments, the ratio $$\frac{R_{TIA}}{n \cdot R_s}$$

may be approximately equal to or between 1/20 and 1. In some embodiments, $A_{capdiv}$ may be approximately equal to or between 1/32 and 1/4 (e.g., 1/8).

Figure 6:
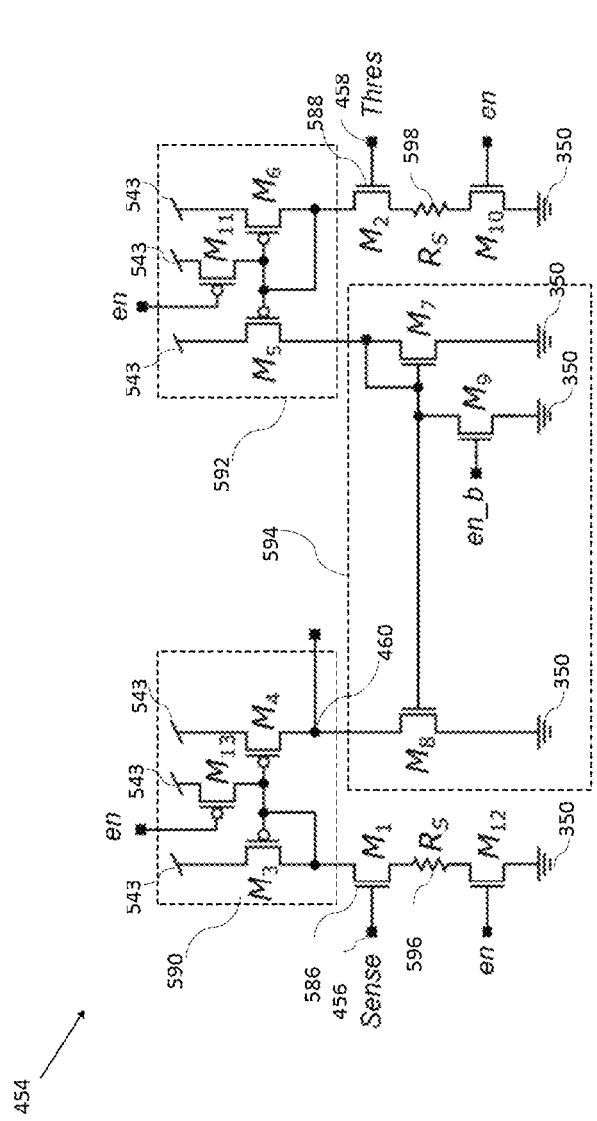
FIG. 6 is a circuit diagram of a non-limiting example of the transconductance amplifier of FIG. 5, in accordance with certain embodiments described herein.

FIG. 6 is a circuit diagram of a non-limiting example of the transconductance amplifier 454, in accordance with certain embodiments described herein. In particular, FIG. 6 illustrates circuitry, in particular transistors M9, M10, M11, M12, and M13, with which the circuitry illustrated in FIG. 5 may be augmented to enable turning on and off of the transconductance amplifier 454. For example, for testing circuitry in the ultrasound device (e.g., for testing the pulser 300 or for characterizing the CMUT 152), the transconductance amplifier 454 may be turned on. For using the ultrasound device for normal imaging, the transconductance amplifier 454 may be turned off while the pulser 300 and the receive circuitry 384 remain on.

In operation, to turn off the transconductance amplifier 454, the signal en may be switched low and the signal en_b may be switched high. This may cause:
1. The transistor M9 to turn on, thereby pulling the drain of M9 low to the ground 350 and turning off the transistors M8 and M9 in the current mirror 594;
2. The transistor M10 to turn off, thereby disabling current flow in its branch of the transconductance amplifier 454;
3. The transistor M11 to turn on, thereby pulling the drain of M11 up to the voltage of the MV power supply 543, and turning off the transistors M5 and M6 in the current mirror 592;
4. The transistor M12 to turn off, thereby disabling current flow in its branch of the transconductance amplifier 454;
5. The transistor M13 to turn on, thereby pulling the drain of M13 up to the voltage of the MV power supply 543, and turning off the transistors M3 and M4 in the current mirror 590.

In operation, to turn on the transconductance amplifier 454, the signal en may be switched high and the signal en_b may be switched low. This may cause:
1. The transistor M9 to turn off;
2. The transistor M10 to turn on, thereby enabling current flow in its branch of the transconductance amplifier 454;
3. The transistor M11 to turn off;
4. The transistor M12 to turn on, thereby enabling current flow in its branch of the transconductance amplifier 454;
5. The transistor M13 to turn off.

In some embodiments, the enable signals for M9, M10, and M11 may be independent of the enable signals for M12 and M13. For example, the enable signals for M9, M10, and M11 may be switched low while the enabled signals for M12 and M13 may be switched high. This may allow conversion of the voltage at Sense to a current without DC subtraction of the voltage at Thres.

Figure 7:
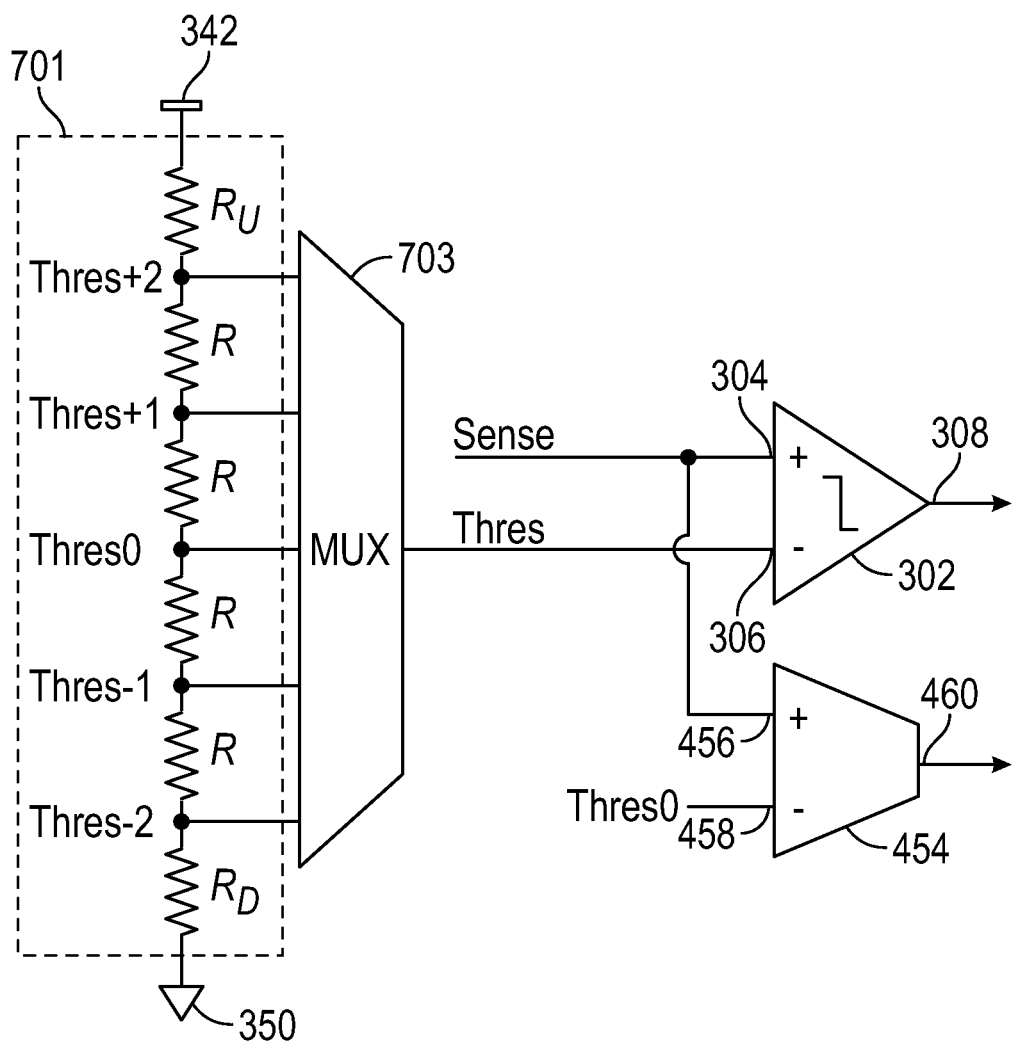
FIG. 7 is an example circuit diagram for further circuitry in an ultrasound system, in accordance with certain embodiments described herein.

FIG. 7 is an example circuit diagram for further circuitry in an ultrasound system, in accordance with certain embodiments described herein. FIG. 7 illustrates a configuration which may be used for testing of the pulser 300 in conjunction with the configuration illustrated in FIG. 4. FIG. 7 illustrates the comparator 302, the transconductance amplifier 454, a resistor ladder 701, and a multiplexer 703. The resistor ladder 701 includes multiple resistors coupled in a ladder fashion between the HV positive power supply 342 and ground 350 such that the resistors form multiple resistor dividers for generating multiple voltages at the nodes Thres+2, Thres+1, Thres0, Thres−1, Thres−2. Both the transconductance amplifier 454 and the pulser 300 (in particular, the comparator 302) are configured to receive, as inputs, voltages from the resistor ladder 701. The multiplexer 703 may accept these voltages at its input terminals and select, based on a control signal not illustrated, one of the voltages at is output terminal (referred to as the node Thres), which is coupled to the negative input terminal 306 of the comparator. In some embodiments, the resistor ladder 701 may include more resistors for generating more voltage options. In some embodiments, the resistor ladder 701 may include fewer resistors for generating fewer voltage options. The number of voltage options generated may depend on the requirements for the multi-level pulsing (e.g., how many voltage levels are desired).

As described above, the pulser 300 may operate by using feedback to cause the voltage at the node Sense to be equivalent to, or within a threshold of, the selected threshold voltage at the node Thres. The voltage at Sense is an attenuated version of the voltage at the node Out, which is the output of the pulser 300. Thus, in operation, selection of one of the voltages generated by the resistor ladder 701 may control the output of the pulser 30.

The voltage Thres0 is coupled to the negative input terminal 458 of the transconductance amplifier 454. As can be seen in FIG. 7, the voltage Thres0 is the middle voltage of the voltages generated by the resistor ladder 701, and due to feedback of the pulser 300, Thres0 may be middle voltage of the voltage at Sense. As described above, subtracting Thres0 from the voltage at Sense by the transconductance amplifier 454 may remove the DC component of the voltage pulses at Sense. If the DC component of the voltage pulses were not removed, the output of the transconductance amplifier 454 may saturate the TIA 365 (not illustrated in FIG. 7).

Figure 8:
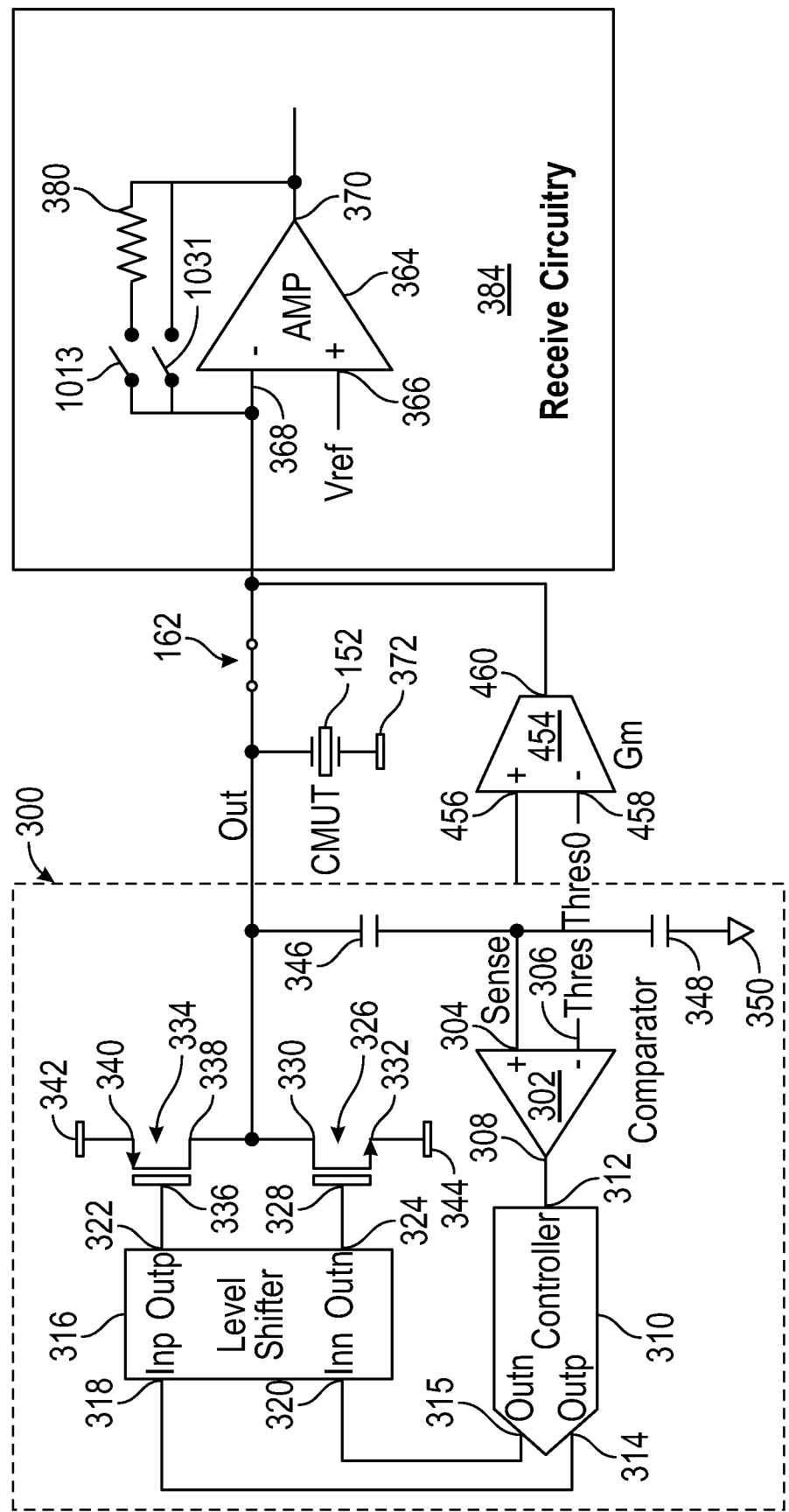
FIG. 8 is an example schematic diagram illustrating further circuitry in an ultrasound system, in accordance with certain embodiments described herein.

FIG. 8 is an example schematic diagram illustrating further circuitry in an ultrasound system, in accordance with certain embodiments described herein. FIG. 8 is the same as FIG. 4, except that:

1. The voltage Thres (i.e., the same voltage inputted to negative input terminal 306 of the comparator 302) is inputted to the positive input terminal 456 of the transconductance amplifier 454;
2. The switch 1013 and the switch 1031 are open, such that there is an open circuit between the negative input terminal 368 and the output terminal 370 of the amplifier 364. In other words, the amplifier 364 is in open-loop configuration and may operate as a comparator (rather than as a TIA);
3. The receive switch 162 is closed.

FIG. 8 illustrates a non-limiting example of a configuration for characterizing the CMUT 152 (e.g., characterizing its capacitance, collapse voltage, and/or stiction). In such a configuration, the pulser 300 may be kept off, such that it does not output any high-voltage signals. The voltage at Thres may be kept constant, such that the voltage difference between Thres and Thres0 that is inputted to the transconductance amplifier 454 is constant, and the output current from the transconductance amplifier 454 is constant. The constant current output from the transconductance amplifier 454 may be integrated onto the CMUT 152 to generate a ramp voltage at the negative input terminal 368 of the amplifier 364. The amplifier 364, operating as a comparator, may compare the ramp voltage to the reference voltage (referred to as Vref) at the positive input terminal 366 of the amplifier 364. When the ramp voltage crosses Vref, the output voltage of the amplifier 364 may switch from high to low or from low to high. If the ramp begins at the voltage of an LV positive power supply (referred to as VDDA) and proceeds to ground 350, or if the ramp begins at ground 350 and proceeds to VDDA, the configuration of FIG. 8 may accordingly be used to time how long it takes from the beginning of the ramp to when the ramp cross Vref. The capacitance of the CMUT 152 may be computed as $$C = \frac{I_{ramp} \times T_{ramp}}{VDDA - Vref},$$

where $I_{ramp}$ is the constant current outputted by the transconductance amplifier 454 and $T_{ramp}$ is the time it takes from the beginning of the ramp to when the ramp cross Vref. In some embodiments, two ramps may be used, one during current sourcing and one during current sinking, such that one ramp proceeds from VDDA to ground 350 (during current sinking) and one proceeds from ground 350 to VDDA (during current sourcing), and the average of the $T_{ramp}$ measured for each ramp may be used to compute C. In some embodiments, multiple repeated measurements of the time for ramp voltages to cross the reference voltage may be performed during current sourcing, and these multiple measurements of time may be averaged. Additionally, multiple repeated measurements of the time for ramp voltages to cross the reference voltage may be performed during current sinking, and these multiple measurements of time may be averaged. The two averaged results, one result for current sourcing and one for current sinking, may then be averaged together. Alternatively, the multiple measurements from current sourcing and from current sinking may be averaged together. It should be appreciated that in some embodiments, measuring the time for a ramp voltage to cross the reference voltage during current sourcing may be performed prior to measuring the time for a ramp voltage to cross a reference voltage during current sinking, while in some embodiments, measuring the time for a ramp voltage to cross the reference voltage during current sinking may be performed prior to measuring the time for a ramp voltage to cross the reference voltage during current sourcing.

In some embodiments, characterizing the CMUT 152 may include characterizing the collapse voltage of the CMUT 152. Characterizing the collapse voltage of the CMUT 152 may include applying multiple different bias voltage values $V_{BIAS}$ to the CMUT 152. The bias voltage $V_{BIAS}$ applied to the CMUT may be measured between the membrane of the CMUT 152 and the bottom electrode at the substrate of the CMUT 152. If the bottom electrode at the substrate of the CMUT 152 is at virtual ground, then applying $V_{BIAS}$ to the CMUT may be accomplished by applying $V_{BIAS}$ to the membrane. For each value of $V_{BIAS}$, the capacitance of the CMUT 152 may be computed as described above to produce a C vs. $V_{BIAS}$ curve. A discontinuity may be observed in this curve when there is contact between the membrane and the substrate of the CMUT 152. If the C vs. $V_{BIAS}$ curve was generated by increasing the value of $V_{BIAS}$, then the value of $V_{BIAS}$ at which this contact occurs (i.e., the value of $V_{BIAS}$ at which the discontinuity occurs) may be the collapse voltage of the CMUT 152. A discontinuity may be detected in the C vs. $V_{BIAS}$ curve by calculating the first and/or second derivative of the curve.

In some embodiments, characterizing the CMUT 152 may include characterizing whether the membrane of the CMUT 152 is stuck to the substrate of the CMUT 152. In some embodiments, a C vs. $V_{BIAS}$ curve may be generated as described above, and if no discontinuity is detected in this curve, this may mean that the membrane of the CMUT 152 is stuck to the substrate of the CMUT 152. This may be because, for the entire range of $V_{BIAS}$ values, the membrane is collapsed.

In some embodiments, applying $V_{BIAS}$ to the membrane of the CMUT 152 may include routing the voltage $V_{BIAS}$ from circuitry in the ultrasound device but external to the substrate on which the CMUT 152 is disposed, through a routing network, and to the membrane of the CMUT 152. It may be helpful to wait for the voltage at the membrane to settle to $V_{BIAS}$ after charging or discharging the routing network.

Figure 9:
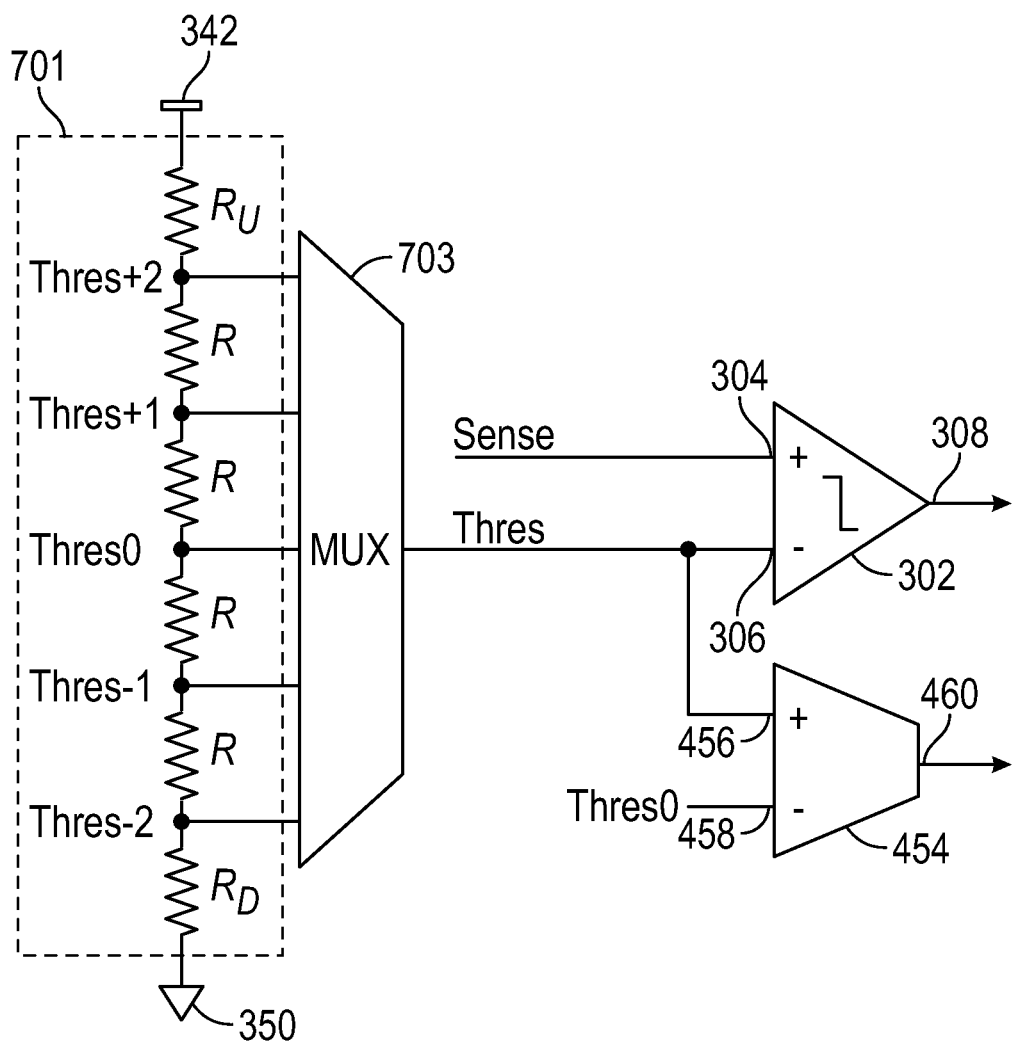
FIG. 9 is an example circuit diagram for further circuitry in an ultrasound system, in accordance with certain embodiments described herein.

FIG. 9 is an example circuit diagram for further circuitry in an ultrasound system, in accordance with certain embodiments described herein. FIG. 9 illustrates a non-limiting example of a configuration for characterizing the CMUT 152 in conjunction with the configuration illustrated in FIG.

8. FIG. 9 is the same as FIG. 7, except that in FIG. 9, the voltage Thres is inputted to the positive input terminal 456 of the transconductance amplifier 454.

Figure 10:
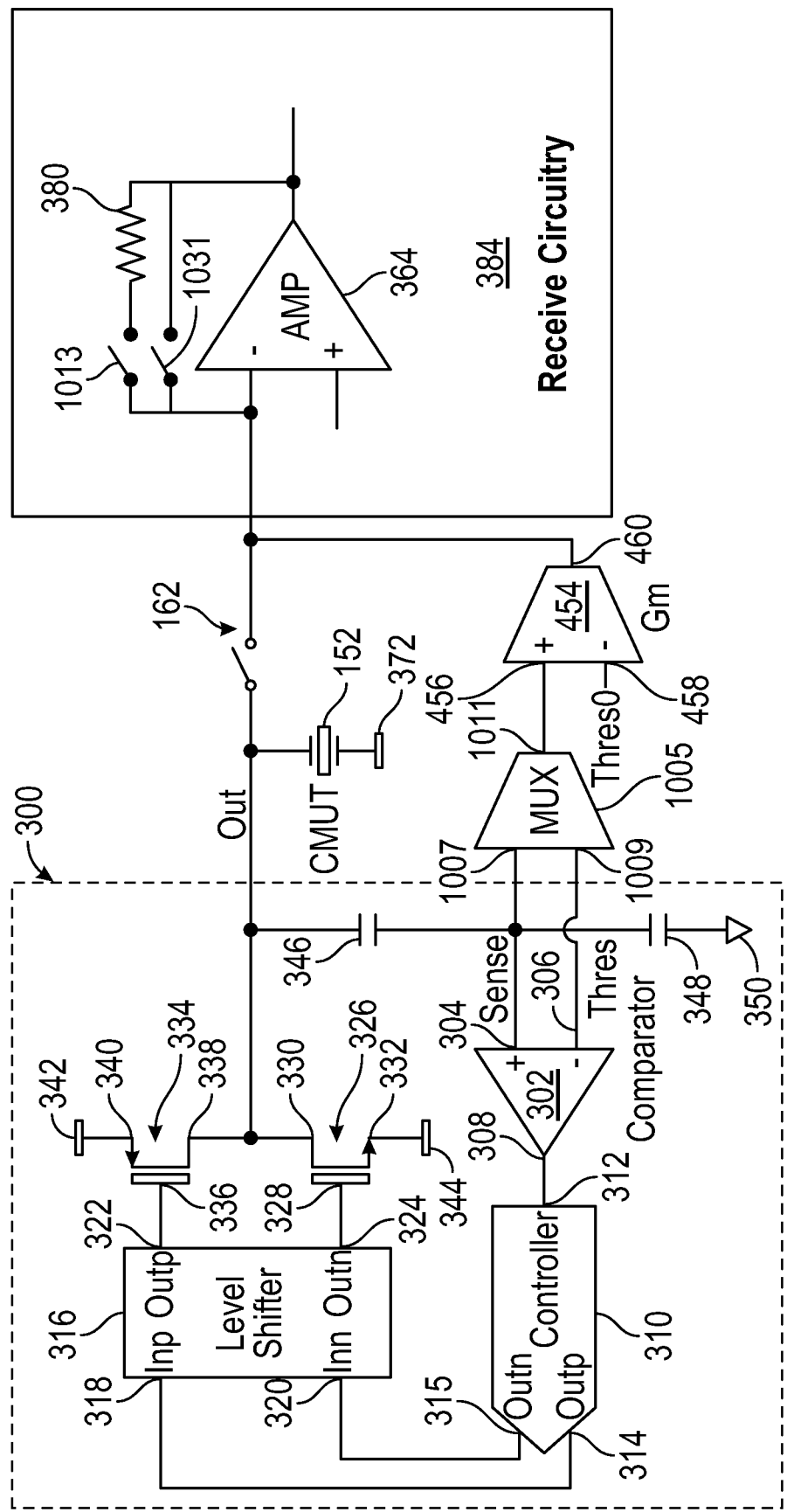
FIG. 10 is an example schematic diagram illustrating circuitry in an ultrasound system, in accordance with certain embodiments described herein.

FIG. 10 is an example schematic diagram illustrating circuitry in an ultrasound system, in accordance with certain embodiments described herein. FIG. 10 is the same as FIG. 4, except that FIG. 10 includes a multiplexer 1005. The multiplexer 1005 includes a first input terminal 1007, a second input terminal 1009, and an output terminal 1011. The first input terminal 1007 is coupled to the node Sense. The second input terminal 1009 is coupled to the node Thres. The output terminal 1011 is coupled to the positive input terminal 456 of the transconductance amplifier 454.

The circuit of FIG. 10 may be used either for testing the pulser 300, as described with reference to FIG. 4, or for characterizing the CMUT 152, as described with reference to FIG. 8. In operation, for testing the pulser 300, a control signal for the multiplexer 1005 (not illustrated in the figure) may control the multiplexer 1005 to select the voltage at the first input terminal 1007 (i.e., the voltage at the node Sense) for outputting at the output terminal 1011. Additionally, the switch 1013 may be closed and the switch 1031 may be open, such that the amplifier 364 is in the close-loop, feedback configuration of the TIA 365. Thus, the circuit may be equivalent to the circuit of FIG. 4. For characterizing the CMUT 152, a control signal for the multiplexer 1005 (not illustrated in the figure) may control the multiplexer 1005 to select the voltage at the second input terminal 1009 (i.e., the voltage at the node Thres) for outputting at the output terminal 1011. Additionally, the switch 1013 and the switch 1031 may be open, such that the amplifier 364 is in open-loop, comparator configuration, and the receive switch 162 may be closed. Thus, the circuit may be equivalent to the circuit of FIG. 8.

Figure 11:
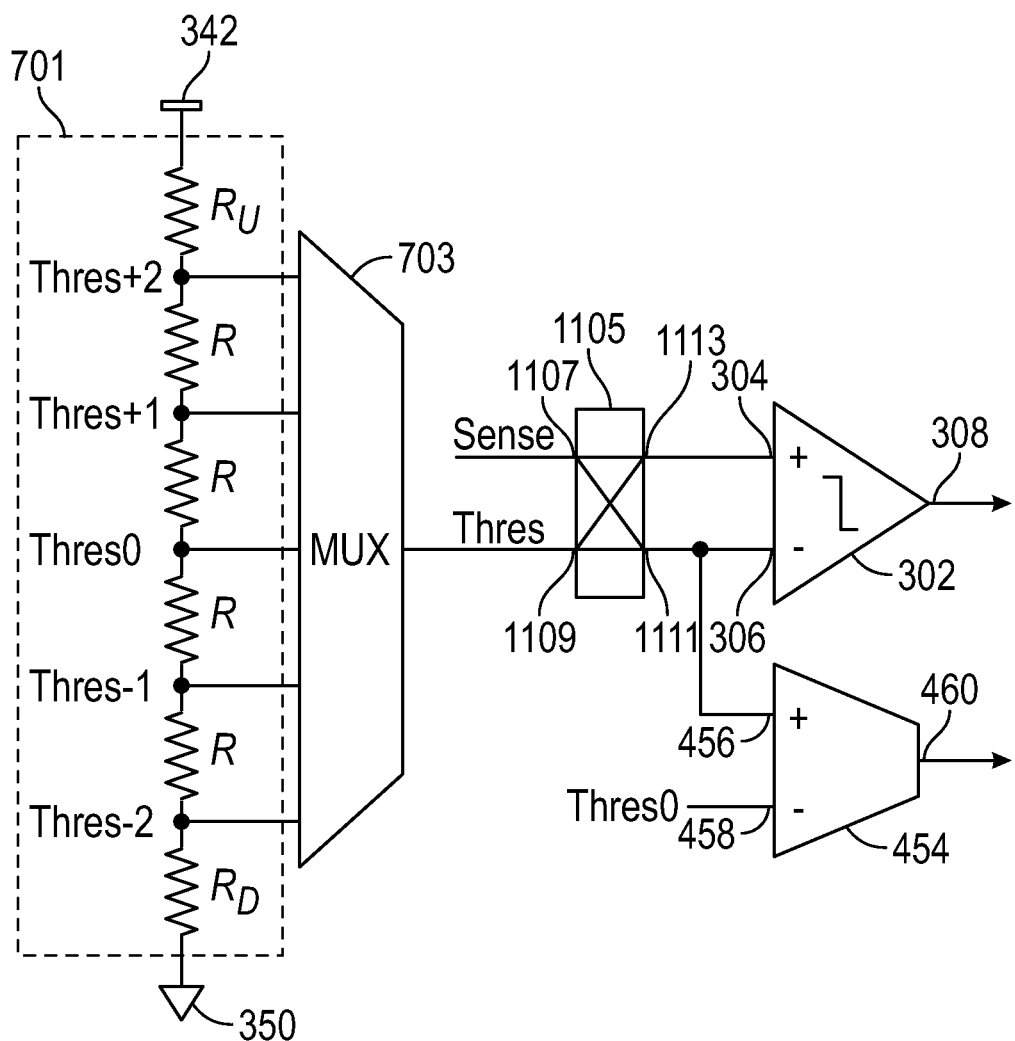
FIG. 11 is an example circuit diagram for further circuitry in an ultrasound system, in accordance with certain embodiments described herein.

FIG. 11 is an example circuit diagram for further circuitry in an ultrasound system, in accordance with certain embodiments described herein. FIG. 11 is the same as FIG. 7, except that FIG. 11 includes a chopper switch 1105. The chopper switch 1105 includes a first input terminal 1107, a second input terminal 1109, a first output terminal 1111, and a second output terminal 1113. The first input terminal 1107 is coupled to Sense. The second input terminal 1109 is coupled to Thres. The first output terminal 1111 is coupled to the positive input terminal 456 of the transconductance amplifier 456. The second output terminal 1113 is coupled to the positive input terminal 304 of the comparator 302.

The circuit of FIG. 11 may be used either for testing the pulser 300, as described with reference to FIG. 7, or for characterizing the CMUT 152, as described with reference to FIG. 9. In operation, for testing the pulser 300, a control signal for the chopper switch 1105 (not illustrated in the figure) may control the chopper switch 1105 to select the voltage at the first input terminal 1107 (i.e., at the node Sense) for outputting at the first output terminal 1111. Thus, the circuit may be equivalent to the circuit of FIG. 7. For characterizing the CMUT 152, the control signal for the chopper switch 1105 (not illustrated in the figure) may control the chopper switch 1105 to select the voltage at the second input terminal 1109 (i.e., the voltage at the node Thres) for outputting at the first output terminal 1111. Thus, the circuit may be equivalent to the circuit of FIG. 9.

Additionally, in operation, for normal transmission of pulses using the pulser 300, a control signal for the chopper switch 1105 (not illustrated in the figure) may control the chopper switch 1105 to select the voltage at the first input terminal 1107 (i.e., the voltage at the node Sense) for outputting at the second output terminal 1113 and to select the voltage at the second input terminal 1109 (i.e., the voltage at the node Thres) for outputting at the first output terminal 1111. Alternatively, the control signal for the chopper switch 1105 may control the chopper switch 1105 to select the voltage at the first input terminal 1107 (i.e., the voltage at the node Sense) for outputting at the first output terminal 1111 and to select the voltage at the second input terminal 1109 (i.e., the voltage at the node Thres) for outputting at the second output terminal 1113. Thus, the circuit may control the polarity of pulses generated by the pulser 300, and the comparator 302 may only need to detect crossings in one direction (e.g., rising or falling).

Figure 12:
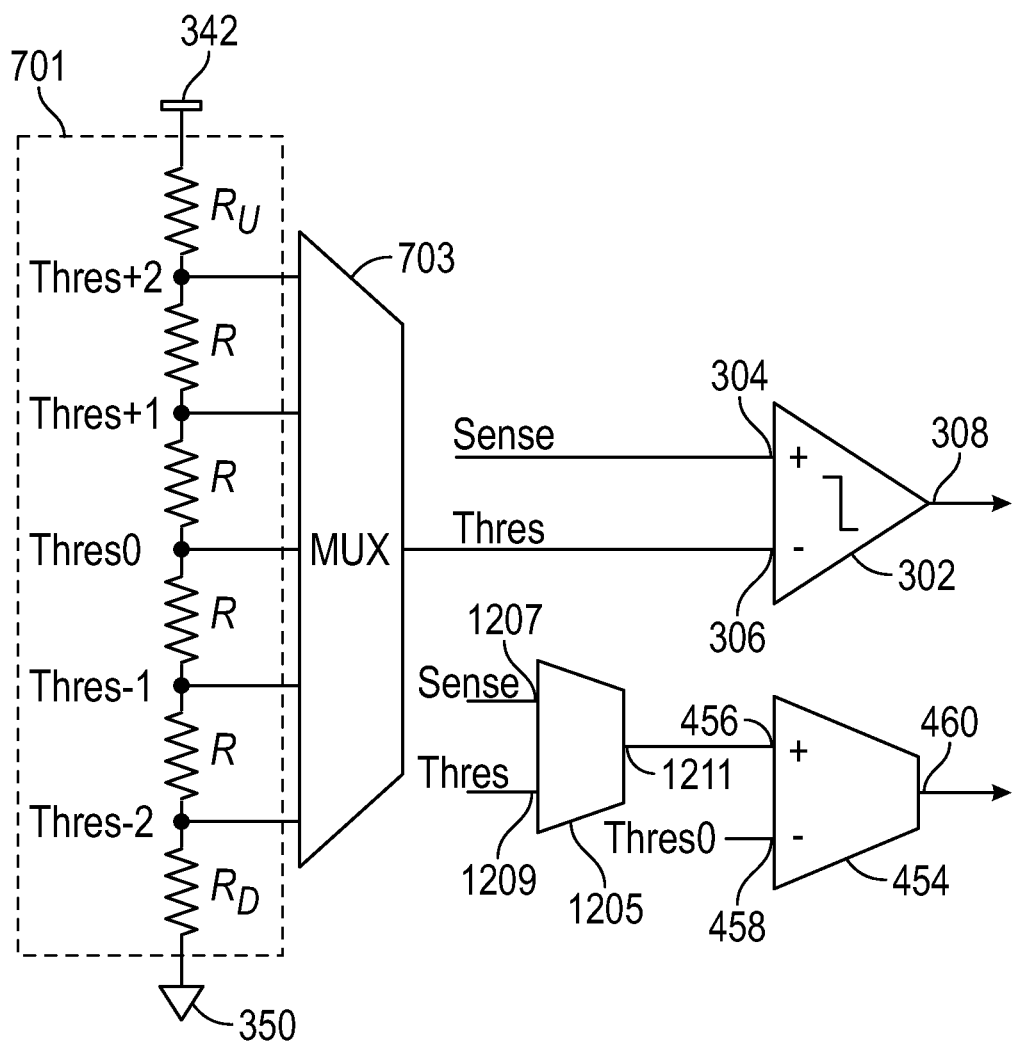
FIG. 12 is an example circuit diagram for further circuitry in an ultrasound system, in accordance with certain embodiments described herein.

FIG. 12 is an example circuit diagram for further circuitry in an ultrasound system, in accordance with certain embodiments described herein. FIG. 12 is the same as FIG. 7, except that FIG. 12 includes a multiplexer 1205. The multiplexer 1205 includes a first input terminal 1207, a second input terminal 1209, and an output terminal 1211. The first input terminal 1207 is coupled to Sense. The second input terminal 1209 is coupled to Thres. The output terminal 1211 is coupled to the positive input terminal 456 of the transconductance amplifier 456. Sense is also coupled to the first input terminal 304 of the comparator 302 and Thres is also coupled to the second input terminal 306 of the comparator 302.

The circuit of FIG. 12 may be used either for testing the pulser 300, as described with reference to FIG. 7, or for characterizing the CMUT 152, as described with reference to FIG. 9. In operation, for testing the pulser 300, a control signal for the multiplexer 1205 (not illustrated in the figure) may control the multiplexer 1205 to select the voltage at the first input terminal 1207 (i.e., at the node Sense) for outputting at the output terminal 1111. Thus, the circuit may be equivalent to the circuit of FIG. 7. For characterizing the CMUT 152, the control signal for the multiplexer 1205 (not illustrated in the figure) may control the multiplexer 1205 to select the voltage at the second input terminal 1209 (i.e., the voltage at the node Thres) for outputting at the output terminal 1211. Thus, the circuit may be equivalent to the circuit of FIG. 9.

For normal transmission of pulses using the pulser 300, the comparator 302 may be capable of detecting crossings in both directions (e.g., rising and falling) which may enable bipolar operation of the pulser 300.

Figure 13:
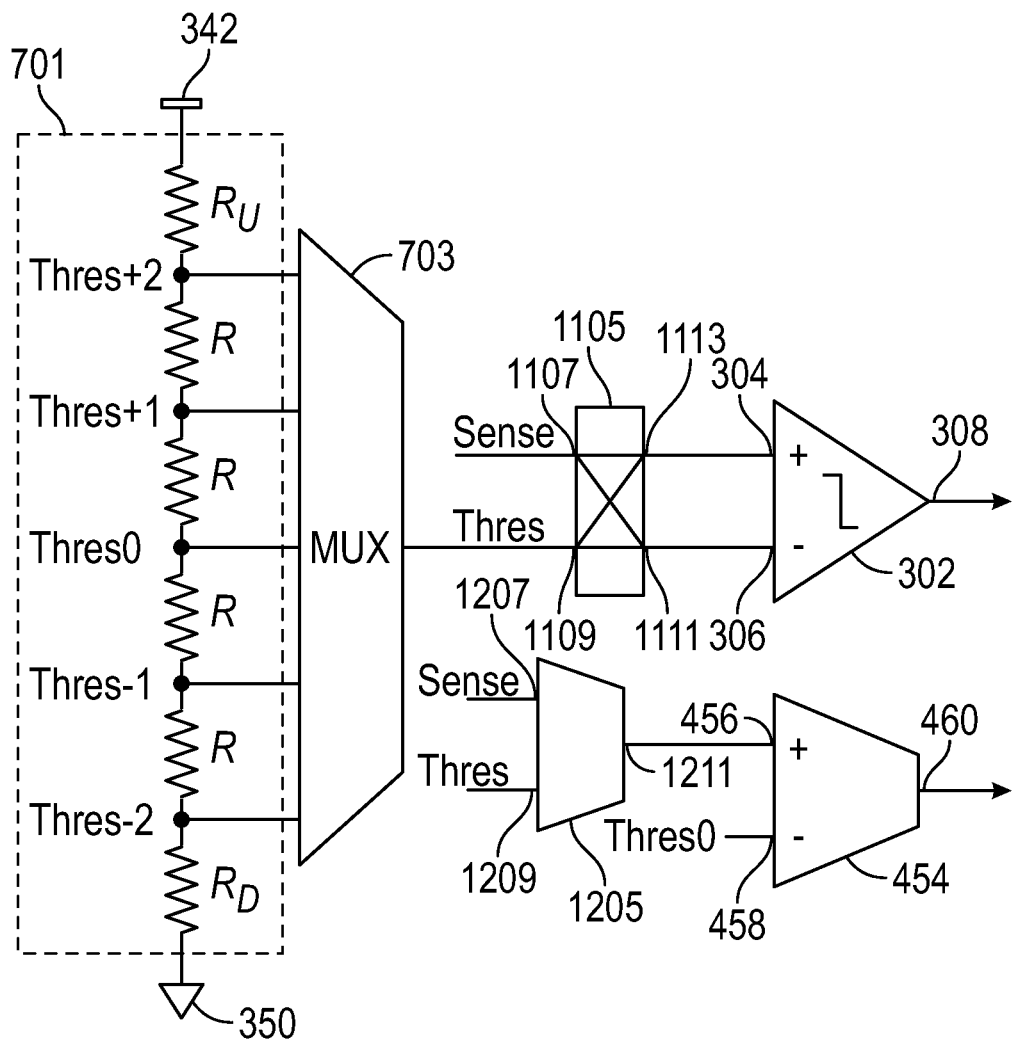
FIG. 13 is an example circuit diagram for further circuitry in an ultrasound system, in accordance with certain embodiments described herein.

FIG. 13 is an example circuit diagram for further circuitry in an ultrasound system, in accordance with certain embodiments described herein. FIG. 13 is the same as FIG. 7, except that FIG. 13 includes the chopper switch 1105 and the multiplexer 1205. The first input terminal 1107 of the chopper switch 1105 is coupled to Sense, the second input terminal 1109 is coupled to Thres, and the output terminal 1211 is coupled to the positive input terminal 456 of the transconductance amplifier 456. The first input terminal 1207 of the multiplexer 1205 is coupled to Sense. The second input terminal 1209 is coupled to Thres. The output terminal 1211 is coupled to the positive input terminal 456 of the transconductance amplifier 456. Further description of the use of the multiplexer 1205 for BIST may be found with reference to FIG. 12. Further description of the use of the chopper switch 1105 for controlling polarity of the pulser 300 may be found with reference to FIG. 11.

It should be appreciated from the foregoing discussion that the circuitry illustrated in FIGS. 4-13 may be used both for built-in self-testing (BIST) of the pulser 300 and characterizing the CMUT 152. Table 1 summarizes configurations for built-in self-testing (BIST) of the pulser 300 and characterizing of the CMUT 152:

TABLE 1

Summary of configurations for testing the pulser 300 and characterizing the CMUT 152.

| Mode | Input voltage of transconductance amplifier 454 | Amplifier 364 Configuration | Current injected to amplifier 364 |
|---|---|---|---|
| Testing Pulser 300 | $V_{Sense} - V_{Thres0}$ | Closed-Loop (TIA) | $\dfrac{V_{Sense} - V_{Thres0}}{n \cdot R_s}$ |
| Characterizing CMUT 152 | $V_{Thres} - V_{Thres0}$ | Open-Loop (Comparator) | $\dfrac{V_{Thres} - V_{Thres0}}{n \cdot R_s}$ |

Figure 14:
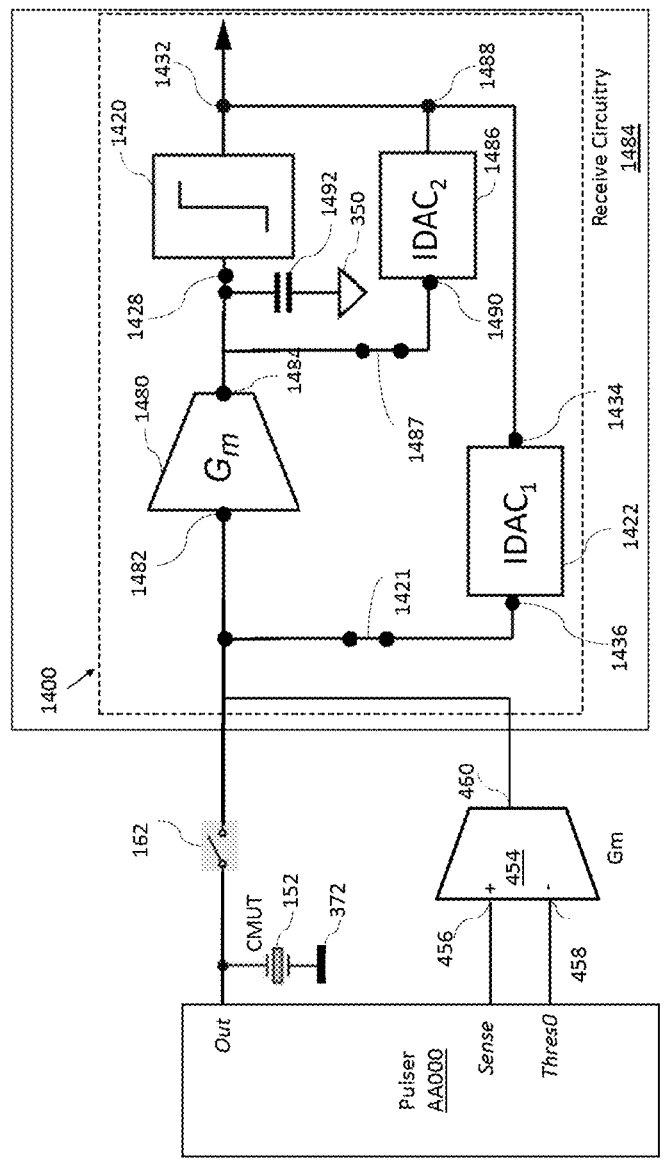
FIG. 14 is an example schematic diagram illustrating circuitry in an ultrasound system, in accordance with certain embodiments described herein.

FIG. 14 is an example schematic diagram illustrating circuitry in an ultrasound system, in accordance with certain embodiments described herein. FIG. 14 is a simplified version of FIG. 4, except that FIG. 14 includes receive circuitry 1484 instead of the receive circuitry 384. The receive circuitry 1484 (which may be an example of the receive circuitry 184) is configurable as a delta-sigma analog-to-digital converter (ADC) 1400. Briefly, the delta-sigma ADC 1400 may be considered a second-order delta-sigma ADC that includes two feedback loops. In operation, during normal imaging, the receive switch 162 may be closed, and the delta-sigma ADC 1400 may integrate and then quantize current output from the CMUT 152 to produce a digital logic level Dout. $D_{OUT}$ may be a pulse stream in which the frequency of pulses may be proportional to the current inputted to the delta-sigma ADC 1400. This frequency may be enforced by the feedback loops of the delta-sigma ADC 1400.

The delta-sigma ADC 1400 includes a transconductance amplifier 1480, a capacitor 1492, a voltage quantizer 1420, a current digital-to-analog converter (DAC) 1422, a current digital-to-analog converter (DAC) 1486, a switch 1487, and a switch 1421. The transconductance amplifier 1480 has an input terminal 1482 and an output terminal 1484. The voltage quantizer 1420 has an input terminal 1428 and an output terminal 1432. The current DAC 1486 has an input terminal 1488 and an output terminal 1490. The current DAC 1422 has an input terminal 1434 and an output terminal 1436.

In the configuration of FIG. 14, the input terminal 1482 of the transconductance amplifier 1480, the output terminal 1436 of the current DAC 1422, and the output terminal 460 of the transconductance amplifier 454 are coupled together. (The output terminal 1436 of the current DAC 1422 is coupled to this node through the closed switch 1421.) The output terminal 1484 of the transconductance amplifier 1480, the output terminal 1490 of the current DAC 1486, a terminal of the capacitor 1492, and the input terminal 1428 of the voltage quantizer 1420 are coupled together. (The output terminal 1490 of the current DAC 1486 is coupled to this node through the closed switch 1487.) The other terminal of the capacitor 1492 is coupled to ground 1450. The output terminal 1432 of the voltage quantizer 1420, the input terminal 1488 of the current DAC 1486, and the input terminal 1434 of the current DAC 1422 are coupled together. Further aspects of such delta-signal ADCs for converting current output of CMUTs are described in U.S. patent application Ser. No. 16/443,931 titled "APPARATUSES INCLUDING A CAPACITIVE MICROMACHINED ULTRASONIC TRANSDUCER DIRECTLY COUPLED TO AN ANALOG-TO-DIGITAL CONVERTER," filed on Jun. 18, 2019, and published on Oct. 3, 2019, as US-2019-0299251-A1 (and assigned to the assignee of the instant application), which is incorporated by reference herein in its entirety.

FIG. 14 illustrates a non-limiting example of a configuration for testing of the pulser 300. In operation, parasitic capacitance at the node at the input terminal 1482 of the transconductance amplifier 1480 may integrate the current output from the transconductance amplifier 454 (which may be a transformed version of the HV output of the pulser 300) into a voltage prior to conversion of this voltage back into a current by the transconductance amplifier 1480. The capacitor 1492 may integrate this current into a voltage that may then be quantized by the voltage quantizer 1420 to produce the digital output Dout. The output Dout of the delta-sigma ADC 1400 may be output by other circuitry in the receive circuitry 1484 to an external device for analysis of the operation of the pulser 300. The capacitance at the node at the input terminal 1482 of the transconductance amplifier 1480 may be lower than when the switch 162 is closed and the capacitance of the CMUT 152 is added to the parasitic capacitance at this node. Thus, the stability and linearity of the delta-sigma ADC 1400 may be degraded. It may be helpful for the transconductance amplifier 454's output current to be attenuated further to compensate for the loss in stability and linearity by reducing the signal swing.

Figure 15:
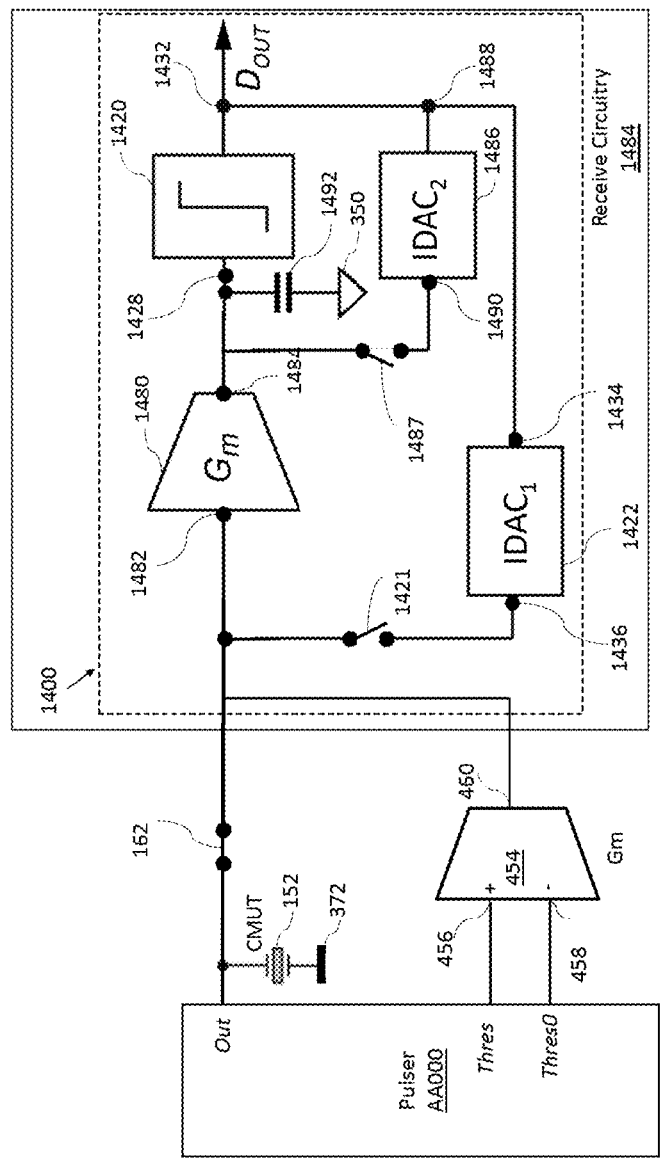
FIG. 15 is an example schematic diagram illustrating circuitry in an ultrasound system, in accordance with certain embodiments described herein.

FIG. 15 is an example schematic diagram illustrating circuitry in an ultrasound system, in accordance with certain embodiments described herein. FIG. 15 is the same as FIG. 14, with the following exceptions:

1. The positive input terminal of the transconductance amplifier 454 is coupled to Thres;
2. The switch 162 is closed;
3. The switch 1421 and the switch 1487 are open.

FIG. 15 illustrates a non-limiting example of a configuration for characterizing the CMUT 152 (e.g., characterizing its capacitance, collapse voltage, and/or stiction). In such a configuration, the pulser 300 may be kept off, such that it does not output any high-voltage signals. The voltage at Thres may be kept constant, such that the voltage difference between Thres and Thres0 that is inputted to the transconductance amplifier 454 is constant, and the output current from the transconductance amplifier 454 is constant. The constant current output from the transconductance amplifier 454 may be integrated onto the CMUT 152 to generate a ramp voltage at the input terminal 382 of the transconductance amplifier 1480. The transconductance amplifier 1480 may convert this voltage to a current. The capacitor 1492 may integrate this current into a voltage. The quantizer 1420, operating as a comparator, may compare the ramp voltage to a reference voltage (referred to as Vref, not illustrated). When the ramp voltage crosses Vref, the output voltage of the amplifier 364 may switch from high to low or from low to high. If the ramp begins at the voltage of an LV positive power supply (referred to as VDDA) and proceeds to ground 350, or if the ramp begins at ground 350 and proceeds to VDDA, the configuration of FIG. 8 may accordingly be used to time how long it takes from the beginning of the ramp to when the ramp cross Vref. The capacitance of the CMUT 152 may be computed as $$C = \frac{I_{ramp} \times T_{ramp}}{VDDA - Vref},$$

where $I_{ramp}$ ramp is the constant current outputted by the transconductance amplifier 454 and $T_{ramp}$ is the time it takes from the beginning of the ramp to when the ramp cross Vref. In some embodiments, two ramps may be used, one during current sourcing and one during current sinking, such that one ramp proceeds from VDDA to ground 350 (during current sinking) and one proceeds from ground 350 to VDDA (during current sourcing), and the average of the $T_{ramp}$ measured for each ramp may be used to compute C. In some embodiments, multiple repeated measurements of the time for ramp voltages to cross the reference voltage may be performed during current sourcing, and these multiple measurements of time may be averaged. Additionally, multiple repeated measurements of the time for ramp voltages to cross the reference voltage may be performed during current sinking, and these multiple measurements of time may be averaged. The two averaged results, one result for current sourcing and one for current sinking, may then be averaged together. Alternatively, the multiple measurements from current sourcing and from current sinking may be averaged together. It should be appreciated that in some embodiments, measuring the time for a ramp voltage to cross the reference voltage during current sourcing may be performed prior to measuring the time for a ramp voltage to cross a reference voltage during current sinking, while in some embodiments, measuring the time for a ramp voltage to cross the reference voltage during current sinking may be performed prior to measuring the time for a ramp voltage to cross the reference voltage during current sourcing.

In some embodiments, characterizing the CMUT 152 may include characterizing the collapse voltage of the CMUT 152. Characterizing the collapse voltage of the CMUT 152 may include applying multiple different bias voltage values $V_{BIAS}$ to the CMUT 152. The bias voltage $V_{BIAS}$ applied to the CMUT may be measured between the membrane of the CMUT 152 and the bottom electrode at the substrate of the CMUT 152. If the bottom electrode at the substrate of the CMUT 152 is at virtual ground, then applying $V_{BIAS}$ to the CMUT may be accomplished by applying $V_{BIAS}$ to the membrane. For each value of $V_{BIAS}$, the capacitance of the CMUT 152 may be computed as described above to produce a C vs. $V_{BIAS}$ curve. A discontinuity may be detected in this curve when there is contact between the membrane and the substrate of the CMUT 152. If the C vs. $V_{BIAS}$ curve was generated by increasing the value of $V_{BIAS}$, then the value of $V_{BIAS}$ at which this contact occurs (i.e., the value of $V_{BIAS}$ at which the discontinuity occurs) may be the collapse voltage of the CMUT 152. A discontinuity may be detected in the C vs. $V_{BIAS}$ curve by calculating the first and/or second derivative of the curve.

In some embodiments, characterizing the CMUT 152 may include characterizing whether the membrane of the CMUT 152 is stuck to the substrate of the CMUT 152. A C vs. $V_{BIAS}$ curve may be generated as described above, and if no discontinuity is detected in the curve, this may mean that the membrane of the CMUT 152 is stuck to the substrate of the CMUT 152. This may be because, for the entire range of $V_{BIAS}$ values, the membrane is collapsed.

In some embodiments, applying $V_{BIAS}$ to the membrane of the CMUT 152 may include routing the voltage $V_{BIAS}$ from circuitry in the ultrasound device but external to the substrate on which the CMUT 152 is disposed, through a routing network, and to the membrane of the CMUT 152. It may be helpful to wait for the voltage at the membrane to settle to $V_{BIAS}$ after charging or discharging the routing network.

In some embodiments, the transconductance amplifier 454 may be used (e.g., using the configuration of FIG. 4 or 14) to inject a waveform to receive circuitry (e.g., the receive circuitry 384 or 1484 or any of the other receive circuitry described herein) for testing of the receive circuitry. In operation, the pulser 300 may generate a multi-level pulse voltage waveform (e.g., to mimic a sinewave test waveform), an attenuated version of this voltage waveform may be generated at Sense, the transconductance amplifier 454 may convert this voltage waveform to a current waveform and output this current waveform to the receive circuitry. This may be an accurate and controllable method for injecting a test waveform to the receive circuitry. Additionally, when multiple blocks of circuitry include transconductance amplifiers 454, this method may allow for uniformity in generation of waveforms and testing based on the waveforms across the different blocks.

Figure 16A:
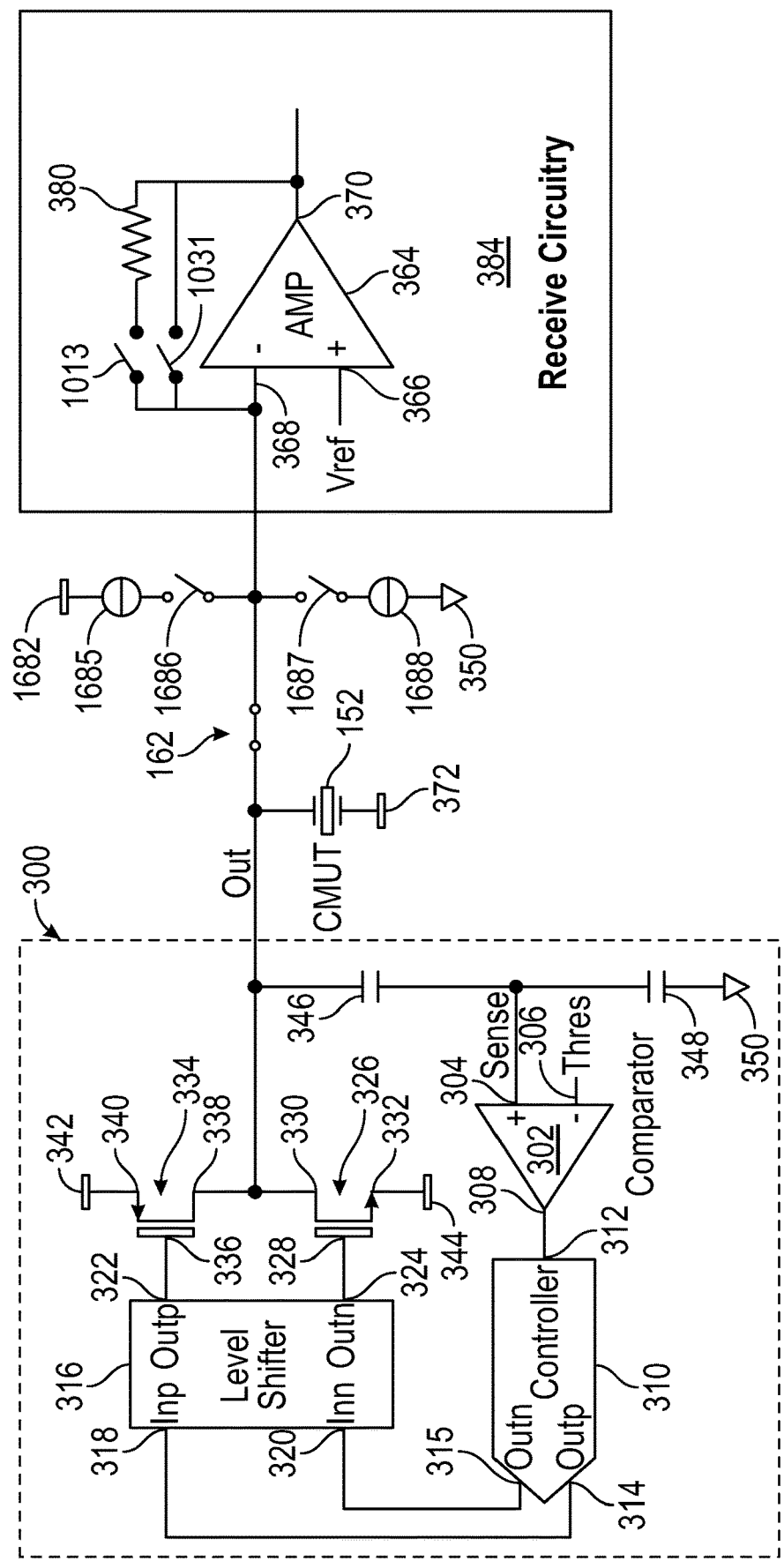
FIG. 16A is an example schematic diagram illustrating circuitry in an ultrasound system, in accordance with certain embodiments described herein.

FIG. 16A is an example schematic diagram illustrating circuitry in an ultrasound system, in accordance with certain embodiments described herein. FIG. 16A is the same as FIG. 8, except that the receive switch 162 is closed, and FIG. 16A includes a current source 1685, a switch 1686, a switch 1687, and a current source 1688 and lacks the transconductance amplifier 454. The switch 1013 and the switch 1031 are open, such that the amplifier 364 may operate as a comparator. (While FIG. 16A illustrates the receive circuitry 384, alternatively, the receive circuitry 1484 may be used.) The current source 1685, which it should be appreciated is distinct from the CMUT, is in series with the switch 1686 and is coupled between a LV power supply 382 and the negative input terminal 368 of the amplifier 364 (which is coupled, through the receive switch 162 to the node Out). The current source 1688 is in series with the switch 1687 and is coupled between the negative input terminal 368 of the amplifier 364 and ground 350. The current source 1685 is couplable to the input terminal of the receive circuitry 384 (in the example of FIG. 16A, to the negative input terminal 368 of the amplifier 364) by closing the switch 1686 and the current source 1688 is couplable to the input terminal of the receive circuitry 384 by closing the switch 1687. The current source 1685 may be configured to supply current to the input terminal of the receive circuitry 384 and the current source 1688 may be configured to sink current from the input terminal of the receive circuitry 384.

The circuit of FIG. 16A may be used for characterizing the CMUT 152 (e.g., characterizing its capacitance, collapse voltage, and/or stiction). In operation, the switch 1686 may be closed and the switch 1687 may be opened, such that the current source 1685 supplies a constant current to the node Out, charging or discharging the CMUT 152 (depending on the polarity of its membrane voltage) and generating an increasing ramp voltage at the node Out. Alternatively or additionally, the switch 1687 may be closed and the switch 1685 may be opened, such that the current source 1688 sinks a constant current from the node Out, charging or discharging the CMUT 152 (depending on the polarity of its membrane voltage) and generating a decreasing ramp voltage at the node Out. The amplifier 364, operating as a comparator, may compare the ramp voltage to the reference voltage (referred to as Vref) at the positive input terminal 366 of the amplifier 364. When the ramp voltage crosses Vref, the output voltage of the amplifier 364 may switch from high to low or from low to high. If the ramp begins at the voltage of the LV positive power supply 1682 (referred to as VDDA) and proceeds to ground 350 (i.e., the switch 1686 is closed), or if the ramp begins at ground 350 and proceeds to VDDA (i.e., the switch 1687 is closed), the configuration of FIG. 16A may accordingly be used to measure the time it takes from the beginning of the ramp to when the ramp cross Vref. The capacitance of the CMUT 152 may be computed as $$C = \frac{I_{ramp} \times T_{ramp}}{VDDA - Vref},$$

where $I_{ramp}$ is the constant current outputted by the current sources 1685 and/or 1688, and $T_{ramp}$ is the time it takes from the beginning of the ramp to when the ramp cross Vref. In some embodiments, two ramps may be used, one during current sourcing and one during current sinking, such that one ramp proceeds from VDDA to ground 350 (during current sinking) and one proceeds from ground 350 to VDDA (during current sourcing), and the average of the $T_{ramp}$ measured for each ramp may be used to compute C. In some embodiments, multiple repeated measurements of the time for ramp voltages to cross the reference voltage may be performed during current sourcing, and these multiple measurements of time may be averaged. Additionally, multiple repeated measurements of the time for ramp voltages to cross the reference voltage may be performed during current sinking, and these multiple measurements of time may be averaged. The two averaged results, one result for current sourcing and one for current sinking, may then be averaged together. Alternatively, the multiple measurements from current sourcing and from current sinking may be averaged together. It should be appreciated that in some embodiments, measuring the time for a ramp voltage to cross the reference voltage during current sourcing may be performed prior to measuring the time for a ramp voltage to cross a reference voltage during current sinking, while in some embodiments, measuring the time for a ramp voltage to cross the reference voltage during current sinking may be performed prior to measuring the time for a ramp voltage to cross the reference voltage during current sourcing.

In some embodiments, characterizing the CMUT 152 may include characterizing the collapse voltage of the CMUT 152. Characterizing the collapse voltage of the CMUT 152 may include applying multiple different bias voltage values $V_{BIAS}$ to the CMUT 152. The bias voltage $V_{BIAS}$ applied to the CMUT may be measured between the membrane of the CMUT 152 and the bottom electrode at the substrate of the CMUT 152. If the bottom electrode at the substrate of the CMUT 152 is at virtual ground, then applying $V_{BIAS}$ to the CMUT may be accomplished by applying $V_{BIAS}$ to the membrane. For each value of $V_{BIAS}$, the capacitance of the CMUT 152 may be computed as described above to produce a C vs. $V_{BIAS}$ curve. A discontinuity may be detected in this curve when there is contact between the membrane and the substrate of the CMUT 152. If the C vs. $V_{BIAS}$ curve was generated by increasing the value of $V_{BIAS}$, then the value of $V_{BIAS}$ at which this contact occurs (i.e., the value of $V_{BIAS}$ at which the discontinuity occurs) may be the collapse voltage of the CMUT 152. A discontinuity may be detected in the C vs. $V_{BIAS}$ curve by calculating the first and/or second derivative of the curve.

In some embodiments, characterizing the CMUT 152 may include characterizing whether the membrane of the CMUT 152 is stuck to the substrate of the CMUT 152. A C vs. $V_{BIAS}$ curve may be generated as described above, and if no discontinuity is detected in the curve (e.g., using a first and/or second derivative as described above), this may mean that the membrane of the CMUT 152 is stuck to the substrate of the CMUT 152. This may be because, for the entire range of $V_{BIAS}$ values, the membrane is collapsed.

In some embodiments, applying $V_{BIAS}$ to the membrane of the CMUT 152 may include routing the voltage $V_{BIAS}$ from circuitry in the ultrasound device but external to the substrate on which the CMUT 152 is disposed, through a routing network, and to the membrane of the CMUT 152. It may be helpful to wait for the voltage at the membrane to settle to $V_{BIAS}$ after charging or discharging the routing network.

Figure 16B:
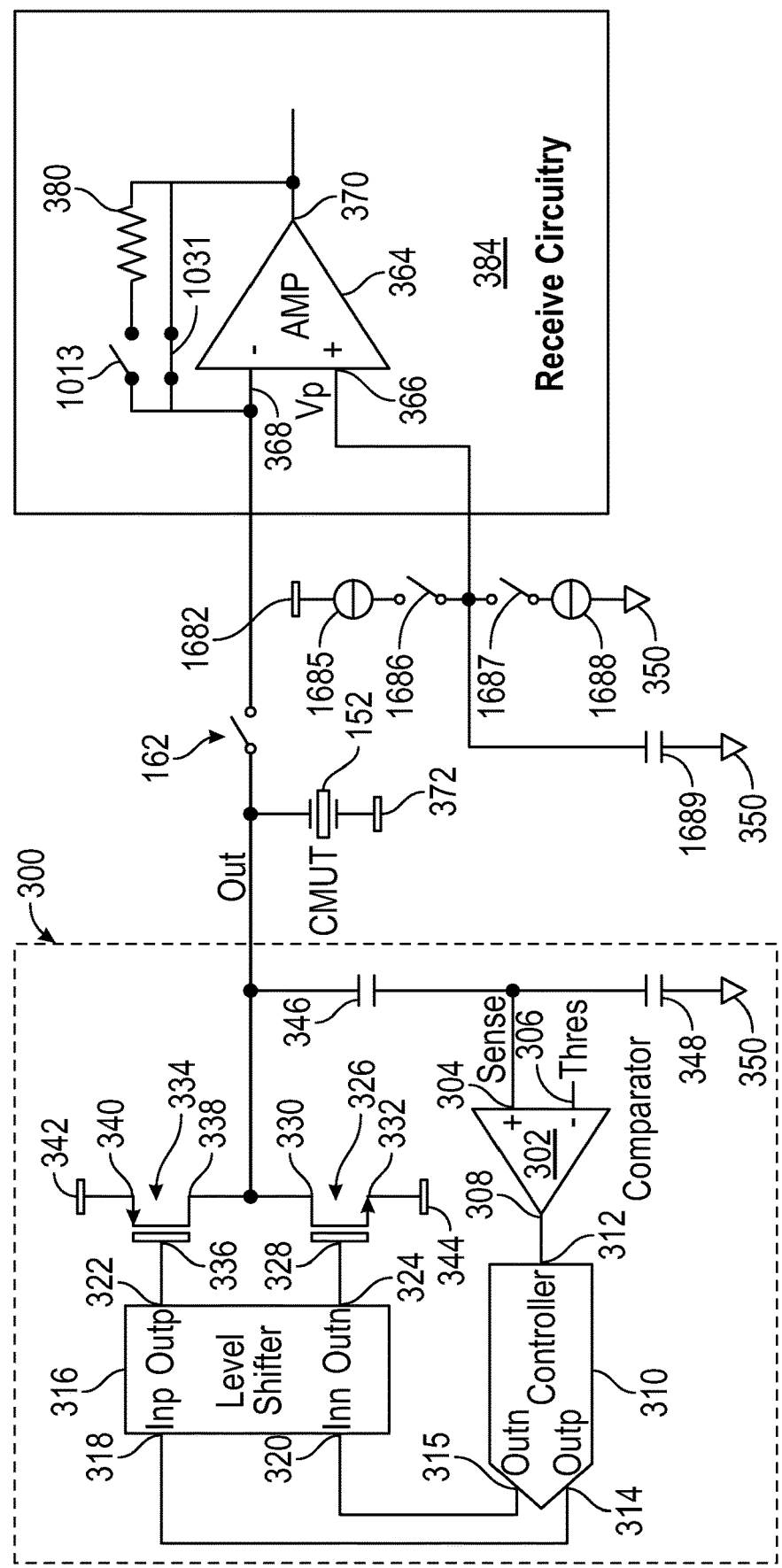
FIG. 16B is an example schematic diagram illustrating circuitry in an ultrasound system, in accordance with certain embodiments described herein.

FIG. 16B is an example schematic diagram illustrating circuitry in an ultrasound system, in accordance with certain embodiments described herein. FIG. 16B is the same as FIG. 16A, except that the receive switch 162 is open, the switch 1031 is closed such that the amplifier 364 may be configured as a unity-gain voltage amplifier, the current sources 1685 and 1688 are coupled through the switches 1686 and 1687, respectively, to the positive input terminal 366 of the amplifier 364, and a capacitor 1689 is coupled between the positive input terminal 366 of the amplifier 364 and ground 350.

In some embodiments, the circuitry of FIG. 16B may be used to inject a waveform to the receive circuitry 384 for testing of the receive circuitry 384. In operation, the switch 1686 may be closed and the switch 1687 may be opened, such that the current source 1685 supplies a constant current to the node Vp (i.e., the node at the positive input terminal 366 of the amplifier 364), charging the capacitor 1689 and generating an increasing ramp voltage at the node Vp. Alternatively or additionally, the switch 1687 may be closed and the switch 1686 may be opened, such that the current source 1688 sinks a constant current from the node Vp, discharging the capacitor 1689 and generating a decreasing ramp voltage at the node Vp. This ramp voltage may be the waveform injected to the receive circuitry 384 for testing the receive circuitry 384.

Figure 17:
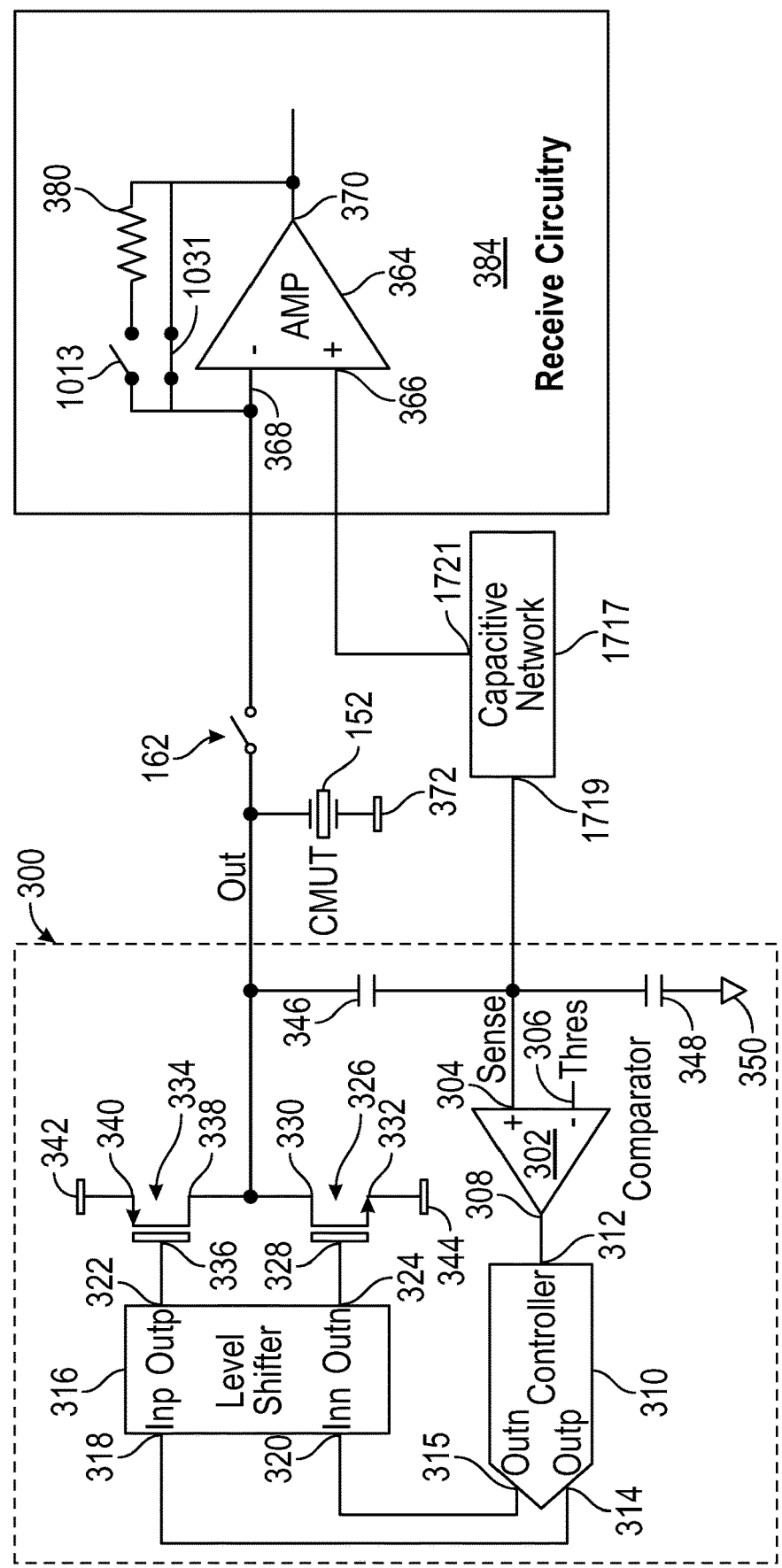
FIG. 17 is an example schematic diagram illustrating circuitry in an ultrasound system, in accordance with certain embodiments described herein.
Figure 21:
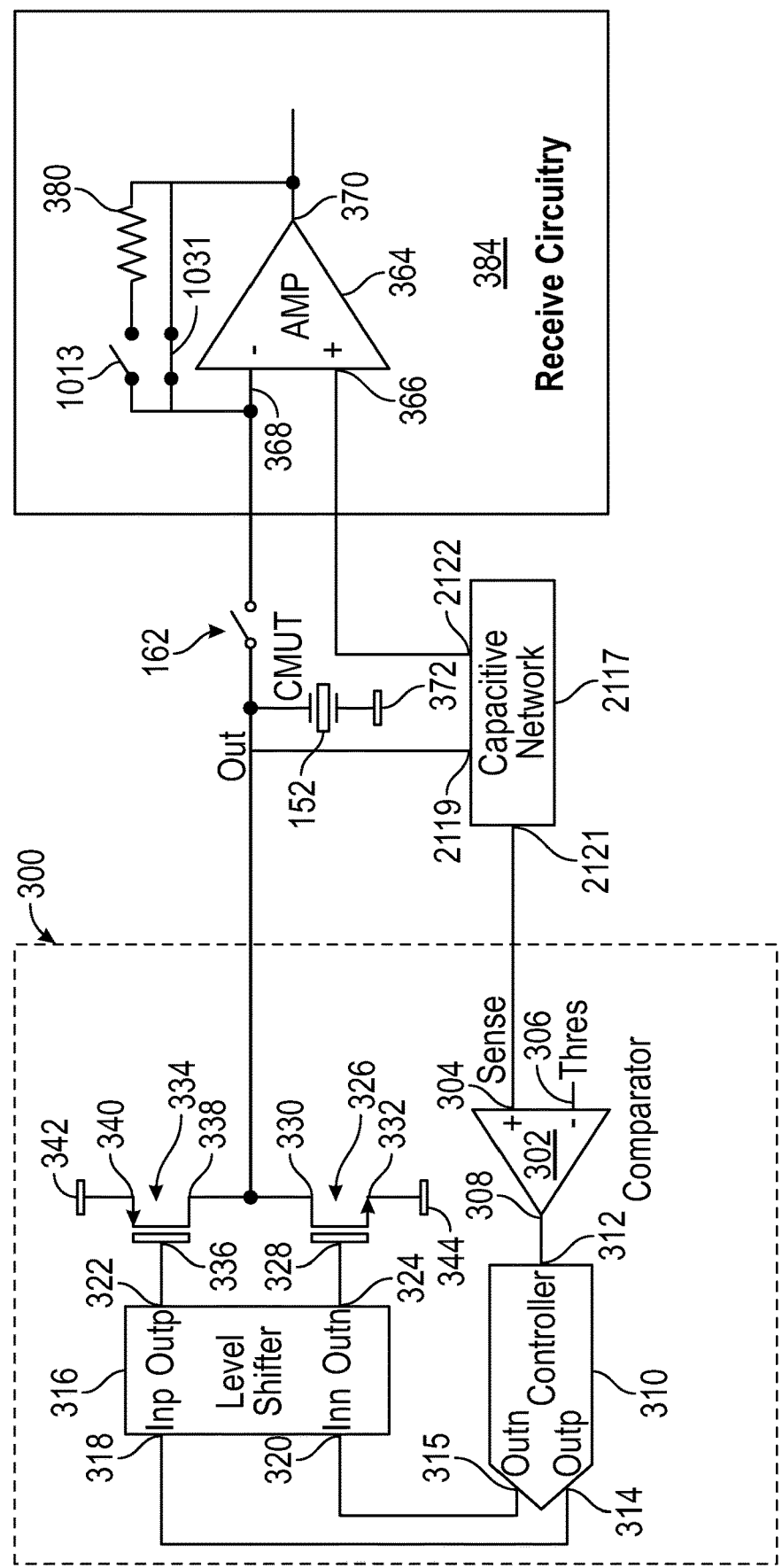
FIG. 21 is an example schematic diagram illustrating circuitry in an ultrasound system, in accordance with certain embodiments described herein.

FIG. 17 is an example schematic diagram illustrating circuitry in an ultrasound system, in accordance with certain embodiments described herein. FIG. 17 is the same as FIG. 3, but with the addition of a capacitor network 1717 coupled between the pulser 300 and the receive circuitry 384. (While FIGS. 17 and 21 illustrate the receive circuitry 384, alternatively, the receive circuitry 1484 may be used.) As described above, it may be helpful to analyze the output of the pulser 300 for testing purposes. While the receive circuitry 384 may be capable of converting analog voltages to digital codes and outputting the digital codes to an external device where they can be analyzed, it may not be feasible to directly connect the output of the pulser 300 to the receive circuitry 384 (e.g., to the TIA 365). The output of the pulser 300 may include pulses that are higher in voltage (e.g., in the HV domain) than the operating voltage of the receive circuitry 384 (e.g., in the LV domain). The inventors have recognized that, instead, the capacitor network 1717 may be included between the pulser 300 and the receive circuitry 384 for built-in self-testing (BIST). The capacitor network 1717 may be configured to convert the HV output of the pulser 300 (or an attenuated version of the output of the pulser 300) to an attenuated voltage signal that can be processed and output by the receive circuitry 384.

The capacitor network 1717 includes an input terminal 1719 and an output terminal 1721. The input terminal 1719 of the capacitor network 1717 is coupled to the Sense node. The output terminal 1721 of the capacitor network 1717 is coupled to the positive input terminal of the amplifier 364. The switch 1031 is closed and the switch 1013 is open, such that the negative input terminal 368 of the amplifier 364 is coupled to the output terminal 370 of the amplifier 364. Thus, the amplifier 364 may be configured as a unity-gain voltage amplifier. In some embodiments, there may be a voltage buffer between the capacitor network 1717 and the receive circuitry 384.

The capacitor network 1717 may be used for built-in self-testing (BIST) of circuitry in the ultrasound system. FIG. 17 illustrates a non-limiting example of a configuration for testing of the pulser 300. In operation, the capacitor network 1717 may be configured to use capacitive division to attenuate the voltage at Sense from the MV domain to the LV domain and to output the LV signal to the receive circuitry 384. The capacitor divider consisting of the capacitor 346 and the parallel combination of the capacitor 348 and the input capacitance of the capacitor network 1717 may attenuate the HV signal at Out to the MV signal at Sense, and the capacitor network 1717 may attenuate the MV signal at Sense to a LV signal at the output terminal 1721. In some embodiments, the input capacitance of the capacitor network 1717 may be such that when the voltage at Out is attenuated by the capacitor divider consisting of the capacitor 346 and the parallel combination of the capacitor 348 and the input capacitance of the capacitor network 1717, then the attenuation ratio between the voltage at Out and the voltage at Sense is as desired. For example, if the desired attenuation ratio is that the voltage at Sense is 1/N the voltage at Out, then the capacitance of the capacitor 346 may be C, the capacitance of the capacitor 348 may be (N−1)C, and the input capacitance of the capacitor network 1717 may be C.

FIG. 18 is a circuit diagram of an example capacitor network 1817, in accordance with certain embodiments described herein. The capacitor network 1817 may be used as the capacitor network 1717. The capacitor network 1817 may be configured to attenuate the voltage at Sense by 2 at the node div2, attenuate the voltage at div2 by 2 at the node div4, and attenuate the voltage at div4 by 2 at div8. The capacitor network 1817 may therefore be configured to provide multiple attenuation options which may be multiplexed to the output of the capacitor network 1817 (which may be the same as the output terminal 1717 of the capacitor network 1717). The capacitor network 1817 also includes a node Common that may be at a constant voltage that can be coupled, through switches (not illustrated), to other nodes (e.g., div2, div4, and div8) in the capacitor network 1817, in order to reset the voltage across the capacitors.

FIG. 19 is a circuit diagram of another example capacitor network 1917, in accordance with certain embodiments described herein. The capacitor network 1917 may be used as the capacitor network 1717. The capacitor network 1917 is the same as the capacitor network 1817, except that a 2 C and a C capacitor have been removed, such that the capacitor network may not provide the div8 attenuation option.

FIG. 20 is a circuit diagram of another example capacitor network 2017, in accordance with certain embodiments described herein. The capacitor network 2017 may be used as the capacitor network 1717. The capacitor network 2017 is the same as the capacitor network 1817, except that a 2 C and a C capacitor have been added, such that the capacitor network provides an output option for attenuation of div8 by 2 at the node div16. It should be appreciated from FIGS. 18-20 that further or fewer attenuation options may be realized by adding or removing a 2 C capacitor and a C capacitor in the manner illustrated.

FIG. 21 is an example schematic diagram illustrating circuitry in an ultrasound system, in accordance with certain embodiments described herein. FIG. 21 includes a pulser 2100 (which may be an example of the pulser 100), the capacitive micromachined ultrasonic transducer (CMUT) 152, the receive switch 162, the receive circuitry 384, and a capacitor network 217. The capacitor network 2117 includes an input terminal 2119, a first output terminal 2121, and a second output terminal 2122. The input terminal 2119 of the capacitor network 2117 is coupled to the Out node. The second output terminal 2122 of the capacitor network 2117 is coupled to the positive input terminal of the amplifier 364. The first output terminal 2121 of the capacitor network 2117 is coupled to the positive input terminal 304 of the comparator 304. The switch 1031 is closed and the switch 1013 is open, such that the negative input terminal 368 of the amplifier 364 is coupled to the output terminal 370 of the amplifier 364. Thus, the amplifier 364 may be connected as a unity-gain voltage amplifier.

The pulser 2100 is the same as the pulser 300, except that the pulser 2100 lacks the capacitor 346 and the capacitor 348. Instead, the attenuation operation performed by the capacitor 346 and the capacitor 348 in the pulser 300 may be performed by the capacitor network 2117. In other words, the capacitor network 2117 may be configured to receive, as an input, an output signal from the pulser 2100 and output an attenuated version of the output signal from the pulser 2100 both to the pulser 2100 and to the receive circuitry 384. In particular, in operation, the capacitor network 2117 may receive the HV signal at Out at the input terminal 2119 and output an attenuated, MV pulse signal at the first output terminal 2121. In some embodiments, there may be a voltage buffer between the capacitor network 2117 and the receive circuitry 384.

The capacitor network 2117 may also be used for built-in self-testing (BIST) of circuitry in the ultrasound system. FIG. 21 illustrates a non-limiting example of a configuration for testing of the pulser 2100. In operation, the capacitor network 2117 may use capacitive division to attenuate the voltage at Out from the HV domain to the LV domain and output the LV signal to the receive circuitry 384.

FIG. 22 is a circuit diagram of an example capacitor network 2217, in accordance with certain embodiments described herein. The capacitor network 2217 may be used as the capacitor network 2117. The capacitor network 2217 may be configured to only output at the node div2 the positive portion of the voltage at Sense such that the attenuation ratio from Out is 2. The capacitor network 2217 may be configured to output at the node div4 the voltage at div2 attenuated by 2, to output at the node div8 the voltage at div4 attenuated by 2, and to output at the node divX the voltage at div8 attenuated by a factor determined by a capacitor divider consisting of the capacitor coupled to the node divX and the load capacitance (Cload) of the circuit coupled to the node divX (e.g., at the second output terminal 2122). For example, the load capacitance may be input capacitance of the amplifier 364. In some embodiments, the attenuation ratio from div8 to divX may be approximately equal to C/Cload. In general, the attenuation ratios may depend on Cload being much larger than C. The capacitor network 2217 may therefore be configured to provide multiple attenuation options which may be multiplexed to the outputs of the capacitor network 1817 (which may be the same as the first output terminal 2121 and the second output terminal 2122 of the capacitor network 1717). The voltage at div4 and div8 may be in the MV domain and may therefore be coupled to the positive input terminal 304 of the comparator 302 (e.g., through the first output terminal 2121). The voltage at divX may be in LV domain and may therefore be coupled to the positive input terminal of the amplifier 364 (e.g., through the second output terminal 2122). The capacitor network 2217 may also include a node Common at a constant voltage that can be coupled, through switches (not illustrated), to other nodes (e.g., div4, div8, and divX) in the capacitor network 2217, in order to reset the voltage across the capacitors. In some embodiments, the capacitor network 2217 may require fewer units of capacitance than the capacitor network 1817 in order to perform the same functions.

FIG. 23 is a circuit diagram of an example capacitor network 2317, in accordance with certain embodiments described herein. The capacitor network 2317 may be used as the capacitor network 2117. The capacitor network 2317 is the same as the capacitor network 2217, except that a 2 C and a C capacitor have been removed. The capacitor network 2317 may therefore provide at attenuation ratio of 2 at div2, an attenuation ratio of 4 at div4, and an attenuation ratio approximately equal to C/Cload at divX.

FIG. 24 is a circuit diagram of another example capacitor network 2417, in accordance with certain embodiments described herein. The capacitor network 2417 may be used as the capacitor network 2117. The capacitor network 2417 is the same as the capacitor network 2217, except that a 2 C and a C capacitor have been added. The capacitor network 2217 may be configured to output at the node div4 the voltage at div2 attenuated by 2, to output at the node div8 the voltage at div4 attenuated by 2, to output at the node div16 the voltage at div8 attenuated by 2, and to output at the node divX the voltage at div16 attenuated by a factor determined by a capacitor divider consisting of the capacitor coupled to the node divX and the load capacitance (Cload) of the circuit coupled to the node divX (e.g., at the second output terminal 2122). For example, the load capacitance may be input capacitance of the amplifier 364. In some embodiments, the attenuation ratio from div8 to divX may be approximately equal to C/Cload. In general, the attenuation ratios may depend on Cload being much larger than C. It should be appreciated from FIGS. 22-24 that further or fewer attenuation options may be realized by adding or removing a 2 C capacitor and a C capacitor in the manner illustrated.

FIG. 25 is a circuit diagram of an example capacitor network 2517, in accordance with certain embodiments described herein. The capacitor network 2517 may be used as the capacitor network 2117. The capacitor network 2517 may be configured to only output at the node div2 the positive portion of the voltage at Sense such that the attenuation ratio from Out is 2. The capacitor network 2517 may be configured to output at the node div4 the voltage at div2 attenuated by 2, to output at the node div8 the voltage at div4 attenuated by 2, and to output at the node divX the voltage at div8 attenuated by a factor determined by a capacitor divider consisting of the capacitor coupled to the node divX and the load capacitance (Cload) of the circuit coupled to the node divX (e.g., at the second input terminal 2122). For example, the load capacitance may be input capacitance of the amplifier 364. In some embodiments, the attenuation ratio from div8 to divX may be approximately equal to 2 C/Cload. In general, the attenuation ratios may depend on Cload being much larger than C. The capacitor network 2517 may therefore be configured to provide multiple attenuation options which may be multiplexed to the outputs of the capacitor network 1817 (which may be the same as the first output terminal 2121 and the second output terminal 2122 of the capacitor network 1717). The voltage at div4 and div8 may be in the MV domain and may therefore be coupled to the positive input terminal 304 of the comparator 302 (e.g., through the first output terminal 2121). The voltage at divX may be in LV domain and may therefore be coupled to the positive input terminal of the amplifier 364 (e.g., through the second output terminal 2122). The capacitor network 2517 may also include a node Common at a constant voltage that can be coupled, through switches (not illustrated), to other nodes (e.g., div4, div8, and divX) in the capacitor network 2517, in order to reset the voltage across the capacitors. In some embodiments, to remove an attenuation ratio from the capacitor network 2517, the capacitor network 2317 may be used.

FIG. 26 is a circuit diagram of another example capacitor network 2617, in accordance with certain embodiments described herein. The capacitor network 2617 may be used as the capacitor network 2117. The capacitor network 2617 is the same as the capacitor network 2517, except that a 2 C and a C capacitor have been added. The capacitor network 2617 may be configured to output at the node div4 the voltage at div2 attenuated by 2, to output at the node div8 the voltage at div4 attenuated by 2, to output at the node div16 the voltage at div8 attenuated by 2, and to output at the node divX the voltage at div16 attenuated by a factor determined by a capacitor divider consisting of the capacitor coupled to the node divX and the load capacitance (Cload) of the circuit coupled to the node divX (e.g., at the second output terminal 2122). For example, the load capacitance may be input capacitance of the amplifier 364. In some embodiments, the attenuation ratio from div8 to divX may be approximately equal to 2 C/Cload. It should be appreciated from FIGS. 25-26 that further or fewer attenuation options may be realized by adding or removing a 2 C capacitor and a C capacitor in the manner illustrated. It should also be appreciated from FIGS. 22-26 that the attenuation ratio of the last stage may be modulated by modulating the capacitor at the last stage. Depending of the attenuation ratios desired and the voltage levels involved, one of the capacitor networks in FIGS. 22-26 and a capacitance for the last stage may be selected.

FIGS. 27-34 illustrate ultrasound devices and substrates containing circuitry that may be included in the ultrasound devices. As examples, a substrate may include a semiconductor chip, a printed circuit board, a microprocessor, or a field-programmable gate array (FPGA). It should be appreciated that, as illustrated in FIGS. 27-34, any of the illustrated circuitry may be integrated circuitry on a substrate (e.g., on a semiconductor chip). Thus, in some embodiments, BIST circuitry may be integrated circuitry that is integrated on the same substrate (e.g., a semiconductor chip) as other integrated ultrasound circuitry such as a pulsers and/or receive circuitry.

Figure 27:
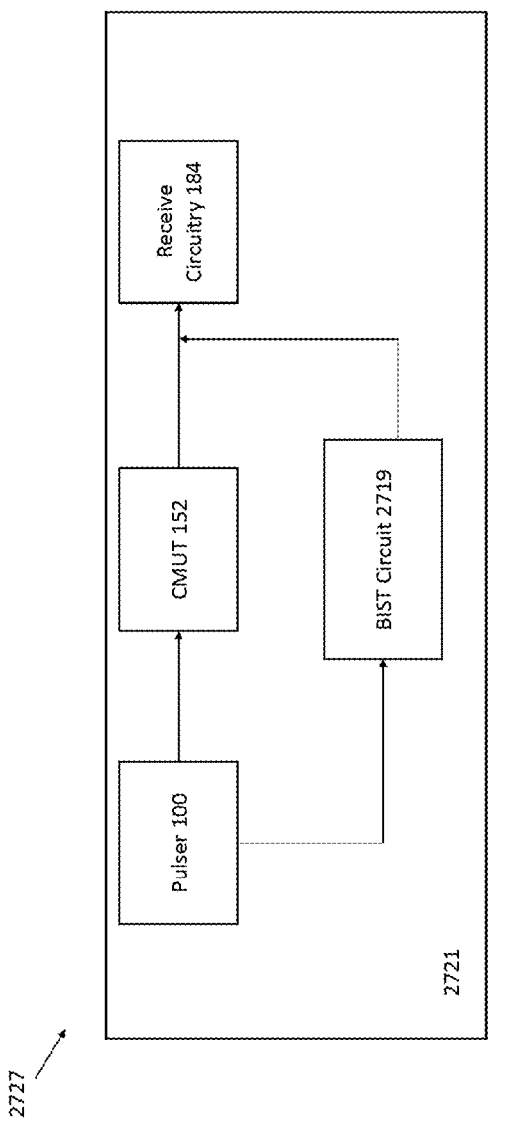
FIG. 27 is a block diagram of an ultrasound circuitry, in accordance with certain embodiments described herein.

FIG. 27 is a block diagram of an ultrasound circuitry 2727, in accordance with certain embodiments described herein. The ultrasound circuitry 2727 includes a substrate 2721. The substrate 2721 includes the pulser 100, the CMUT 152, the receive circuitry 184, and a built-in self-test (BIST) circuit 2719. The BIST circuit 2719 may be the transconductance amplifier 454, the capacitor network 1717, the capacitor network 2117, the current source 1685, the current source 1688, and/or the capacitor 1689. The output of the pulser 100 is coupled to the inputs of the CMUT 152 and the BIST circuit 2719. The output of the CMUT 152 is coupled to the input of the receive circuitry 184. The output of the BIST circuit 2719 is coupled to the input of the receive circuitry 184.

Figure 28:
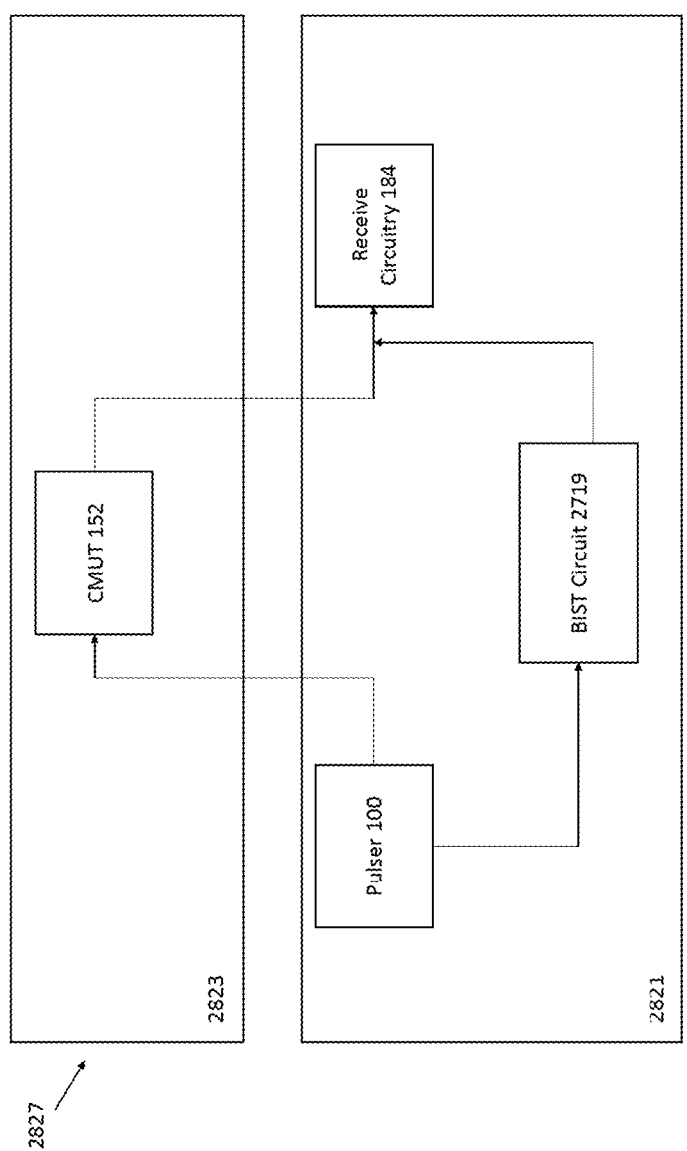
FIG. 28 is a block diagram of another example of ultrasound circuitry, in accordance with certain embodiments described herein.

FIG. 28 is a block diagram of another example of ultrasound circuitry 2827, in accordance with certain embodiments described herein. The ultrasound circuitry 2827 is the same as the ultrasound circuitry 2727, except that the ultrasound circuitry 2827 includes a substrate 2821 and a substrate 2823 instead of the substrate 2721. The pulser 100, the BIST circuit 2719, and the receive circuitry 184 are disposed in the substrate 2821 and the CMUT 152 is disposed in the substrate 2823. In some embodiments, the substrate 2821 and the substrate 2823 may be bonded together, and the CMUT 152 may be electrically coupled to the pulser 100 and the receive circuitry 184 through bonding points.

Figure 29:
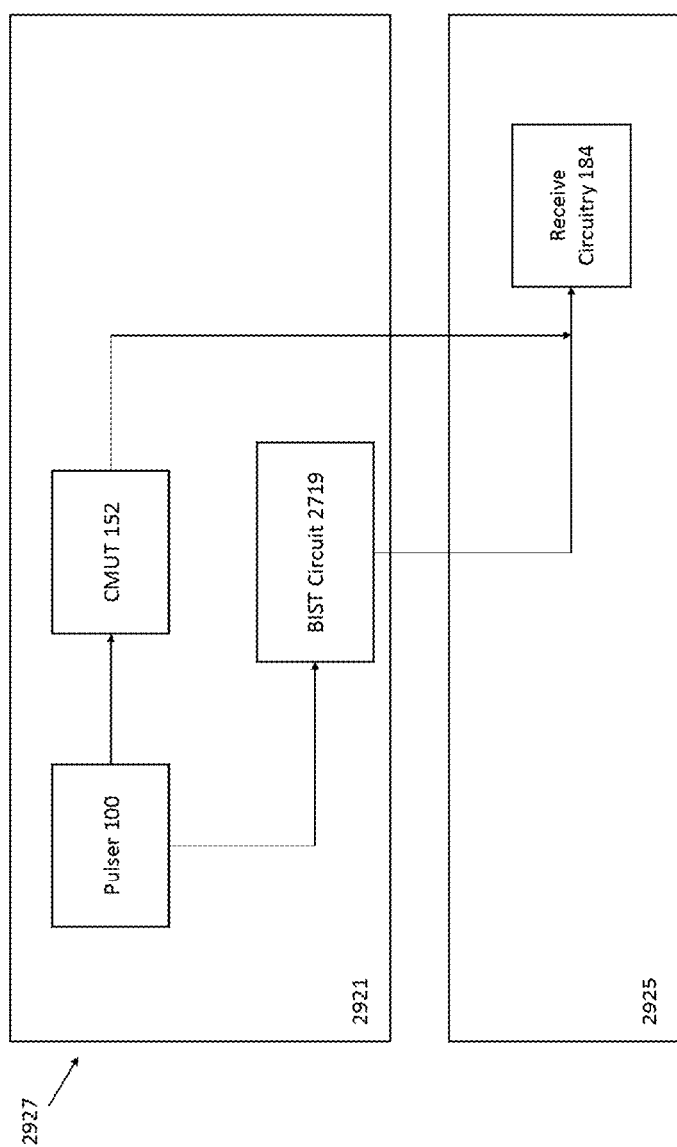
FIG. 29 is a block diagram of another example of ultrasound circuitry, in accordance with certain embodiments described herein.

FIG. 29 is a block diagram of another example of ultrasound circuitry 2927, in accordance with certain embodiments described herein. The ultrasound circuitry 2927 is the same as the ultrasound circuitry 2727, except that the ultrasound circuitry 2927 includes a substrate 2921 and a substrate 2925 instead of the substrate 2721. The pulser 100, the BIST circuit 2719, and the CMUT 152 are disposed in the substrate 2921 and the receive circuitry 184 is disposed in the substrate 2925. In some embodiments, the substrate 2921 and the substrate 2925 may be bonded together, and the receive circuitry 184 may be electrically coupled to the BIST circuit 2719 and the CMUT 152 through bonding points.

Figure 30:
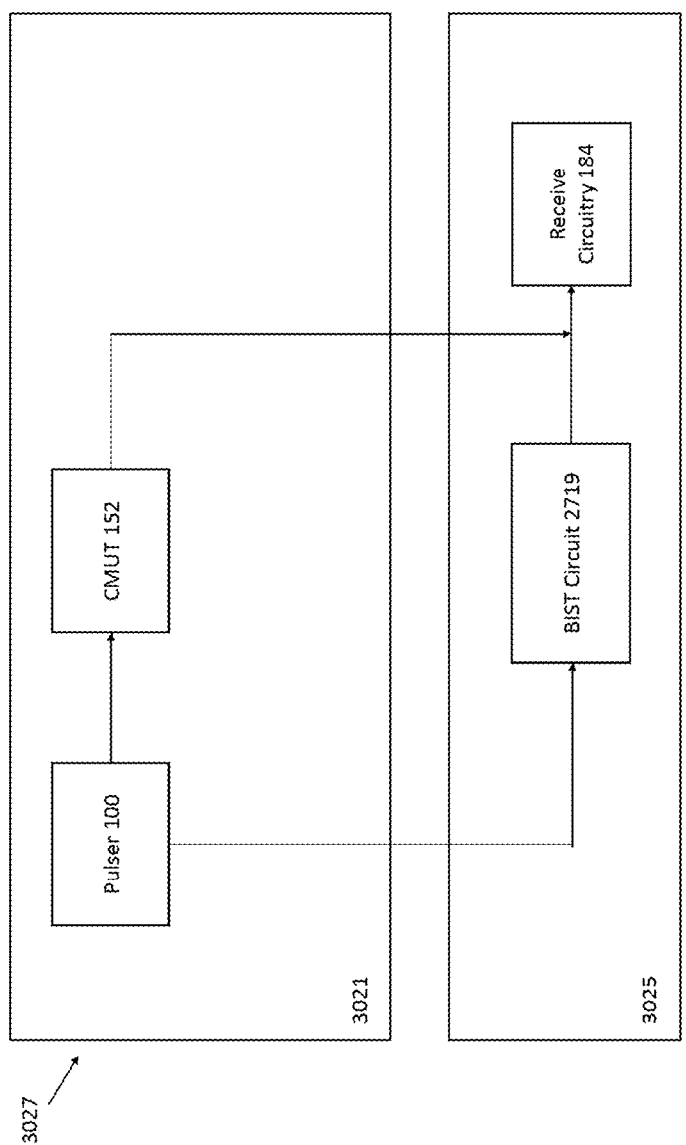
FIG. 30 is a block diagram of another example of ultrasound circuitry, in accordance with certain embodiments described herein.

FIG. 30 is a block diagram of another example of ultrasound circuitry 3027, in accordance with certain embodiments described herein. The ultrasound circuitry 3027 is the same as the ultrasound circuitry 2927, except that the ultrasound circuitry 3027 includes a substrate 3021 instead of the substrate 2921 and a substrate 3025 instead of the substrate 2925. The pulser 100 and the CMUT 152 are disposed in the substrate 3021 and the BIST circuit 2719 and the receive circuitry 184 are disposed in the substrate 2925. In some embodiments, the substrate 3021 and the substrate 3025 may be bonded together, and the pulser 100 may be electrically coupled to the BIST circuit 2719 and the CMUT 152 may be electrically coupled to the receive circuitry 184 through bonding points.

Figure 31:
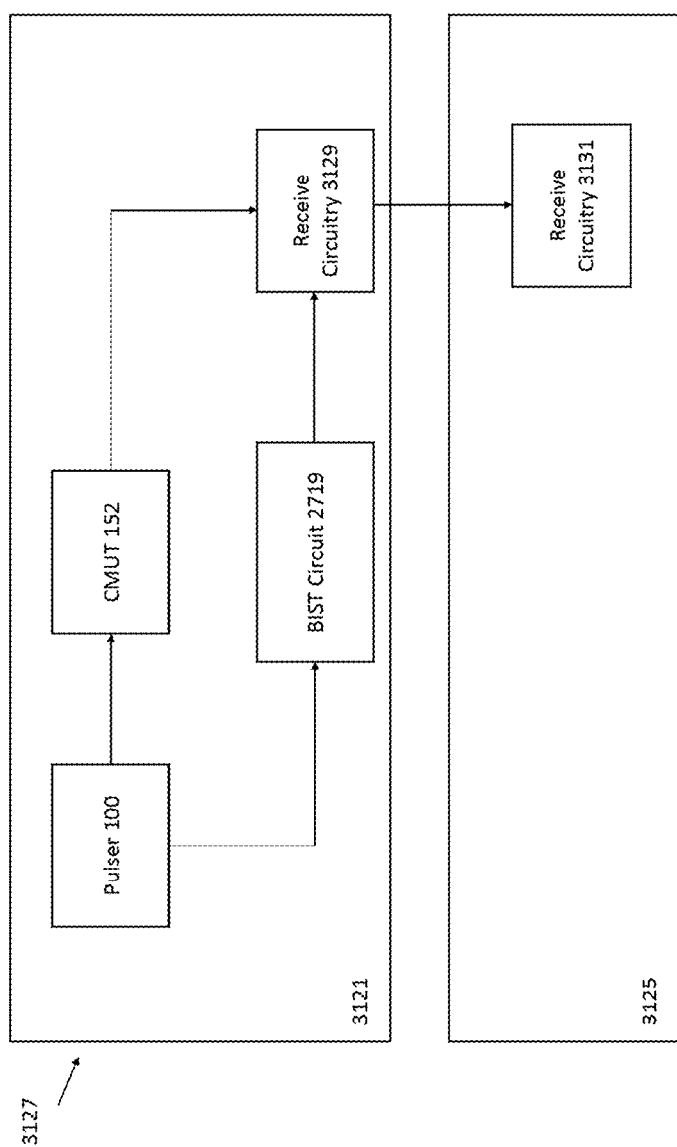
FIG. 31 is a block diagram of another example of ultrasound circuitry, in accordance with certain embodiments described herein.

FIG. 31 is a block diagram of another example of ultrasound circuitry 3127, in accordance with certain embodiments described herein. The ultrasound circuitry 3127 includes a substrate 3121 and a substrate 3125. The substrate 3121 includes the pulser 100, the CMUT 152, the BIST circuit 2719, receive circuitry 3129, and receive circuitry 3131. The receive circuitry 3129 and the receive circuitry 3131 may represent division of the receive circuitry 184 into two blocks. The output of the pulser 100 is coupled to the inputs of the CMUT 152 and the BIST circuit 2719. The output of the CMUT 152 is coupled to the input of the receive circuitry 3129. The output of the BIST circuit 2719 is coupled to the input of the receive circuitry 3129. The output of the receive circuitry 3129 is coupled to the input of the receive circuitry 3131. In some embodiments, the substrate 3121 and the substrate 3125 may be bonded together, and the receive circuitry 3129 may be electrically coupled to the receive circuitry 3131 through bonding points. In some embodiments, the substrate 3121 and the substrate 3125 may be electrically coupled through one or more communication links, and the receive circuitry 3129 may be electrically coupled to the receive circuitry 3131 through the communication links. In some embodiments, the receive circuitry 3129 may include a transimpedance amplifier and/or an analog-to-digital converter (ADC) and the receive circuitry 3131 may include digital processing circuitry (although the receive circuitry 3129 and the receive circuitry 3131 may include other circuitry as well). In some embodiments, the receive circuitry 3129 may include a preamplifier, time-gain compensation (TGC) circuitry, and/or analog beamforming circuitry, and the receive circuitry 3131 may include a transimpedance amplifier, an analog-to-digital converter (ADC), and/or digital processing circuitry (although the receive circuitry 3129 and the receive circuitry 3131 may include other circuitry as well).

Figure 32:
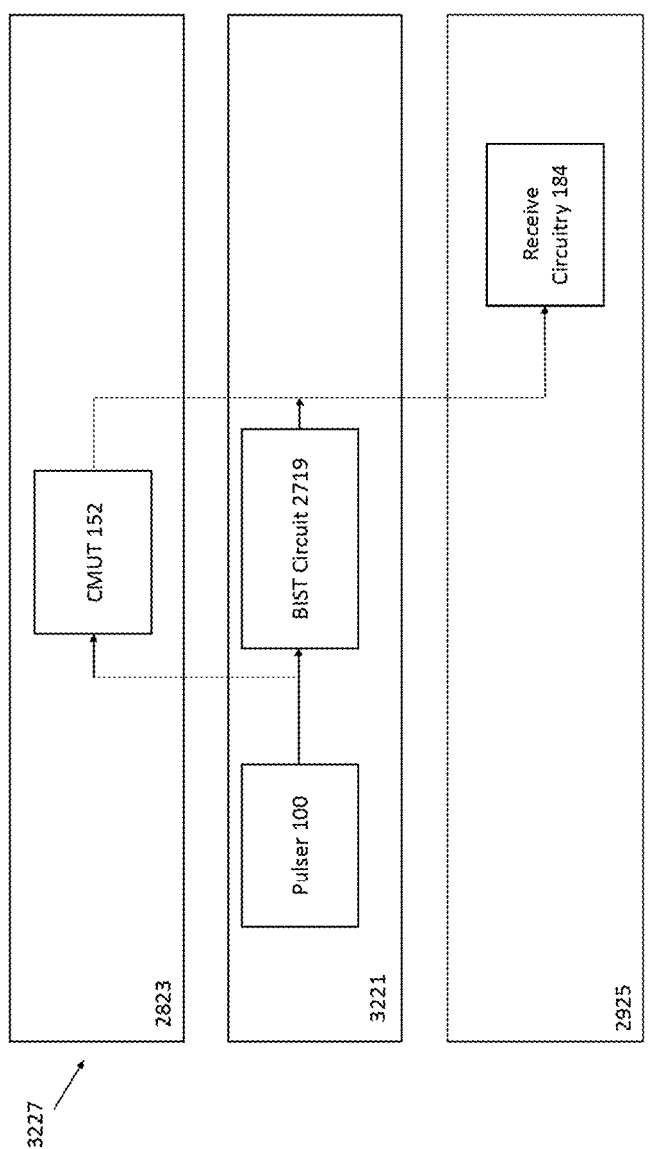
FIG. 32 is a block diagram of another example of ultrasound circuitry, in accordance with certain embodiments described herein.

FIG. 32 is a block diagram of another example of ultrasound circuitry 3227, in accordance with certain embodiments described herein. The ultrasound circuitry 3227 includes a substrate 3221, the substrate 2823, and the substrate 2925. The pulser 100 and the BIST circuit 2719 are disposed in the substrate 3221. In some embodiments, the substrate 3221 and the substrate 2823 may be bonded together, and the substrate 3221 and the substrate 2925 may be bonded together. In such embodiments, the CMUT 152 may be electrically coupled to the pulser 100 and the receive circuitry 184 through bonding points.

Figure 33:
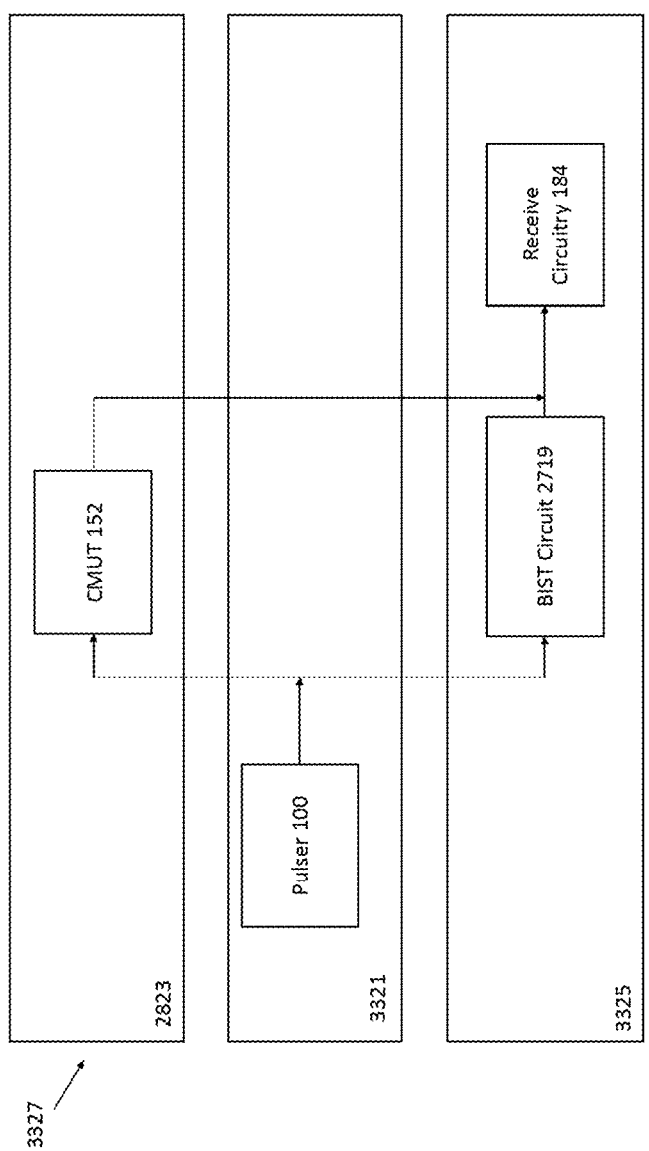
FIG. 33 is a block diagram of another example of ultrasound circuitry, in accordance with certain embodiments described herein.

FIG. 33 is a block diagram of another example of ultrasound circuitry 3327, in accordance with certain embodiments described herein. The ultrasound circuitry 3327 includes a substrate 3321, the substrate 2823, and the substrate 3325. The pulser 100 is disposed in the substrate AF21 and the BIST circuit 2719 and the receive circuitry 184 are disposed in the substrate 3325. In some embodiments, the substrate 3321 and the substrate 2823 may be bonded together, and the substrate 33V21 and the substrate 3325 may be bonded together. In such embodiments, the CMUT 152 may be electrically coupled to the pulser 100 and the receive circuitry 184 through bonding points, and the pulser 100 may be electrically coupled to the BIST circuit 2719 through bonding points.

Figure 34:
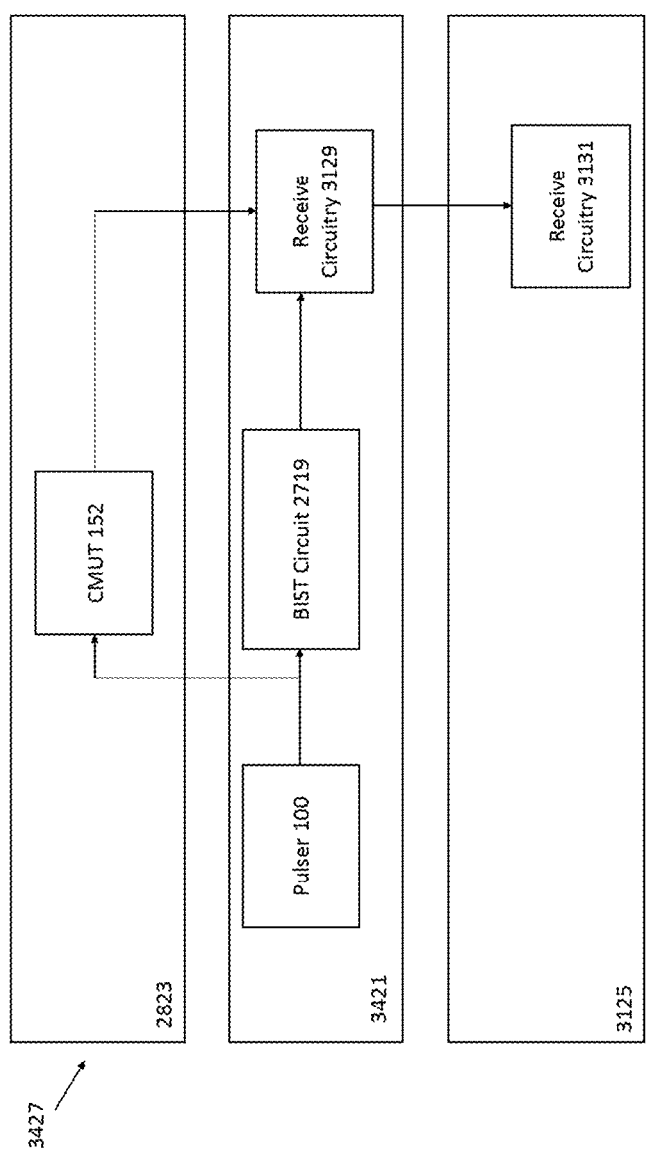
FIG. 34 is a block diagram of another example of ultrasound circuitry, in accordance with certain embodiments described herein.

FIG. 34 is a block diagram of another example of ultrasound circuitry 3427, in accordance with certain embodiments described herein. The ultrasound circuitry 3427 includes a substrate 3421, the substrate 2823, and the substrate 3125. The pulser 100, the BIST circuit 2719, and the receive circuitry 3129 are disposed in the substrate 3421. In some embodiments, the substrate 3421 and the substrate 2823 may be bonded together, and the CMUT 152 may be electrically coupled to the pulser 100 and the receive circuitry 3129 through bonding points. In some embodiments, the substrate 3421 and the substrate 3125 may be bonded together, and the receive circuitry 3129 may be electrically coupled to the receive circuitry 3131 through bonding points. In some embodiments, the substrate 3421 and the substrate 3125 may be electrically coupled through one or more communication links, and the receive circuitry 3129 may be electrically coupled to the receive circuitry 3131 through the communication links.

In any of the substrates described herein, the pulser 100, the BIST circuit 2719, the receive circuitry 184, the receive circuitry 3129, and/or the receive circuitry 3131 may be integrated circuitry fabricated in the substrate (e.g., in a semiconductor chip). Additionally, in any of the substrates described herein that include such integrated circuitry and the CMUT 152, the CMUT 152 may be fabricated in the substrate after the integrated circuitry has been fabricated in the substrate.

It should be appreciated that in any of the ultrasound devices described herein that include two or more substrates, any or all of the substrates may be included in a single package. Thus, the BIST circuit 2719, the receive circuitry, CMUT 152, and the pulser 100 may be disposed within a single package. The BIST circuit 2719 may thus be included in the final ultrasound device product, despite potentially not being used once the ultrasound device is in the hands of consumers.

Figures 35A, 35B:
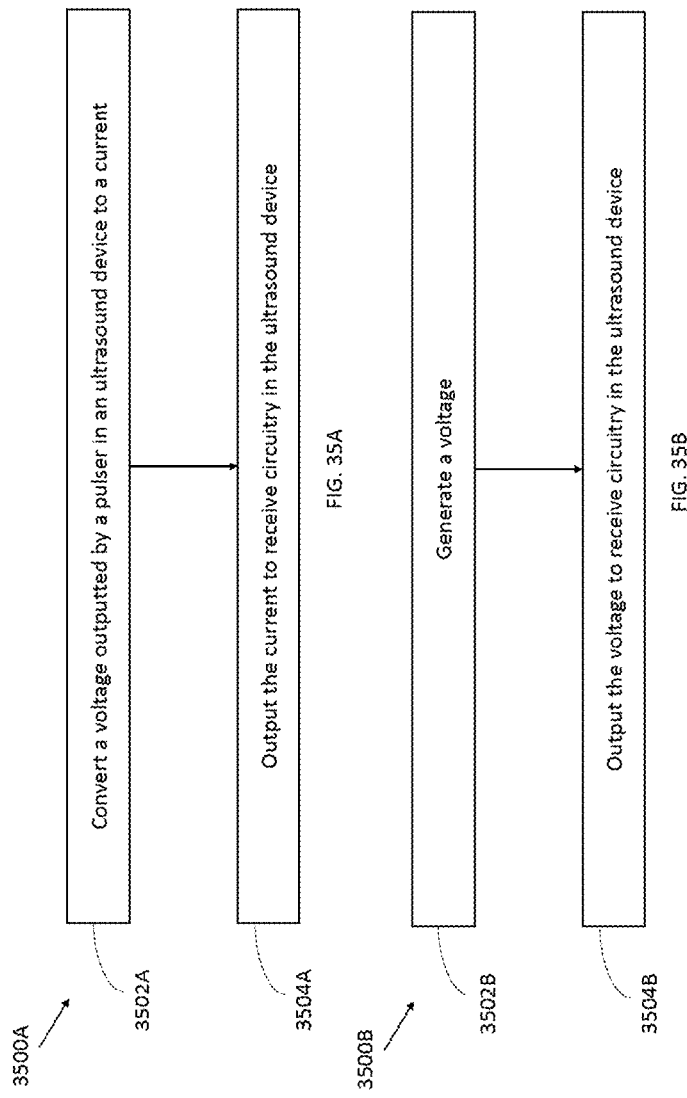
FIG. 35A illustrates a flow diagram for a process for testing a pulser in an ultrasound device, in accordance with certain embodiments described herein.
FIG. 35B illustrates a flow diagram for a process for testing receive circuitry in an ultrasound device, in accordance with certain embodiments described herein.

FIG. 35A illustrates a flow diagram for a process 3500A for testing a pulser in an ultrasound device, in accordance with certain embodiments described herein. The process 3500A may be performed by operating a transconductance amplifier (e.g., the transconductance amplifier 454) coupled between a pulser (e.g., the pulser 300) and receive circuitry (e.g., the receive circuitry 184, the receive circuitry 384, or the receive circuitry 1484) in an ultrasound device (e.g., the ultrasound device 4402 described below).

In act 3502A, the transconductance amplifier is operated to convert a voltage outputted by the pulser in the ultrasound device to a current. The process 3500A proceeds from act 3502A to act 3504A.

In act 3504A, the transconductance amplifier is operated to output the current to the receive circuitry (e.g., to a TIA (e.g., the TIA 365) or to a delta-sigma ADC (e.g., the delta-sigma ADC 1400) in the receive circuitry) in the ultrasound device. In some embodiments, after testing the pulser, the transconductance amplifier may be shut off while the pulser and the receive circuitry remain on. Further description of circuitry that may be configured to perform the process 3500A may be found with reference to FIGS. 4-7 and 10-14. The process 3500A may also be used for testing the receive circuitry as described after the description of FIG. 15.

FIG. 35B illustrates a flow diagram for a process 3500B for testing receive circuitry (e.g., the receive circuitry 384) in an ultrasound device, in accordance with certain embodiments described herein. The process 3500B may be performed by operating current sources (e.g., the current sources 1685 and 1688) each coupled through a switch (e.g., the switches 1686 and 1687) to a capacitor (e.g., the capacitor 1689) and to an input terminal of the receive circuitry (i.e., the positive input terminal 366 of the amplifier 364).

In act 3502B, the current sources and switches are operated to generate a current. For example, one of the switches may be closed and the other switch may be opened, such that one of the current sources supplies a constant current to the capacitor and charges the capacitor, generating an increasing ramp voltage at the input terminal of the receive circuitry. Alternatively or additionally, the switch may be opened and the other switch may be closed, such that the other current sources supplies a constant current to the capacitor and discharges the capacitor, generating an decreasing ramp voltage at the input terminal of the receive circuitry.

In act 3504B, the ramp voltage generated in act 3502B is output to the receive circuitry (e.g., to an amplifier (e.g., the amplifier 364) configured as a unity-gain buffer) in the ultrasound device. This ramp voltage may be the waveform injected to the receive circuitry 384 for testing the receive circuitry 384.

FIG. 36 illustrates a flow diagram for a process 3600 for testing a pulser in an ultrasound device, in accordance with certain embodiments described herein. The process 3600 may be performed by operating a capacitor network (e.g., the capacitor network 1717 or the capacitor network 2117) coupled between a pulser (e.g., the pulser 300 or the pulser 2100) and receive circuitry (e.g., the receive circuitry 184, the receive circuitry 384, or the receive circuitry 1484) in an ultrasound device (e.g., the ultrasound device 4402 described below).

In act 3602, the capacitor network is operated to attenuate a voltage outputted by the pulser in the ultrasound device. The process 3600 proceeds from act 3602 to act 3604.

In act 3604, the capacitor network is operated to output the attenuated voltage to the receive circuitry (e.g., to a unity-gain amplifier in the receive circuitry) in the ultrasound device. In some embodiments, the capacitor network may also output an attenuated version of the output of the pulser back to the pulser itself. Further description of circuitry that may be configured to perform the process 3600 may be found with reference to FIGS. 17-26.

FIG. 37 illustrates a flow diagram for a process 3700 for characterizing a capacitive micromachined ultrasonic transducer (CMUT) (e.g., the CMUT 352), in accordance with certain embodiments described herein. For example, the characterization may be characterization of the CMUT's capacitance. The process 3700 may be performed by operating a transconductance amplifier (e.g., the transconductance amplifier 454) coupled to receive circuitry (e.g., the receive circuitry 184, the receive circuitry 384, or the receive circuitry 1484) in an ultrasound device (e.g., the ultrasound device 4402 described below). An input terminal of the receive circuitry is electrically coupled to the CMUT. For example, to electrically couple the CMUT to the input terminal of the receive circuitry, a switch (e.g., the receive switch 362) between the CMUT and the input terminal of the receive circuitry may be closed.

In act 3702, the transconductance amplifier is operated to generate a current. For example, the transconductance amplifier may accept constant voltages at its inputs and output a constant current based on the difference between the two inputted voltages. The process 3700 proceeds from act 3702 to act 3704.

In act 3704, the transconductance amplifier is operated to inject the current to the input terminal of the receive circuitry (e.g., to an amplifier configured as a comparator). The current may charge or discharge the CMUT to generate a ramp voltage. The ramp may begin at the voltage VDDA of a positive power supply and proceed to ground or begin at ground and proceed to VDDA. The receive circuitry (e.g., a comparator in the receive circuitry) may be used to measure the time $T_{ramp}$ it takes for the ramp voltage to cross a reference voltage Vref. The capacitance of the CMUT may be computed as $$C = \frac{I_{ramp} \times T_{ramp}}{VDDA - Vref},$$

where $I_{ramp}$ is the constant current generated by the transconductance amplifier and $T_{ramp}$ is the time it takes from the beginning of the ramp to when the ramp cross the reference voltage Vref. In some embodiments, after characterizing the CMUT, the transconductance amplifier may be shut off while the pulser and the receive circuitry remain on. Further description of circuitry that may be configured to perform the process 3700 may be found with reference to FIGS. 8-13 and 15.

Figure 38:
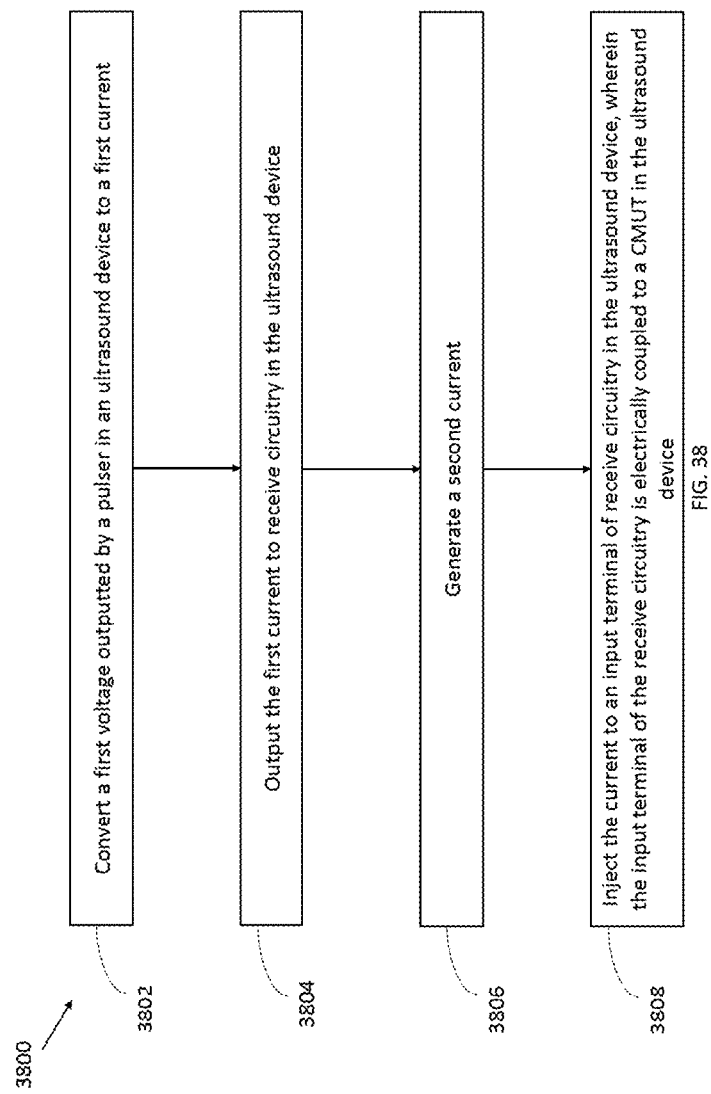
FIG. 38 illustrates a flow diagram for a process for testing a pulser in an ultrasound device, in accordance with certain embodiments described herein.

In some embodiments, the same transconductance amplifier coupled between the pulser and the receive circuitry may be used to test the pulser and to characterize the CMUT in the ultrasound device. FIG. 38 illustrates a flow diagram for a process 3800 for testing a pulser in an ultrasound device, in accordance with certain embodiments described herein. The process 3800 may be performed by operating a transconductance amplifier (e.g., the transconductance amplifier 454) coupled between a pulser (e.g., the pulser 300) and receive circuitry (e.g., the receive circuitry 184, the receive circuitry 384, or the receive circuitry 1484) in an ultrasound device (e.g., the ultrasound device 4402 described below).

In act 3802, the transconductance amplifier is operated to convert a first voltage outputted by the pulser in the ultrasound device to a first current. The process 3800 proceeds from act 3802 to act 3804.

In act 3804, the transconductance amplifier is operated to output the first current to the receive circuitry (e.g., to an amplifier configured as a TIA (e.g., the TIA 365) in the receive circuitry) in the ultrasound device. Further description of circuitry that may be configured to perform the acts 3802-3804 may be found with reference to FIGS. 4-7 and 10-14.

In act 3806, the transconductance amplifier is operated to generate a second current. For example, the transconductance amplifier may accept constant voltages at its inputs and output a constant current based on the difference between the two inputted voltages. The process 3800 proceeds from act 3806 to act 3808.

In act 3808, the transconductance amplifier is operated to inject the second current to an input terminal of the receive circuitry (e.g., to an amplifier (e.g., the amplifier 364) configured as a comparator). The input terminal of the receive circuitry is electrically coupled to the CMUT. For example, to electrically couple the CMUT to the input terminal of the receive circuitry, a switch (e.g., the receive switch 362) between the CMUT and the input terminal of the receive circuitry may be closed. The second current may charge or discharge the CMUT to generate a ramp voltage. The ramp may begin at the voltage VDDA of a positive power supply and proceed to ground or begin at ground and proceed to VDDA. The receive circuitry (e.g., a comparator in the receive circuitry) may be used to measure the time $T_{ramp}$ it takes for the ramp voltage to cross a reference voltage Vref. The capacitance of the CMUT may be computed as $$C = \frac{I_{ramp} \times T_{ramp}}{VDDA - Vref},$$

where $I_{ramp}$ is the constant current generated by the transconductance amplifier and $T_{ramp}$ is the time it takes from the beginning of the ramp to when the ramp cross the reference voltage Vref. Further description of circuitry that may be configured to perform the acts 3806-3808 may be found with reference to FIGS. 8-13 and 15. In some embodiments, acts 3806-3808 may be performed before acts 3802-3804.

In some embodiments, a process for characterizing a CMUT (e.g., the CMUT 352) may include operating a current source (e.g., the current source 1685 or 1688) in the ultrasound device to inject a current to an input terminal of receive circuitry (e.g., to an amplifier (e.g., the amplifier 364) configured as a comparator). The input terminal is electrically coupled to the CMUT. For example, to electrically couple the CMUT to the input terminal of the receive circuitry, a switch (e.g., the receive switch 362) between the CMUT and the input terminal of the receive circuitry may be closed. The current may charge or discharge the CMUT to generate a ramp voltage. The ramp may begin at the voltage VDDA of a positive power supply and proceed to ground or begin at ground and proceed to VDDA. The receive circuitry (e.g., a comparator in the receive circuitry) may be used to measure the time $T_{ramp}$ it takes for the ramp voltage to cross a reference voltage Vref. The capacitance of the CMUT may be computed as $$C = \frac{I_{ramp} \times T_{ramp}}{VDDA - Vref},$$

where $I_{ramp}$ is the constant current generated by the transconductance amplifier and $T_{ramp}$ is the time it takes from the beginning of the ramp to when the ramp cross the reference voltage Vref. In some embodiments, one current source may source a first current to the input terminal of the receive circuitry to charge or discharge the CMUT and generate a first ramp voltage. A first time for the first ramp voltage to cross a reference voltage may be measured. A second current source may sink a second current from the input terminal of the receive circuitry to charge or discharge the CMUT and generate a second ramp voltage. A second time for the second ramp voltage to cross the reference voltage may be measured. Both the first and second time may be used to compute the capacitance (e.g., by averaging the first and second times and using the above equation). In some embodiments, multiple repeated measurements of the time for ramp voltages to cross the reference voltage may be performed during current sourcing, and these multiple measurements of time may be averaged. Additionally, multiple repeated measurements of the time for ramp voltages to cross the reference voltage may be performed during current sinking, and these multiple measurements of time may be averaged. The two averaged results, one result for current sourcing and one for current sinking, may then be averaged together. Alternatively, the multiple measurements from current sourcing and from current sinking may be averaged together. It should be appreciated that in some embodiments, measuring the time for a ramp voltage to cross the reference voltage during current sourcing may be performed prior to measuring the time for a ramp voltage to cross a reference voltage during current sinking, while in some embodiments, measuring the time for a ramp voltage to cross the reference voltage during current sinking may be performed prior to measuring the time for a ramp voltage to cross the reference voltage during current sourcing. Further description of circuitry that may be configured to perform such a process may be found with reference to FIG. 16A.

Figure 39:
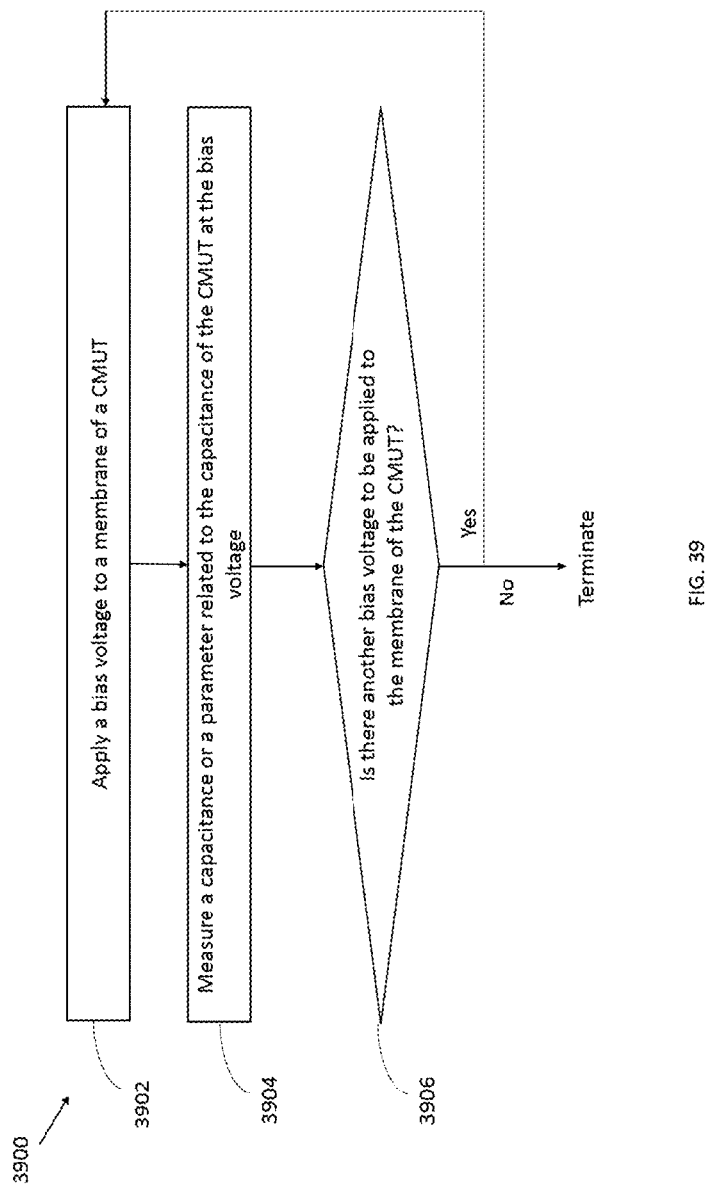
FIG. 39 illustrates a process for performing measurements in order to determine the collapse voltage of a CMUT, in accordance with certain embodiments described herein.

FIG. 39 illustrates a process 3900 for performing measurements in order to determine the collapse voltage of a CMUT (e.g., the CMUT 152), in accordance with certain embodiments described herein. The process 3900 may be performed by an ultrasound device (e.g., the ultrasound device 4402 described below).

In act 3902, the ultrasound device applies a bias voltage $V_{BIAS}$ to a CMUT. The bias voltage $V_{BIAS}$ applied to the CMUT may be measured between the membrane of the CMUT and the bottom electrode at the substrate of the CMUT. If the bottom electrode at the substrate of the CMUT is at virtual ground, then applying $V_{BIAS}$ to the CMUT may be accomplished by applying $V_{BIAS}$ to the membrane. In some embodiments, the ultrasound device may use a DC-DC converter (e.g., the DC-DC converter 4339 described below) to apply the bias voltage $V_{BIAS}$ to the membrane of the CMUT.

In some embodiments, applying $V_{BIAS}$ to the membrane of the CMUT may include routing the voltage $V_{BIAS}$ from circuitry (e.g., the DC-DC converter 4339 described below) in the ultrasound device but external to the substrate on which the CMUT is disposed, through a routing network, and to the membrane of the CMUT. It may be helpful to wait for the voltage at the membrane to settle to $V_{BIAS}$ after charging or discharging the routing network.

In act 3904, the ultrasound device measures a capacitance or a parameter related to the capacitance of the CMUT at the bias voltage applied in act 3902. In some embodiments, the ultrasound device may perform act 3904 by operating a transconductance amplifier (e.g., the transconductance amplifier 454) coupled to receive circuitry (e.g., the receive circuitry 184, the receive circuitry 384, or the receive circuitry 1484) in the ultrasound device. An input terminal of the receive circuitry is electrically coupled to the CMUT.

For example, to electrically couple the CMUT to the input terminal of the receive circuitry, a switch (e.g., the receive switch 362) between the CMUT and the input terminal of the receive circuitry may be closed. The transconductance amplifier may be operated to generate a current. For example, the transconductance amplifier may accept constant voltages at its inputs and output a constant current $T_{ramp}$ based on the difference between the two inputted voltages. The transconductance amplifier may be operated to inject the current to the input terminal of the receive circuitry (e.g., to an amplifier configured as a comparator). The current may charge or discharge the CMUT to generate a ramp voltage. If the ramp begins at the voltage of an LV positive power supply (referred to as VDDA) and proceeds to ground, or if the ramp begins at ground and proceeds to VDDA, the ultrasound device may use the receive circuitry (e.g., a comparator in the receive circuitry) to measure the time $T_{ramp}$ that it takes from the beginning of the ramp to when the ramp crosses a reference voltage Vref. In some embodiments, two ramps may be used, one during current sourcing and one during current sinking, such that one ramp proceeds from VDDA to ground (during current sinking) and one proceeds from ground to VDDA (during current sourcing), and the average of the $T_{ramp}$ measured for each ramp may be used to compute C. In some embodiments, multiple repeated measurements of the time for ramp voltages to cross the reference voltage may be performed during current sourcing, and these multiple measurements of time may be averaged. Additionally, multiple repeated measurements of the time for ramp voltages to cross the reference voltage may be performed during current sinking, and these multiple measurements of time may be averaged. The two averaged results, one result for current sourcing and one for current sinking, may then be averaged together. Alternatively, the multiple measurements from current sourcing and from current sinking may be averaged together. It should be appreciated that in some embodiments, measuring the time for a ramp voltage to cross the reference voltage during current sourcing may be performed prior to measuring the time for a ramp voltage to cross a reference voltage during current sinking, while in some embodiments, measuring the time for a ramp voltage to cross the reference voltage during current sinking may be performed prior to measuring the time for a ramp voltage to cross the reference voltage during current sourcing.

In some embodiments, the ultrasound device may operate a current source (e.g., the current source 1685 or 1688) to inject a current to an input terminal of receive circuitry (e.g., to an amplifier (e.g., the amplifier 364) configured as a comparator). The input terminal is electrically coupled to the CMUT. For example, to electrically couple the CMUT to the input terminal of the receive circuitry, a switch (e.g., the receive switch 362) between the CMUT and the input terminal of the receive circuitry may be closed. The current may charge or discharge the CMUT to generate a ramp voltage. The receive circuitry (e.g., a comparator in the receive circuitry) may be used to measure the time $T_{ramp}$ it takes for the ramp voltage to cross a reference voltage Vref. In some embodiments, one current source may source a first current to the input terminal of the receive circuitry to charge or discharge the CMUT and generate a first ramp voltage. A first time $T_{ramp}$ for the first ramp voltage to cross a reference voltage may be measured. A second current source may sink a second current from the input terminal of the receive circuitry to charge or discharge the CMUT and generate a second ramp voltage. A second time $T_{ramp}$ for the second ramp voltage to cross the reference voltage may be measured. Both the first and second times $T_{ramp}$ may be used to compute the capacitance (e.g., by averaging the $T_{ramp}$ values). In some embodiments, multiple repeated measurements of the time for ramp voltages to cross the reference voltage may be performed during current sourcing, and these multiple measurements of time may be averaged. Additionally, multiple repeated measurements of the time for ramp voltages to cross the reference voltage may be performed during current sinking, and these multiple measurements of time may be averaged. The two averaged results, one result for current sourcing and one for current sinking, may then be averaged together. Alternatively, the multiple measurements from current sourcing and from current sinking may be averaged together. It should be appreciated that in some embodiments, measuring the time for a ramp voltage to cross the reference voltage during current sourcing may be performed prior to measuring the time for a ramp voltage to cross a reference voltage during current sinking, while in some embodiments, measuring the time for a ramp voltage to cross the reference voltage during current sinking may be performed prior to measuring the time for a ramp voltage to cross the reference voltage during current sourcing.

The capacitance of the CMUT may be computed based on $T_{ramp}$ as $$C = \frac{I_{ramp} \times T_{ramp}}{VDDA - Vref}.$$

In some embodiments, the ultrasound device may measure $T_{ramp}$ but not use $T_{ramp}$ to measure C. In some embodiments, the ultrasound device itself may use $T_{ramp}$ to measure C. Further description of circuitry that may be configured to perform the act 3904 may be found with reference to FIGS. 8-13 and 15-16.

The ultrasound device may repeat acts 3902 and 3904 by choosing a new bias voltage $V_{BIAS}$ to apply to the CMUT at act 3902 and repeating the measurement at the new bias voltage at act 3904. In some embodiments, the ultrasound device may use increasing values of the bias voltage. At act 3906, if there is an additional bias voltage to apply, the ultrasound device returns back to act 3902 and applies the new bias voltage. If there is not an additional bias voltage to apply, the process 3900 terminates.

In some embodiments, the values of the capacitance C of the CMUT or the values of the parameter (e.g., $T_{ramp}$) related to the capacitance of the CMUT at each of the bias voltages $V_{BIAS}$ may represent a C vs. $V_{BIAS}$ curve. In some embodiments, the ultrasound device may transmit the measurements of the capacitance or of the parameter (e.g., $T_{ramp}$) related to the capacitance of the CMUT to a processing device (e.g., the processing device 4404 described below) which is in operative communication with the ultrasound device. For example, the ultrasound device may transmit the processing device over a wired communication link (e.g., over Ethernet, a Universal Serial Bus (USB) cable or a Lightning cable) or over a wireless communication link (e.g., over a BLUETOOTH, WiFi, or ZIGBEE wireless communication.

Figure 40:
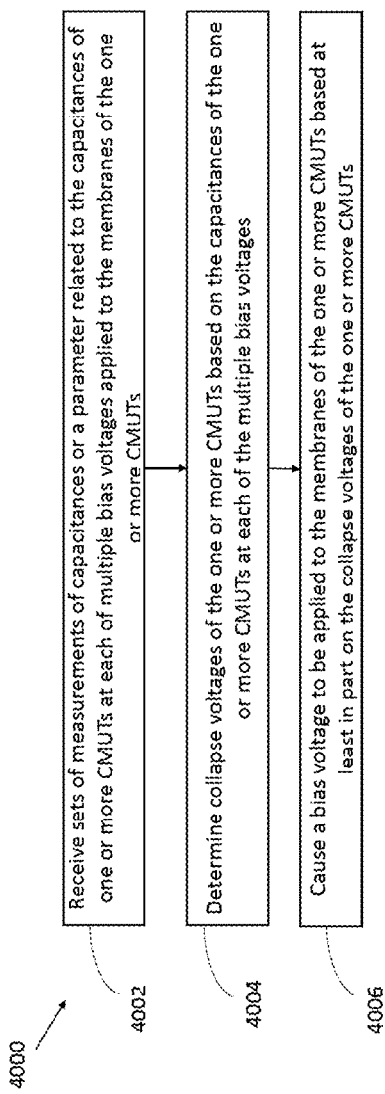
FIG. 40 illustrates a process for determining the collapse voltages of one or more CMUTs and applying a bias voltage to the CMUTs, in accordance with certain embodiments described herein.

FIG. 40 illustrates a process 4000 for determining the collapse voltages of one or more CMUTs (e.g., one of which may be the CMUT 152) and applying a bias voltage to the CMUTs, in accordance with certain embodiments described herein. The process 4000 may be performed by a processing device (e.g., the processing device 4404 described below).

The processing device may be in operative communication with an ultrasound device (e.g., the ultrasound device 4402 described below). For example, the processing device may be a mobile phone, tablet, or laptop. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). In some embodiments, the process 4000 may be performed by the ultrasound device.

In act 4002, the processing device receive sets of measurements of capacitances or a parameter related to the capacitances of one or more CMUTs at each of multiple bias voltages applied to the CMUTs. Further description of such measurements may be found above with reference to the process 3900. As described above, the ultrasound device may measure $T_{ramp}$, which can be used to compute C. In some embodiments, for each of the multiple CMUTs, the processing device may receive a set of measurements of $T_{ramp}$ at multiple bias voltages. In some embodiments, the set of measurements of $T_{ramp}$ may have been collected at increasing bias voltages. In some embodiments, for each of the multiple CMUTs, the processing device may receive a set of measurements of C at multiple increasing bias voltages. The ultrasound device may transmit the sets of measurements to the processing device over a wired communication link (e.g., over Ethernet, a Universal Serial Bus (USB) cable or a Lightning cable) or over a wireless communication link (e.g., over a BLUETOOTH, WiFi, or ZIGBEE wireless communication. In some embodiments, the multiple CMUTs may be all the CMUTs in a CMUT array on the ultrasound device. In some embodiments, the multiple CMUTs may be a subset of the CMUTs in a CMUT array on the ultrasound device.

In act 4004, the processing device determines collapse voltages of the one or more CMUTs based on the capacitances of the CMUTs at each of the multiple bias voltages received in act 4002. In embodiments in which the processing device receives sets of measurements of $T_{ramp}$ at multiple bias voltages, the processing device may compute C at each of the bias voltages for each CMUT using the equation $$C = \frac{I_{ramp} \times T_{ramp}}{VDDA - Vref},$$

where $I_{ramp}$ is the constant current inputted to the CMUT that generates the ramp voltage from ground to the voltage of the positive power supply VDDA or from VDDA to ground and $T_{ramp}$ is the time it takes from the beginning of the ramp to when the ramp cross the reference voltage Vref. As described above, in some embodiments, the ultrasound device may measure multiple values for $T_{ramp}$ at a single bias voltage for each CMUT; for example, the ultrasound device may measure one value for an increasing ramp voltage and another value for a decreasing ramp voltage. In such embodiments, the processing device may average the multiple values of $T_{ramp}$ and use the averaged value to compute C for each CMUT.

The measurements of C at each of the bias voltages $V_{BIAS}$ may constitute a C vs. $V_{BIAS}$ curve for each CMUT. A discontinuity may be observed in this curve when there is contact between the membrane and the substrate of the CMUT. If the C vs. $V_{BIAS}$ curve was generated by increasing the value of $V_{BIAS}$, then the value of $V_{BIAS}$ at which this contact occurs (i.e., the value of $V_{BIAS}$ at which the discontinuity occurs) may be the collapse voltage of the CMUT 152. The processing device may thus determine the collapse voltage of each CMUT by computing the first or second derivative of the C vs. $V_{BIAS}$ curve and determining where a discontinuity occurs in the curve. The processing device may calculate the first and/or second derivative of the C vs. $V_{BIAS}$ curve in order to determine where the discontinuity occurs.

In act 4006, the processing device causes a bias voltage to be applied to the one or more CMUTs based at least in part on the collapse voltages of the one or more CMUTs. The bias voltage applied to the CMUT may be measured between the membranes of the CMUTs and the bottom electrodes at the substrates of the CMUTs. If the desired bias voltage is $V_{BIAS}$, and the bottom electrodes at the substrates of the CMUTs are at virtual ground, then applying $V_{BIAS}$ to the CMUT may be accomplished by applying $V_{BIAS}$ to the membrane. In some embodiments, the processing device may compute the average of the collapse voltages of the CMUTs that were computed in act 4004 and cause a bias voltage to be applied to the CMUTs that is greater than the average of the collapse voltages by a particular offset voltage. Thus, the same bias voltage may be applied to each of the CMUTs. In some embodiments in which the same bias voltage is applied to each of the CMUTs, each of the CMUTs may share one membrane. Alternatively, the processing device may cause different bias voltages to be applied to different CMUTs. For example, if one group of CMUTs shares one membrane and another group of CMUTs shares another membrane, then the processing device may calculate the average collapse voltage for each group and cause a bias voltage to be applied to each group that is greater than that group's average collapse voltage by the particular offset voltage. As another example, if each CMUT has its own membrane, the processing device may cause a bias voltage to be applied to each CMUT that is greater than that CMUT's collapse voltage by the particular offset voltage. In some embodiments, when computing the average of the collapse voltages of multiple CMUTs, the processing device may exclude from the computation those CMUTs having membranes that are stuck to their substrates. The processing device may determine which CMUTs are stuck based on determining that the CMUTs' C vs. $V_{BIAS}$ curves do not have discontinuities.

In some embodiments, the offset voltage may be approximately equal to or between 20-30V. For example, the offset voltage may be approximately equal to 25, 26, 27, 28, 29, or 30V. In some embodiments, the offset voltage may be approximately equal to or between 20-45V. For example, the offset voltage may be approximately equal to 20, 21, 22, 23, 24, 25, 26, 27, 28, 29, 30, 31, 32, 33, 34, or 35V. However, other suitable offset voltages may be used. In some embodiments, a different offset voltage may be used when imaging different anatomical regions. For example, different presets (i.e., where each preset is a predetermined set of imaging parameters optimized for imaging a particular anatomical region) may use different offset voltages. Applying a bias voltage to the CMUTs that is a particular offset voltage greater than the average of the collapse voltages of the CMUTs may help to ensure that, as the collapse voltages of the CMUTs change with time, the value of the bias voltage applied to the CMUTs minus the average of the collapse voltages of the CMUTs remains the same. This may help to increase the acoustic efficiency of the CMUT. The processing device may transmit an instruction to the ultrasound device to apply the bias voltage over a wired communication link (e.g., over Ethernet, a Universal Serial Bus (USB) cable or a Lightning cable) or over a wireless communication link (e.g., over a BLUETOOTH, WiFi, or ZIGBEE wireless communication. In some embodiments, the ultrasound device may use a DC-DC converter (e.g., the DC-DC converter 4339 described below) to apply the bias voltage $V_{BIAS}$ to the membrane of the CMUT.

Figure 41:
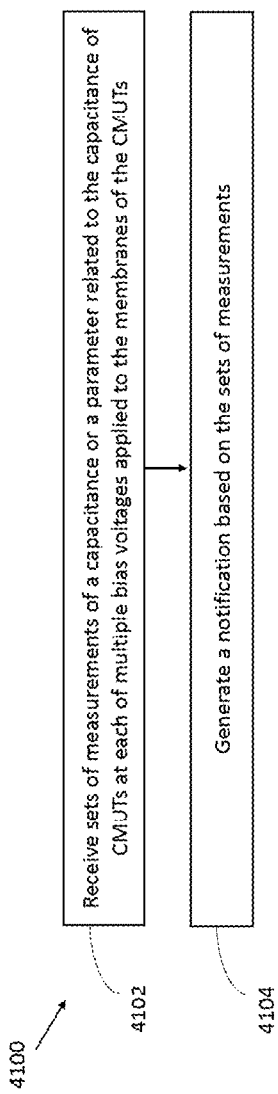
FIG. 41 illustrates a process for generating a notification based on measurements of capacitance of CMUTs, in accordance with certain embodiments described herein.

FIG. 41 illustrates a process 4100 for generating a notification based on measurements of capacitance of CMUTs (e.g., one of which may be the CMUT 152), in accordance with certain embodiments described herein. The process 4100 may be performed by a processing device (e.g., the processing device 4404 described below). The processing device may be in operative communication with an ultrasound device (e.g., the ultrasound device 4402 described below). For example, the processing device may be a mobile phone, tablet, or laptop. The ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). In some embodiments, the process 4100 may be performed by the ultrasound device.

In act 4102, the processing device receive sets of measurements of capacitance or a parameter related to the capacitance of multiple CMUTs at each of multiple bias voltages applied to the multiple CMUTs. The act 4102 is the same as the act 4002. In some embodiments, the multiple CMUTs may be all the CMUTs in a CMUT array on the ultrasound device. In some embodiments, the multiple CMUTs may be a subset of the CMUTs in a CMUT array on the ultrasound device. As described above, in some embodiments, the ultrasound device may measure $T_{ramp}$, which can be used to compute C, the capacitance of a CMUT at a given bias voltage. In some embodiments, at act 4102, the processing device may receive a set of measurements of $T_{ramp}$ at multiple bias voltages for each of the multiple CMUTs. In some embodiments, at act 4102, the processing device may receive a set of measurements of C at multiple bias voltages for each of the multiple CMUTs.

In embodiments in which the processing device receives sets of measurements of $T_{ramp}$ at multiple bias voltages, the processing device may compute C at each of the bias voltages for each CMUT using the equation $$C = \frac{I_{ramp} \times T_{ramp}}{VDDA - Vref},$$

where $I_{ramp}$ is the constant current inputted to the CMUT that generates the ramp voltage from ground to the voltage of the positive power supply VDDA or from VDDA to ground and $T_{ramp}$ is the time it takes from the beginning of the ramp to when the ramp cross the reference voltage Vref. As described above, in some embodiments, the ultrasound device may measure multiple values for $T_{ramp}$ at a single bias voltage for each CMUT; for example, the ultrasound device may measure one value for an increasing ramp voltage and another value for a decreasing ramp voltage. In such embodiments, the processing device may average the multiple values of $T_{ramp}$ and use the averaged value to compute C for each CMUT. The measurements of C at each of the bias voltages $V_{BIAS}$ may constitute a C vs. $V_{BIAS}$ curve for each CMUT.

If the membrane of a CMUT is stuck to its substrate, the CMUT's C vs. $V_{BIAS}$ curve may not have a discontinuity. This may be because, for the entire range of $V_{BIAS}$ values, the membrane is collapsed. Thus, in some embodiments, the processing device may determine whether the membrane of a CMUT is stuck to its substrate (referred to for simplicity as a CMUT being "stuck") by determining whether a discontinuity occurs in the C vs. $V_{BIAS}$ curve. The processing device may determine whether a discontinuity occurs by computing the derivative (e.g., first or second derivative) of the C vs. $V_{BIAS}$ curve. The processing device may then count how many CMUTs are stuck. In some embodiments, if this number exceeds a threshold, the processing device may generate a notification as described with reference to act 4104. In some embodiments, based on this count, the processing device may then determine what percentage of the CMUTs from which measurements were collected are stuck and/or what percentage of the CMUTs in the CMUT array are stuck. If this percentage exceeds a threshold, the processing device may generate a notification as described with reference to act 4104. The threshold percentage may be, for example, approximately equal to or between 0.1%-0.5%, 0.1%-1%, 0.1%-5%, 0.1%-10%, 0.1%-15%, 0.1%-20%, 0.1%-25%, 0.5%-1%, 0.5%-5%, 0.5%-10%, 0.5%-15%, 0.5%-20%, 0.5%-25%, 1-25%, 5-25%, 10-25%, 15-25%, 20-25%, 1-20%, 5-20%, 10-20%, 15-20%, 1-15%, 5-15%, 10-15%, 1-10%, or 1-5%. As specific examples, the threshold percentage may be approximately equal to 1%, 5%, 10%, 15%, 20%, or 25%, although other suitable thresholds may be used.

In act 4104, the processing device generates a notification based on the sets of measurements received in act 4102. As described above, the processing device may generate the notification if a percentage of stuck CMUTs exceeds a threshold, and the percentage of stuck CMUTs may be determined based on the sets of measurement received in act 4102, as described above. The notification may be, for example, that the ultrasound device should be replaced. In some embodiments, the processing device may generate the notification on its own display screen for the user. In some embodiments, the processing device may transmit, over a wireless network, a notification to a supplier of the ultrasound device that the ultrasound device should be replaced.

Figure 42:
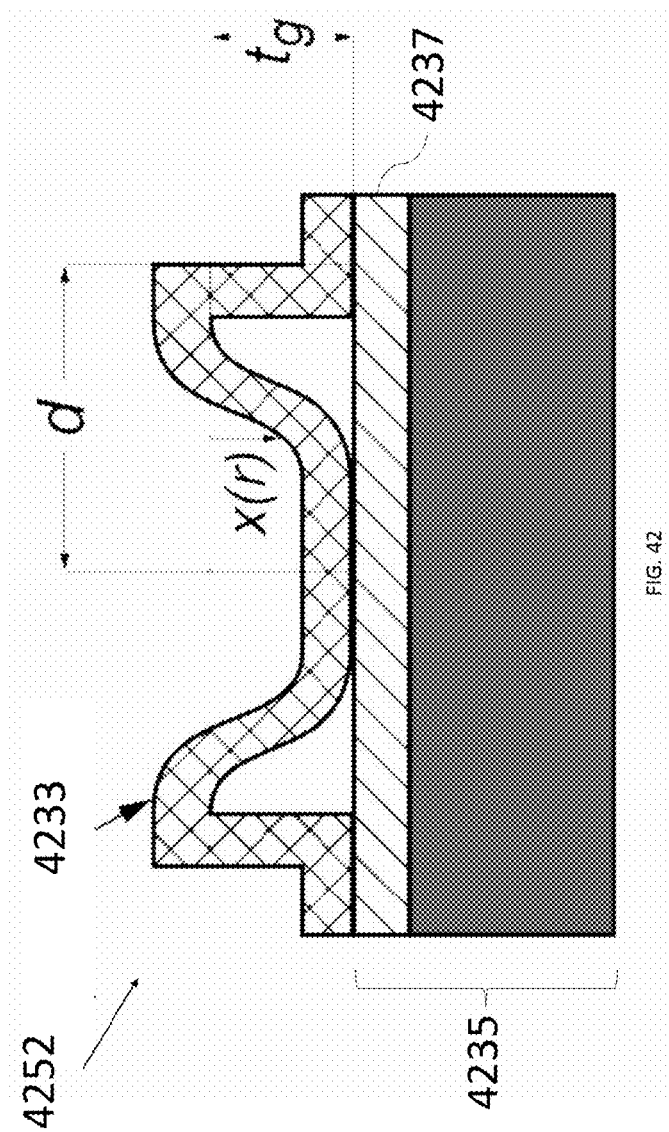
FIG. 42 illustrates a schematic diagram of a CMUT, in accordance with certain embodiments described herein.

FIG. 42 illustrates a schematic diagram of a CMUT 4252 (which may be the same as the CMUT 152), in accordance with certain embodiments described herein. The CMUT 4252 includes a membrane 4233 and a substrate 4235. The substrate 4235 includes an electrode 4237. In FIG. 42, the membrane 4233 is collapsed onto the substrate 4235, such that the membrane 4233 contacts the substrate 4235. The static membrane deflection profile at a DC bias voltage ($V_{BIAS}$) across the CMUT 4252 is determined by the applied electrical force and the restoring force of the membrane 4233. Without being limited by theory, the capacitance C of the CMUT 4252 can be calculated by integrating the ring capacitance of the same deflection distance using the following equation:

$$C(VBIAS) = \int_0^d \frac{2\pi\varepsilon_0 r}{t_{g-x(r)}} dr,$$

where d is the diameter of the membrane 4233 and $t_g$ is the effective height of the gap between the membrane 4233 and the substrate 4235. It can be appreciated from the above equation that when there is contact between the membrane 4233 and the substrate, meaning that ∃r:$t_g$=x(r), a discontinuity should be observed in the capacitance C vs. $V_{BIAS}$ curve.

Figure 43:
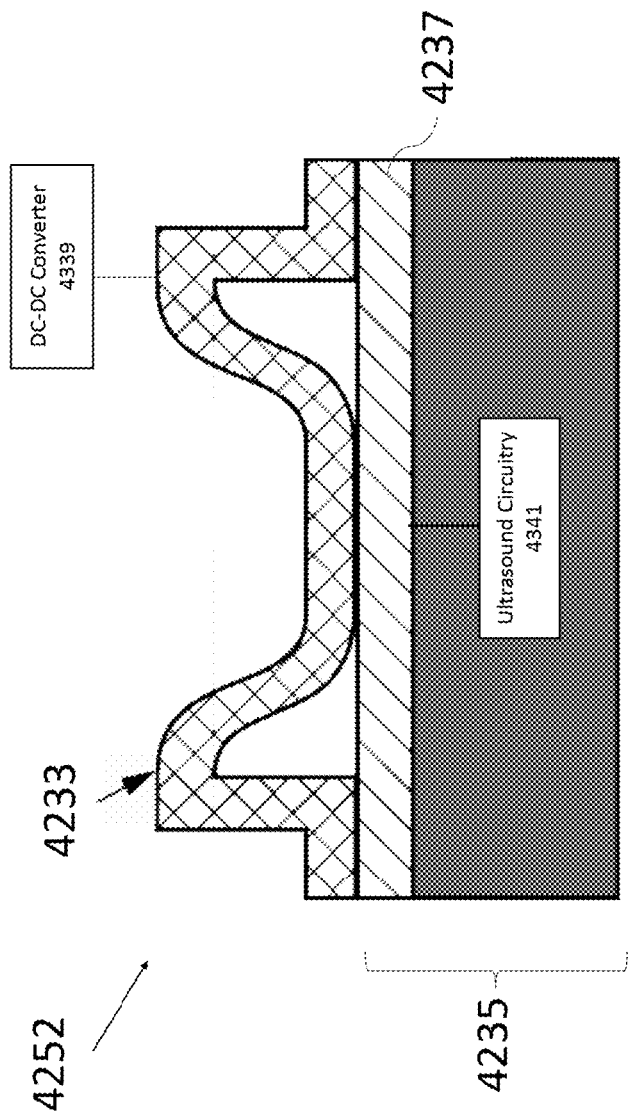
FIG. 43 illustrates another schematic diagram of the CMUT of FIG. 42, in accordance with certain embodiments described herein.

FIG. 43 illustrates another schematic diagram of the CMUT 4252 (which may be the same as the CMUT 152), in accordance with certain embodiments described herein. FIG. 43 further illustrates a DC-DC converter 4339 and ultrasound circuitry 4341. The DC-DC converter 4339 may be, for example, a charge pump. The DC-DC converter 4339 may be disposed, for example, in an ultrasound device (e.g., the ultrasound device 4402 described below) but not in the substrate 4235. The ultrasound circuitry 4341 is disposed in the substrate 4235 of the CMUT 4252 and is electrically coupled to the electrode 4237. The ultrasound circuitry 4341 may be, for example, integrated circuitry that is integrated in a semiconductor chip. The ultrasound circuitry 4341 may include, for example, any of the ultrasound circuitry, illustrated in FIG. 3-34 or 43 (e.g., the ultrasound circuitry 2727, 2827, 2927, 3027, 3127, 3227, 3327, 3427, or 4310). The DC-DC converter 4339 may apply a voltage to the membrane 4233 of the CMUT and the ultrasound circuitry 4341 may apply a voltage to the electrode 4237. If the ultrasound circuitry 4341 establishes a virtual ground at the electrode 4237, and the DC-DC converter 4339 applies a voltage $V_{BIAS}$ to the membrane 4233, then the voltage applied to the CMUT 4252 (i.e., between the membrane 4233 and the electrode 4237 of the CMUT 152) may be $V_{BIAS}$.

Figure 44:
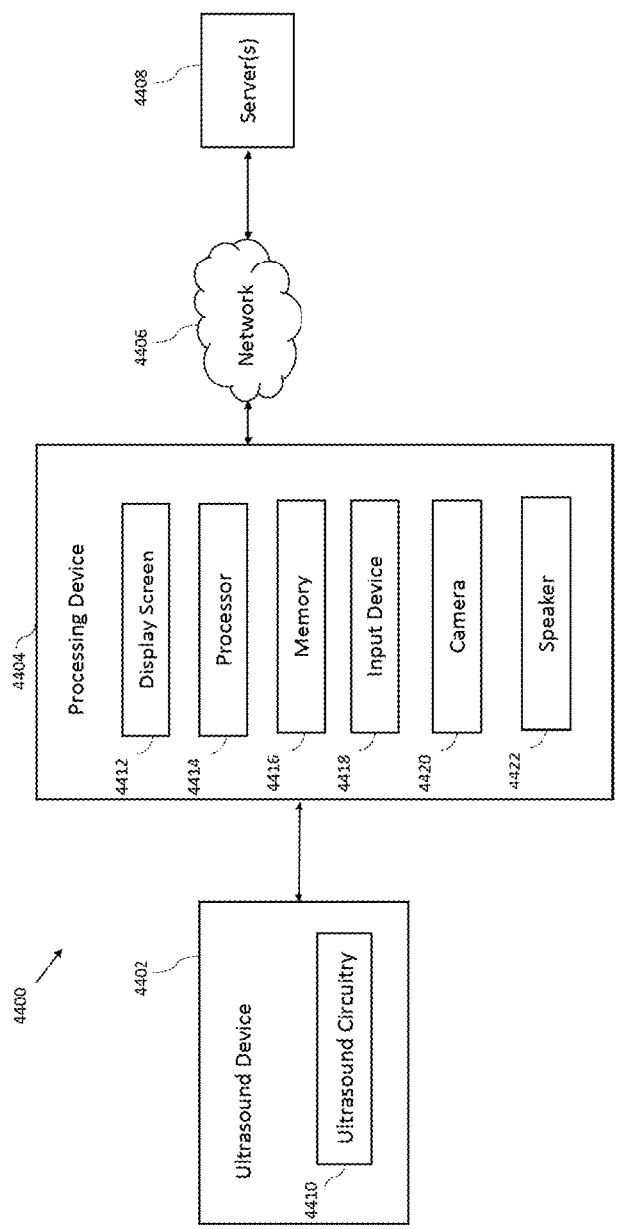
FIG. 44 illustrates a schematic block diagram of an example ultrasound system upon which various aspects of the technology described herein may be practiced.

FIG. 44 illustrates a schematic block diagram of an example ultrasound system 4400 upon which various aspects of the technology described herein may be practiced. The ultrasound system 4400 includes an ultrasound device 4402, a processing device 4404, a network 4406, and one or more servers 4408. The processing device 4404 may be any of the processing devices described herein. The ultrasound device 4402 may be any of the ultrasound devices described herein.

The ultrasound device 4402 includes ultrasound circuitry 4410. The processing device 4404 includes a camera 4420, a display screen 4412, a processor 4414, a memory 4416, an input device 4418, and a speaker 4422. The processing device 4404 is in wired (e.g., through a lightning connector or a mini-USB connector) and/or wireless communication (e.g., using BLUETOOTH, ZIGBEE, and/or WiFi wireless protocols) with the ultrasound device 4402. The processing device 4404 is in wireless communication with the one or more servers 4408 over the network 4406.

The ultrasound device 4402 may be configured to generate ultrasound data that may be employed to generate an ultrasound image. The ultrasound device 4402 may be constructed in any of a variety of ways. In some embodiments, the ultrasound device 4402 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 4410 may be configured to generate the ultrasound data. The ultrasound circuitry 4410 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed on the same chip as other electronic components in the ultrasound circuitry 4410 (e.g., transmit circuitry, receive circuitry, control circuitry, power management circuitry, and processing circuitry) to form a monolithic ultrasound device. The ultrasound circuitry 4410 may include any of the ultrasound circuitry illustrated in FIGS. 3-34 (e.g., the ultrasound circuitry 2727, 2827, 2927, 3027, 3127, 3227, 3327, 3427, or 4341) as well as the DC-DC converter 4337. The ultrasound device 4402 may transmit ultrasound data and/or ultrasound images to the processing device 4404 over a wired (e.g., through a lightning connector or a mini-USB connector) and/or wireless (e.g., using BLUETOOTH, ZIGBEE, and/or WiFi wireless protocols) communication link. The ultrasound circuitry 4410 may be configured to perform certain of the processes described herein (e.g., the processes 3600, 3700, 3800, and/or 3900).

Referring now to the processing device 4404, the processor 4414 may include specially-programmed and/or special-purpose hardware such as an application-specific integrated circuit (ASIC). For example, the processor 4414 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The processing device 4404 may be configured to process the ultrasound data received from the ultrasound device 4402 to generate ultrasound images for display on the display screen 4412. The processing may be performed by, for example, the processor 4414. The processor 4414 may also be adapted to control the acquisition of ultrasound data with the ultrasound device 4402. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 4404 may be configured to perform certain of the processes (e.g., the processes 4000-4100) described herein using the processor 4414 (e.g., one or more computer hardware processors) and one or more articles of manufacture that include non-transitory computer-readable storage media such as the memory 4416. The processor 4414 may control writing data to and reading data from the memory 4416 in any suitable manner. To perform certain of the processes described herein, the processor 4414 may execute one or more processor-executable instructions stored in one or more non-transitory computer-readable storage media (e.g., the memory 4416), which may serve as non-transitory computer-readable storage media storing processor-executable instructions for execution by the processor 4414. The camera 4420 may be configured to detect light (e.g., visible light) to form an image. The camera 4420 may be on the same face of the processing device 4404 as the display screen 4412. The display screen 4412 may be configured to display images and/or videos, and may be, for example, a liquid crystal display (LCD), a plasma display, and/or an organic light emitting diode (OLED) display on the processing device 4404. The input device 4418 may include one or more devices capable of receiving input from a user and transmitting the input to the processor 4414. For example, the input device 4418 may include a keyboard, a mouse, a microphone, touch-enabled sensors on the display screen 4412, and/or a microphone. The display screen 4412, the input device 4418, the camera 4420, and the speaker 4422 may be communicatively coupled to the processor 4414 and/or under the control of the processor 4414.

It should be appreciated that the processing device 4404 may be implemented in any of a variety of ways. For example, the processing device 4404 may be implemented as a handheld device such as a mobile smartphone or a tablet. Thereby, a user of the ultrasound device 4402 may be able to operate the ultrasound device 4402 with one hand and hold the processing device 4404 with another hand. In other examples, the processing device 4404 may be implemented as a portable device that is not a handheld device, such as a laptop. In yet other examples, the processing device 4404 may be implemented as a stationary device such as a desktop computer. The processing device 4404 may be connected to the network 4406 over a wired connection (e.g., via an Ethernet cable) and/or a wireless connection (e.g., over a WiFi network). The processing device 4404 may thereby communicate with (e.g., transmit data to or receive data from) the one or more servers 4408 over the network 4406. For example, a party may provide from the server 4408 to the processing device 4404 processor-executable instructions for storing in one or more non-transitory computer-readable storage media (e.g., the memory 4426) which, when executed, may cause the processing device 4404 to perform certain of the processes (e.g., the processes 4000-4100) described herein. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application).

FIG. 44 should be understood to be non-limiting. For example, the ultrasound system 4400 may include fewer or more components than shown and the processing device 4404 and ultrasound device 4402 may include fewer or more components than shown. In some embodiments, the processing device 4404 may be part of the ultrasound device 4402.

Figure 45:
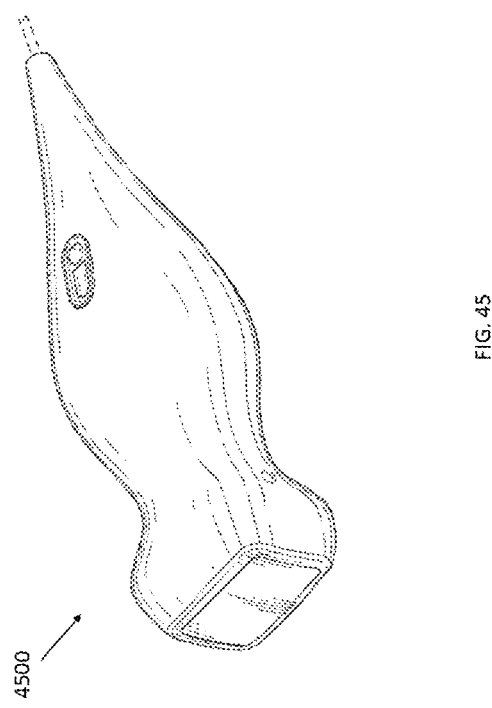
FIG. 45 illustrates an example handheld ultrasound probe, in accordance with certain embodiments described herein.

FIG. 45 illustrates an example handheld ultrasound probe 4500, in accordance with certain embodiments described herein. The handheld ultrasound probe 4500 may be the same as the ultrasound device 4402 and may contain all of the ultrasound circuitry illustrated in FIG. 3-34 or 44 (e.g., the ultrasound circuitry 2727, 2827, 2927, 3027, 3127, 3227, 3327, 3427, 4341 or 4410).

Figure 46:
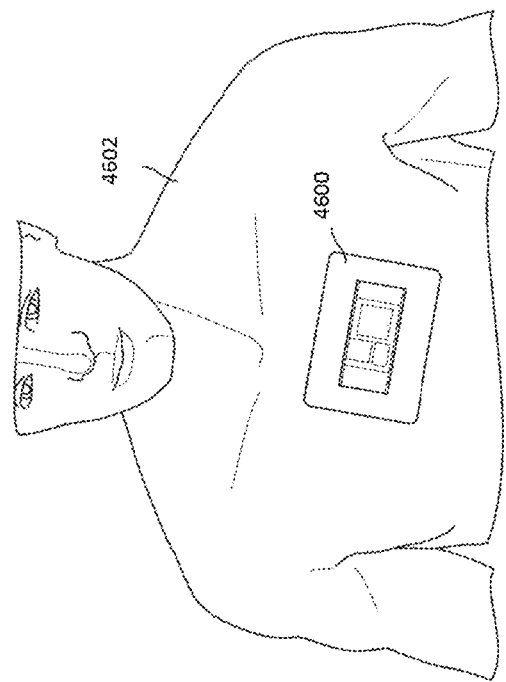
FIG. 46 illustrates an example wearable ultrasound patch, in accordance with certain embodiments described herein.

FIG. 46 illustrates an example wearable ultrasound patch 4600, in accordance with certain embodiments described herein. The wearable ultrasound patch 4600 is coupled to a subject 4602. The wearable ultrasound patch 4600 may be the same as the ultrasound device 4402 and may contain all of the ultrasound circuitry illustrated in FIG. 3-34 or 44 (e.g., the ultrasound circuitry 2727, 2827, 2927, 3027, 3127, 3227, 3327, 3427, 4341 or 4410).

Figure 47:
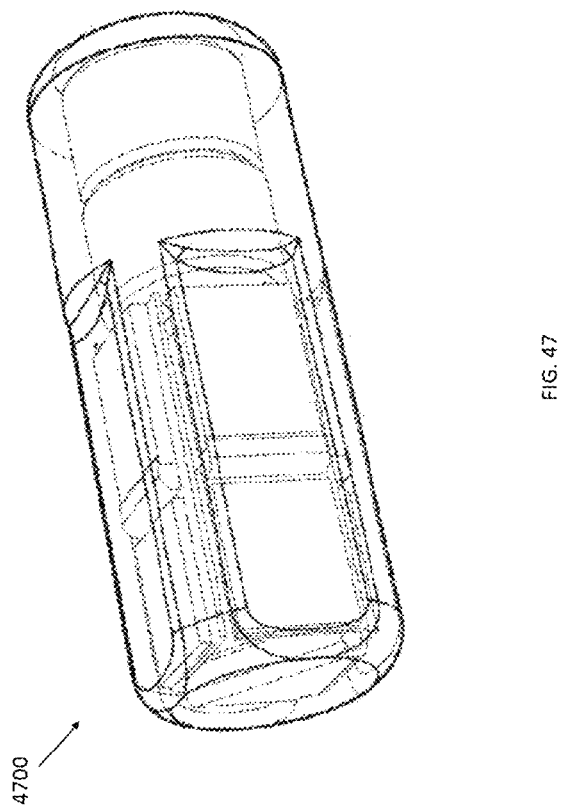
FIG. 47 illustrates an example ingestible ultrasound pill, in accordance with certain embodiments described herein.

FIG. 47 illustrates an example ingestible ultrasound pill 4700, in accordance with certain embodiments described herein. The ingestible ultrasound pill 4700 may be the same as the ultrasound device 4402 and may contain all of the ultrasound circuitry illustrated in FIG. 3-34 or 44 (e.g., the ultrasound circuitry 2727, 2827, 2927, 3027, 3127, 3227, 3327, 3427, 4341, or 4410).

Further description of the handheld ultrasound probe 4500, the wearable ultrasound patch 4600, and the ingestible ultrasound pill 4700 may be found in U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application), which is incorporated by reference herein in its entirety.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An ultrasound device operable in testing and imaging modes, the ultrasound device comprising:
   a pulser configured to generate voltage pulses;
   receive circuitry;
   a capacitive micromachined ultrasonic transducer (CMUT) couplable to the receive circuitry; and
   a built-in self-test (BIST) circuit including a transconductance amplifier coupled between the pulser and the receive circuitry,
   wherein during the testing mode, the transconductance amplifier is turned on and is configured to convert the voltage pulses to a current signal and the receive circuitry is configured to convert to current signal to a voltage signal for verifying operation of the pulser, and
   wherein during the imaging mode, the transconductance amplifier is turned off and the voltage pulses are provided to the CMUT to output ultrasonic waves.

2. The ultrasound device according to claim 1, wherein the transconductance amplifier includes a linearized transconductance amplifier.

3. The ultrasound device according to claim 1, wherein the transconductance amplifier includes a source-degenerated linearized transconductance amplifier.

4. The ultrasound device according to claim 1, further comprising a resistor ladder, and wherein the transconductance amplifier and the pulser are configured to receive, as input signals, voltages from the resistor ladder.

5. The ultrasound device according to claim 1, wherein the transconductance amplifier is coupled between the pulser and a circuit in the receive circuitry configurable as a transimpedance amplifier.

6. The ultrasound device according to claim 5, wherein the transimpedance amplifier is configured to convert the current signal to a low-voltage signal.

7. The ultrasound device according to claim 1, wherein the transconductance amplifier is coupled between the pulser and a circuit in the receive circuitry configurable as a comparator.

8. The ultrasound device according to claim 1, wherein the transconductance amplifier is coupled between the pulser and a circuit in the receive circuitry configurable as a delta-sigma analog-to-digital converter.

9. The ultrasound device of claim 1, wherein:
   the pulser is configured to use a first power supply;
   the transconductance amplifier is configured to use a second power supply;
   the receive circuitry is configured to use a third power supply; and
   the first power supply has a higher voltage than the second power supply and the second power supply has a higher voltage than the third power supply.

10. The ultrasound device of claim 1, wherein during the imaging mode, the pulser and the receive circuitry remain on.

11. The ultrasound device of claim 1, wherein the pulser, the receive circuitry, the CMUT, and the transconductance amplifier are disposed within a single package.

12. The ultrasound device of claim 1, wherein BIST circuit is disposed on a same semiconductor chip as the pulser, the receive circuitry, and/or the CMUT.

* * * * *